(12) United States Patent
Wu et al.

(10) Patent No.: US 6,808,926 B1
(45) Date of Patent: *Oct. 26, 2004

(54) REPRESSING GENE EXPRESSION IN PLANTS

(75) Inventors: Keqiang Wu, Nepean (CA); Brian L. A. Miki, Ottawa (CA); Lining Tian, London (CA); Daniel C. W. Brown, Ilderton (CA)

(73) Assignee: Her Majesty the Queen in Right of Canada, as Represented by the Minister of Agriculture and Agri-Food, Ottawa (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 26 days.

(21) Appl. No.: 09/645,337

(22) Filed: Aug. 25, 2000

Related U.S. Application Data

(63) Continuation-in-part of application No. 09/383,971, filed on Aug. 27, 1999, now abandoned.

(51) Int. Cl.[7] .................. C12N 15/29; C12N 15/82; C12N 15/90; A01H 1/00; A01H 5/10

(52) U.S. Cl. ............... 435/468; 435/320.1; 435/419; 536/23.6; 800/260; 800/278; 800/287; 800/288; 800/298

(58) Field of Search ....................... 435/69.1, 320.1, 435/410, 419, 468; 800/278, 287, 295, 298, 260, 288; 536/23.6

(56) References Cited

U.S. PATENT DOCUMENTS

| | | | |
|---|---|---|---|
| 5,770,720 A | 6/1998 | Deuel et al. | 536/24.5 |
| 5,801,027 A | 9/1998 | Bennett et al. | 435/468 |
| 5,808,034 A | 9/1998 | Bridges et al. | 536/24.1 |
| 5,830,462 A | 11/1998 | Crabtree et al. | 424/93.24 |
| 6,287,843 B1 * | 9/2001 | Baldwin et al. | 435/252.3 |

FOREIGN PATENT DOCUMENTS

| | | | |
|---|---|---|---|
| WO | WO 90/08829 | 8/1990 | C12N/15/82 |
| WO | WO 97/08195 | 3/1997 | C07K/14/00 |
| WO | WO 97/30164 | 8/1997 | C12N/15/82 |
| WO | WO 97/35990 | 10/1997 | C12N/15/55 |
| WO | WO 98/48825 | 11/1998 | A61K/38/02 |
| WO | WO 98/59062 | 12/1998 | C12N/15/82 |

OTHER PUBLICATIONS

Wu et al., Plant J., 2000, vol. 22, pp. 19–27.*
Genbank Accession NO. AF014824.*
L. Allan et al., "Role for N–CoR and Histone Deacetylase in Sin3–Mediated Transcriptional Repression," *Nature* vol. 387, pp. 49–55 (1997).

S. Emiliani et al., "Characterization of a Human RPD3 Ortholog, HDAC3," *Proc. Natl. Acad. Sci.*, vol. 95, pp. 2795–2800 (1998).
W. Fischle et al., "A New Family of Human Histone Deacetylases Related to Saccharomyces Cerevisiae HDA1p," *The Journal of Biological Chemistry*, vol. 274, No. 17, pp. 11713–11720 (1999).
V. Gelmetti et al., "Aberrant Recruitment of the Nuclear Receptor Corepressor–Histone Deacetylase Complex by the Acute Mycloid Leukemia Fusion Partner ETO," *Molecular and Cellular Biology*, vol. 18, No. 12, pp. 7185–7191 (1998).
C. Hassig et al., "Histone Deacetylase Activity Is Required for Full Transcriptional Repression by mSinA." *Cell.* vol. 89, pp. 341–347 (1997).
C. Hassig et al., "A Role for Histone Deacetylase Activity in HDAC1–Mediated Transcriptional Repression." *Proc. Natl. Acad. Sci.*, vol. 95, pp. 3519–3524 (1998).
D. Kadosh et al., "Repression of Umeb Involves Recruitment of a Complex Containing Sin3 Corepressor and Rpd3 Histone Deacetylase to Target Promoters," *Cell.* vol. 89, pp. 365–371 (1997).
S. Khochbin et al., "The Origin and Utility of Histone Deacetylases," *Federation of European Biochemical Societies*, vol. 419, pp. 157–160 (1997).
A. Lusser et al., "Identificaiton of Maize Histone Deacetylase HD2 as an Acidic Nucleolar Phosphoprotein," *Science*, vol. 277, pp. 88–91 (1997).

(List continued on next page.)

*Primary Examiner*—Ashwin Mehta
(74) *Attorney, Agent, or Firm*—Oliff & Berridge, PLC

(57) ABSTRACT

Posttranslational modification of histones, in particular acetylation and deacetylation are involved in the regulation of gene expression. Histone deacetylases remove acetyl groups from histone proteins. The present invention is directed to a method of regulating gene expression in a transgenic plant comprising, introducing into a plant a first chimeric nucleotide sequence comprising a first regulatory element in operative association with a coding sequence of interest, and an upstream activating sequence, and a second chimeric nucleotide sequence comprising a second regulatory element in operative association with a nucleotide sequence encoding histone deaceytlase and a nucleotide sequence encoding a DNA binding protein, and growing the transgenic plant. Furthermore, a method for regulating gene expression of an endogenous coding sequence of interest, or modifying a developmental, physiological or biochemical pathway in a plant is provided comprising introducing into a plant a chimeric nucleotide sequence comprising a regulatory element in operative association with a nucleotide sequence encoding histone deaceytlase fused with a nucleotide sequence encoding a DNA binding protein capable of interacting with an endogenous controlling sequence, for example an upstream activating sequence, and growing the transgenic plant. This invention also relates to novel histone deacetylase obtained from plants, to novel chimeric construct comprising these, or other histone deacetylase, and to transgenic plants, plant cells, or seeds comprising these chimeric constructs.

38 Claims, 28 Drawing Sheets

OTHER PUBLICATIONS

I., Nagy et al., "Nuclear Receptor Repression Kmediated by a Complex Containing SMRT, mSin3A, and Histone Deacetylase," *Cell.* vol. 89, pp. 373–380 (1997).

M. Pazin et al., "What's Up and Down with Histone Deacetylation and Transcription?" *Cell.* vol. 89, pp. 325–328 (1997).

A. Philpott et al., "Nucleoplasmin Remodels Sperm Chromatin in Xenopus Egg Extracts." Cell vol. 69, pp. 759–767 (1992).

V. Rossi et al., "Identificaiton and Characterisation of an RPD3 Homologue From Maize (Zea mays L.) that is able to Complement an rpd3 Null Mutant of Saccharomyces Cerevisiae," *Mol. Gen. Genet.*, vol. 258, pp. 288–296 (1998).

S. Rundlett et al., "HDA1 and RPD3 are Members of Distinct Yeast Histone Deaceytlas Complexes that Regulate Silencing and Transcription," *Proc. Natl. Acad. Sci.,* vol. 93, pp. 14503–14508 (1996).

A. Verdel et al., "Identification of a New Family of Higher Eukaryotic Histone Deaceytlases," *The Journal of Biological Chemistry,* vol. 274, No. 4, pp. 2440–2445 (1999).

M. Vidal et al. "RPD3 Encodes a Second Factor Required To Achieve Maximum Positive and Negative Transcriptional States in Saccharomyces Cerevisiae," *Molecular and Cellular Biology*, vol. 11, No. 12, pp. 6317–6327 (1991).

W. Yang et al., "Transciptional Repression by YY1 is Mediated by Interaction with a Mammalian Homology of the Yeast Global Reulator RPD3," Proc. Natl. Acad. Sci, USA, vol. 93, pp. 12845–12850 (1996).

\* cited by examiner

Figure 1A

```
   1 agagagcagctcccttcccctcggcgaggaggaaggaagaagaaagccagagagagagag
  61 agagatcatcgcagcttctcctccgaccatttgactgcgactgtgattacaacacaccgt
 121 tgatcctacgaaaagaggtaatggatactggcggcaattcgctggcgtccggacctgat
                             M  D  T  G  G  N  S  L  A  S  G  P  D    13
 181 ggtgtgaagaggaaagtttgttattctatgaccctgaggtcggcaattactactatggc
      G  V  K  R  K  V  C  Y  F  Y  D  P  E  V  G  N  Y  Y  Y  G    33
 241 caaggtcatcccatgaagccccatcgcatccgcatgacccatgccctcctcgctcactac
      Q  G  H  P  M  K  P  H  R  I  R  M  T  H  A  L  L  A  H  Y    53
 301 ggtctccttcagcatatgcaggttctcaagcccttccctgcccgcgaacgtgatctctgc
      G  L  L  Q  H  M  Q  V  L  K  P  F  P  A  R  E  R  D  L  C    73
 361 cgcttccacgccgacgactatgtctcttttctccgcagcattacccctgaaacccagcaa
      R  F  H  A  D  D  Y  V  S  F  L  R  S  I  T  P  E  T  Q  Q    93
 421 gatcagattcgccaacttaagcgcttcaatgttggtgaagactgtcccgtctttgacggc
      D  Q  I  R  Q  L  K  R  F  N  V  G  E  D  C  P  V  F  D  G   113
 481 ctttattcctttgccagacctatgctggaggatctgttggtggctctgtcaagcttaac
      L  Y  S  F  C  Q  T  Y  A  G  G  S  V  G  G  S  V  K  L  N   133
 541 cacggcctctgcgatattgccatcaactgggctggtggtctccatcacgctaagaagtgc
      H  G  L  C  D  I  A  I  N  W  A  G  G  L  H  H  A  K  K  C   153
 601 gaggcctctggcttctgttacgtcaatgatatcgtcttagctatcctagagctcctaag
      E  A  S  G  F  C  Y  V  N  D  I  V  L  A  I  L  E  L  L  K   173
 661 cagcatgagcgtgttctttatgtcgatattgatatccaccacggggatggagtggaggag
      Q  H  E  R  V  L  Y  V  D  I  D  I  H  H  G  D  G  V  E  E   193
 721 gcatttatgctactgacagggttatgactgtctcgtttcataaatttggtgattacttt
      A  F  Y  A  T  D  R  V  M  T  V  S  F  H  K  F  G  D  Y  F   213
 781 cccggtacaggtcacattcaggatataggttatggtagcggaaagtactattctctcaat
      P  G  T  G  H  I  Q  D  I  G  Y  G  S  G  K  Y  Y  S  L  N   233
 841 gtaccactggatgatggaatcgatgatgagagctatcatctgttattcaagcccatcatg
      V  P  L  D  D  G  I  D  D  E  S  Y  H  L  L  F  K  P  I  M   253
 901 gggaaagttatggaaattttccgaccaggggctgtggtattgcaatgtggtgctgactcc
      G  K  V  M  E  I  F  R  P  G  A  V  V  L  Q  C  G  A  D  S   273
 961 ctatctggggatcggttaggttgcttcaatctttcaatcaaaggtcatgctgagtcgtc
      L  S  G  D  R  L  G  C  F  N  L  S  I  K  G  H  A  E  C  V   293
1021 aaatttatgagatcgttcaatgttcccctactgctcttgggtggtggtggttacactatc
      K  F  M  R  S  F  N  V  P  L  L  L  G  G  G  G  Y  T  I   313
1081 cgcaatgttgcccgttgctggtgctacgagactggagttgcacttggagttgaagttgaa
      R  N  V  A  R  C  W  C  Y  E  T  G  V  A  L  G  V  E  V  E   333
1141 gacaagatgccggagcatgaatattatgaatactttggtccagactatacacttcacgtt
      D  K  M  P  E  H  E  Y  Y  E  Y  F  G  P  D  Y  T  L  H  V   353
1201 gctccaagtaacatggaaaataagaattctcgtcagatgcttgaagagattcgcaatgac
      A  P  S  N  M  E  N  K  N  S  R  Q  M  L  E  E  I  R  N  D   373
1261 cttctccacaatctctctaagcttcagcatgctccaagtgtaccatttcaggaaagacca
      L  L  H  N  L  S  K  L  Q  H  A  P  S  V  P  F  Q  E  R  P   393
1321 cctgatacagagactcccgaggttgatgaagaccaagaagatggggataaaagatgggat
      P  D  T  E  T  P  E  V  D  E  D  Q  E  D  G  D  K  R  W  D   413
1381 ccggattcagacatggatgttgatgatgaccgtaaacctataccaagcagagtaaaaaga
      P  D  S  D  M  D  V  D  D  D  R  K  P  I  P  S  R  V  K  R   433
1441 gaagctgttgaaccagatacaaaggacaaggatggactgaaaggaattatggagcgtgga
      E  A  V  E  P  D  T  K  D  K  D  G  L  K  G  I  M  E  R  G   453
1501 aaaggttgtgaggtggaggtggatgagagtggaagcactaaggttacaggagtaaaccca
      K  G  C  E  V  E  V  D  E  S  G  S  T  K  V  T  G  V  N  P   473
1561 gtgggagtggaggaagcaagtgtgaaaatggaagaggaaggaacaaacaagggtggggcg
      V  G  V  E  E  A  S  V  K  M  E  E  E  G  T  N  K  G  G  A   493
1621 gagcaggcgtttcctcctaaaacataagactcggagcttctaatttcttgctactttttc
      E  Q  A  F  P  P  K  T  *                                     502
1681 tgtctatcaaatgttgctagttaagtttctggagttgttgttgttgtaagcactcctctg
1741 ttttagaggattgagcacggatatgtatttattcgttgcatgtctgaatgatgatatgat
1801 atgacaa
```

Figure 1B

```
   1 gtgcccacaactcctagtaatgactttctcaggcattgttgacacaaattttgctctgag
  61 taaaacttggaatagagagagactctgagtgagagagagattctgagtgagagacggag
 121 atggaggcagacgaaagcggcatctctctgccgtcgggacccgacggacgtaagcggcga
      M  E  A  D  E  S  G  I  S  L  P  S  G  P  D  G  R  K  R  R    20
 181 gtcagttacttctacgagccgacgatcggagactactactacggtcaaggccacccgatg
      V  S  Y  F  Y  E  P  T  I  G  D  Y  Y  Y  G  Q  G  H  P  M    40
 241 aagcctcaccggatccgtatggctcatagcctaatcattcactatcacctccaccgtcgc
      K  P  H  R  I  R  M  A  H  S  L  I  I  H  Y  H  L  H  R  R    60
 301 ttagaaatcagtcgccctagcctcgctgacgcctccgatatcggccgattccattcgccg
      L  E  I  S  R  P  S  L  A  D  A  S  D  I  G  R  F  H  S  P    80
 361 gagtatgttgacttcctcgcttccgtttcgccggaatctatgggcgatccttccgctgca
      E  Y  V  D  F  L  A  S  V  S  P  E  S  M  G  D  P  S  A  A   100
 421 cgaaacctaaggcgattcaatgtcggtgaggattgtcctgtcttcgacggacttttgat
      R  N  L  R  R  F  N  V  G  E  D  C  P  V  F  D  G  L  F  D   120
 481 ttttgccgtgcttccgccggaggttctattggtgctgccgtcaaattaaacagacaggac
      F  C  R  A  S  A  G  G  S  I  G  A  A  V  K  L  N  R  Q  D   140
 541 gctgatatcgctatcaattgggcggtgggcttcaccatgctaagaaaagcgaggcttct
      A  D  I  A  I  N  W  G  G  L  H  H  A  K  K  S  E  A  S   160
 601 gggttttgctatgtaaacgacatcgtgctagggattctggagttgctcaagatgtttaag
      G  F  C  Y  V  N  D  I  V  L  G  I  L  E  L  L  K  M  F  K   180
 661 cgggttctctacatagatattgatgtccaccatggagatggagtggaagaagcgttttac
      R  V  L  Y  I  D  I  D  V  H  H  G  D  G  V  E  E  A  F  Y   200
 721 accactgatagagttatgactgtttctttccacaaatttggggacttttttcccaggaact
      T  T  D  R  V  M  T  V  S  F  H  K  F  G  D  F  F  P  G  T   220
 781 ggtcacataagagatgttggcgctgaaaagggaaatactatgctctaaatgttccacta
      G  H  I  R  D  V  G  A  E  K  G  K  Y  Y  A  L  N  V  P  L   240
 841 aacgatggtatggacgatgaaagtttccgcagcttgtttagacctcttatccagaaggtt
      N  D  G  M  D  D  E  S  F  R  S  L  F  R  P  L  I  Q  K  V   260
 901 atggaagtgtatcagccagaggcagttgttcttcagtgtggtgctgactccttaagtggt
      M  E  V  Y  Q  P  E  A  V  V  L  Q  C  G  A  D  S  L  S  G   280
 961 gatcggttggggttgcttcaacttatcagtcaagggtcacgctgattgccttcggttctta
      D  R  L  G  C  F  N  L  S  V  K  G  H  A  D  C  L  R  F  L   300
1021 agatcttacaacgttcctctcatggtgttgggtggtgaagggtatactattcgaaatgtt
      R  S  Y  N  V  P  L  M  V  L  G  G  E  G  Y  T  I  R  N  V   320
1081 gcccgttgctggtgttatgagactgcagttgctgttggagtagagccggacaacaaactc
      A  R  C  W  C  Y  E  T  A  V  A  V  G  V  E  P  D  N  K  L   340
1021 ccttacaatgagtattttgagtatttcggcccagattatacgcttcatgtcgacccaagt
      P  Y  N  E  Y  F  E  Y  F  G  P  D  Y  T  L  H  V  D  P  S   360
1201 cctatggagaatttaaacacgcccaagatatggagaggataaggaacacgttgctggaa
      P  M  E  N  L  N  T  P  K  D  M  E  R  I  R  N  T  L  L  E   380
1261 caactttcgggactaatacacgcacctagcgtccagtttcagcacacaccaccagtcaat
      Q  L  S  G  L  I  H  A  P  S  V  Q  F  Q  H  T  P  P  V  N   400
1321 cgagttttggacgagccggaagatgacatggagacaagaccaaaacctcgcatctggagt
      R  V  L  D  E  P  E  D  D  M  E  T  R  P  K  P  R  I  W  S   420
1381 ggaactgcgacttatgaatcagacagtgacgatgatgataaacctcttcatggttactca
      G  T  A  T  Y  E  S  D  S  D  D  D  K  P  L  H  G  Y  S   440
1441 tgtcgtggtggcgcaactacggacagggactctaccggtgaagatgaaatggatgacgat
      C  R  G  G  A  T  T  D  R  D  S  T  G  E  D  E  M  D  D  D   460
1501 aacccagagccagacgtgaatcctccatcgtcttaaaccagcttgatggtttggtgtctc
      N  P  E  P  D  V  N  P  P  S  S  *                           471
1561 ttttgccatatgataatgtcggcagatttaagaaacaagttaggggaatgaatgattctt
1621 tgatgttttttcagcaacctttgaattctgtgaaaacgctgcattgattagaacagtga
1681 caactgactagtatttttgcccaagttagaaatcagaatatgtgaaaaaaaaaaaaaa
1741 aaaaaaaaggcggccgctctagaggatccaagcttacgtacgcgtgcatgcgacgtcat
```

Figure 2A

```
  1  cacgcgtccgtaaaaatcctctcttttctcaaccttgattcttagccatggagttctgg
                                                        M  E  F  W     4
 61  ggaattgaagttaaatcaggaaagccagttacagtgactcctgaagaaggcattcttatc
      G  I  E  V  K  S  G  K  P  V  T  V  T  P  E  E  G  I  L  I   24
121  cacgtttctcaggcatcgcttggagaatgtaaaaacaagaagggagagtttgtgccttta
      H  V  S  Q  A  S  L  G  E  C  N  K  K  G  E  F  V  P  L     44
181  catgtaaaggttgggaaccagaacttggttctgggaactctatcgactgagaacatccct
      H  V  K  V  G  N  Q  N  L  V  L  G  T  L  S  T  E  N  I  P   64
241  cagcttttctgtgatttggtattcgacaaggagtttgagctttctcacacttggggaaaa
      Q  L  F  C  D  L  V  F  D  K  E  F  E  L  S  H  T  W  G  K   84
301  ggaagtgtttactttgttggatacaaaactcccaacattgagccacaaggctattctgag
      G  S  V  Y  F  V  G  Y  K  T  P  N  I  E  P  Q  G  Y  S  E  104
361  gaagaagaggaagaagaggaagaagttcctgctgggaatgctgccaaggctgtagctaaa
      E  E  E  E  E  E  E  V  P  A  G  N  A  A  K  A  V  A  K     124
421  ccaaaggctaagcctgcagaagtgaagccagctgttgatgatgaagaggatgagtctgat
      P  K  A  K  P  A  E  V  K  P  A  V  D  D  E  E  D  E  S  D  144
481  tctgacggaatggatgaagatgattctgatggtgaggattctgaggaagaagagcctaca
      S  D  G  M  D  E  D  D  S  D  G  E  D  S  E  E  E  P  T     164
541  cctaagaagcctgcatcaagcaagaagagagctaatgaaactacccctaaagcacctgtg
      P  K  K  P  A  S  S  K  K  R  A  N  E  T  T  P  K  A  P  V  184
601  tcagcaaagaaggcgaaagtagcagttactcctcagaaaacagatgagaagaagaaaggg
      S  A  K  K  A  K  V  A  V  T  P  Q  K  T  D  E  K  K  K  G  204
661  ggaaaggctgcaaaccagagcccaaagtcggccagtcaagtctcatgtggttcatgcaag
      G  K  A  A  N  Q  S  P  K  S  A  S  Q  V  S  C  G  S  C  K  224
721  aagactttcaactcagggaatgcacttgagtctcacaacaaggccaagcacgctgctgcc
      K  T  F  N  S  G  N  A  L  E  S  H  N  K  A  K  H  A  A  A  244
781  aagtgaagtggtttcttattagagcttgtgatttctatggaattttgcctgtagtctta
      K  *                                                        245
841  tgaaaccttcggatttcttatatttctttgataacaagagtcttaatgaaagagagc
     cagttggagtcttaaaaaaaaaaaaaaaagggcggccgc
```

Figure 2B

```
   1  gtctttcgcttctaaaaaaaaacctaacaacctctcttctctcttcctcgttcaacaaca
  61  atggagttctggggagttgcggtgacaccaaaaaacgctactaaggtgactcctgaagaa
        M  E  F  W  G  V  A  V  T  P  K  N  A  T  K  V  T  P  E  E    20
 121  gacagccttgtccacatttctcaggcttcacttgactgcacagtgaaatctggagaatct
        D  S  L  V  H  I  S  Q  A  S  L  D  C  T  V  K  S  G  E  S    40
 181  gtggttttgagtgtgactgttggtggggctaaacttgttattggaacactttcacaagac
        V  V  L  S  V  T  V  G  G  A  K  L  V  I  G  T  L  S  Q  D    60
 241  aagttccctcagattagctttgatttggttttttgataaagagtttgagctttcacacagc
        K  F  P  Q  I  S  F  D  L  V  F  D  K  E  F  E  L  S  H  S    80
 301  ggtaccaaagcaaatgttcatttcattggctacaaatcccccaacatcgagcaggatgac
        G  T  K  A  N  V  H  F  I  G  Y  K  S  P  N  I  E  Q  D  D   100
 361  ttcactagttcggatgatgaggatgttcctgaagctgttcctgctcctgcccctactgct
        F  T  S  S  D  D  E  D  V  P  E  A  V  P  A  P  A  P  T  A   120
 421  gttactgccaacggaaatgctggagcagctgttgtcaaggctgacacaaagccaaaggcc
        V  T  A  N  G  N  A  G  A  A  V  V  K  A  D  T  K  P  K  A   140
 481  aaacctgccgaagtgaagcctgcagaagagaagcctgaatcagacgaggaagatgagtct
        K  P  A  E  V  K  P  A  E  K  P  E  S  D  E  E  D  E  S     160
 541  gatgatgaagatgagtctgaagaggatgatgactctgagaaggaatggatgttgatgaa
        D  D  E  D  E  S  E  D  D  S  E  K  G  M  D  V  D  E       180
 601  gatgactcagatgatgacgaggaggaggattctgaggatgaagaagaggaggagactcct
        D  D  S  D  D  D  E  E  E  D  S  E  D  E  E  E  E  T  P     200
 661  aagaagcctgagccaatcaacaagaagaggccaaatgaatctgtatccaaaacacccgtc
        K  K  P  E  P  I  N  K  K  R  P  N  E  S  V  S  K  T  P  V   220
 721  tctggaaagaaggcaaaaccagcagcagcaccagcttctactcctcagaagacagagaag
        S  G  K  K  A  K  P  A  A  A  P  A  S  T  P  Q  K  T  E  K   240
 781  aagaaggaggacacaccgccacaccacacccagctaagaaggggtggaaagtctcctgtg
        K  K  G  H  T  A  P  H  P  A  K  K  G  G  K  S  P  V        260
 841  aatgctaaccagagccccaagtctggaggtcaatcatccggtggtaacaacaacaagaag
        N  A  N  Q  S  P  K  S  G  G  Q  S  S  G  N  N  N  K  K     280
 901  ccattcaactcaggcaaacaatttggtggttccaacaacaagggttctaacaagggcaag
        P  F  N  S  G  K  Q  F  G  G  S  N  N  K  G  S  N  K  G  K   300
 961  ggaaagggtagagcttaaggacgtggatcaaggagaggttttggttttcgagtagatga
        G  K  G  R  A  *                                              305
1021  tgaaaacacttggaagtgtggttttggattttttatcttatttattagtataacttgtta
1081  tcggatgagctattttttgagtatttgcaatttctactttcctatgtaattcagtatatgaa
1141  tatttgctgaaatgagaagaagactcgaattgcaaacaaaaaaaaaaaaaaaaaaaaa
1201  aagggcggccgc
```

Figure 3

```
AtRPD3A  MT-----TGG NSIAN-GHDG VKPKVGYFYT IEVGNYYYG- GHPMKPHRIP  44
AtRPD3B  MEADESCI-- -SLFD-GHDG PKPRISVFYE ITIGDYYYG- GHPMKPHRIR  47
ZmRPD3   MPSSAGSGG NSLDVGFDG QKHRVAYFYT DEVGNYYYG- GHPMKPHRIP  50
RPD3     MVYEATPFD- ---EITVKPS DKHRVAYFYI ADVGNTAYGA GHPMKPHRIP  46

AtRPD3A  MTHALLAHYG LIQHMQVLKP FPARFRDCSF FHALDIVSFL RSITPETCQQ  94
AtRPD3B  MAHSLIFHH LHRRLEISPP SLADASLIGE HHSPIVDFL ASVSPISMGD  97
ZmRPD3   MTHISLLARYG LLNQMQVYRP NPARERLLCP FHAEDVINFI RSVTPETCQQ 100
RPD3     MAHSLIMNYG LYKKVLIYRA KPATKQFMCQ FHTDEYIDFI SRVTPDNLEM  96

AtRPD3A  QI--RQLKRF IVGEDCEVFP GLYSFCQTTA GGSVGGSVKI NHGLEDIAIN 142
AtRPD3B  PSAAPNIREF IVGEDCEVHP GIFDEGRASE KGIIAARVKI NRQDADIAIN 147
ZmRPD3   QI--PLLKRP IVGFESPVLG GLYSFCRTTA RASVGGAVKF NHGH-DIAIN 147
RPD3     --FKRESVKE IVKGDDCEVH PGLYEYCSIS G GGSMEGAARL NRGKCLVAVN 144

AtRPD3A  WAGGIHHAKK CEASGFCYVN DIVLAILELL MQHERVLVVI IDIHHGEGVE 192
AtRPD3B  WGGGIHHAKR SEASGFCYVN DIVLGILELL SMFKRVLYIL IDVHHGDGVE 197
ZmRPD3   WSGGIHHAKR CEASGFCYVN DIVLAILELL RHHERVLTVI IDIHHGDGVE 197
RPD3     YAGGLHHAKR SEASGFCYLN DIVLGIIELL RYHPRVLYID IDVHHGDGVE 194
                **          *                 *   * **

AtRPD3A  EAFYATDRVN TVSFHKFGEY PPGTGHIQDI GYGSGKYYSI NVPLDDGIDD 242
AtRPD3B  EAFYTTDRVN TVSFHKFGDF PPGTGHIRDV GAEKGKYYAI NVPLNDGMDD 247
ZmRPD3   EAFYTTDPVN TVSFHKFGDY PPGTKDIRDI GHSKGKYYSI NVPLDDGIDD 247
RPD3     EAFYTTDRVN TCSFHKYGEH PPGTGELRDI GVGAGKNTAV NVPLRDGIDD 244
              *           * *

AtRPD3A  ESTHLLFKPI MGKVMEIFRI DAVVLQCCAI SLSGDRLGCF NLSIKGHAEC 292
AtRPD3B  ESFPSLFREL HQKVMEVYCH EAVVLQCGAI SLSGDRLGCF NLSVKGHADY 297
ZmRPD3   ESTQSLFKPI MGKVMEVFRI RAVVLYCCAI SLSGDPLGCF NLSIKGHAEC 297
RPD3     ATYRSVFEIV IKKIHRWYCI SAVVLQCGGI SLSGDPLGCF NLSMECHANC 294

AtRPD3A  VKIMRSFNVP LLLLGGGGYT IRNVARCWCY ETGVALGVHV EDKMPEHEYY 342
AtRPD3B  LRFLRGYNVF LMVLCCEGYT IFNVARCWCY ETALVVGVES DNKLPYNEYF 347
ZmRPD3   VRHMRSFNVP LLLLGGGGYT IRNVARCWCY ETGVALGQFI EDKMEVNEYY 347
RPD3     VNYVKSHGIE MMVVGGGGYT MRNVARTWCF ETGLLNNWVL DKDLPYNEYY 344

AtRPD3A  EYFGPDYTLH VAPSNMENKI SRAMLEEIRI DLHHNLSKFQ HAFSFPFQFR 392
AtRPD3B  EYFGPDYTLH VDPSNMENKI TPKDMERIRI TLHHNLSGFI HAPSVQPQHT 397
ZmRPD3   EYFGPDYTLH VAPSNMENKI TRAQPDDIFS ----KLSKFR HAESHHFQEF 393
RPD3     FYYGPNYKFS VRPSNMFNVL TPEYLDHVMT NIPANLENTK YAPSVQLNHT 394

AtRPD3A  PPDTATPEVC EDCERGDKSW GPFNMIHVDI F--------F KRIPSFVKRF 434
AtRPD3B  PEVNRVLD-- ---------- EPHDDNF--- -------TF KF---FIWSG 421
ZmRPD3   VPDTHIPLQL EDKDLPLEFH DPDSDNEVDE HKAVEESSRF SILGIKIKRF 443
RPD3     F--------- --------F- DAEDLGDVEE DSA------- ---------- 409

AtRPD3A  AVEPDIKDKD GLKGIMERGK GCEVEVDESC STKVT---GV NPVGVEFAS- 480
AtRPD3B  TATYESDSDD DDKPL--HGY SC-------- --RGGATTFR DSTGEDFMDC 459
ZmRPD3   FGENAIRVQD GGRVASEH-R GLEPMAEDIC SSKQAPQADA SAMAIDFPSN 492
RPD3     ---------- ---------- ---------- ---------- ------EAKC 413

AtRPD3A  VKMFEEGTNK GGAEQAFFPF T                               501
AtRPD3B  DNPFFDVNP- -------FSS                               471
ZmRPD3   VKNFPSSTK LQGQAAAYHF P                               513
RPD3     TFGGSQYARD FHVFHDNEFY                               433
```

Figure 4

```
AtHD2A        I  S   KP T         I I V        KN      F P H      N   50
AtHD2B        VA T   KNAT         DS V I      -D TV    S V S T  G      49
ZmHD2         L      GSTV CE GY   FVL L   A    S-- SD  NALMY  IDD      48

AtHD2A     N  L    T  ENI  LFC               WG G  Y V    T      PQ  100
AtHD2B     A       Q   F   S                 SGT AN H I    S     QD   99
ZmHD2        AI    V   N H Q     I           SKTT  F T    VEQPFEE     98

AtHD2A    GYSEEEE E-  E      GNAA  ---------- ---  VA          V  136
AtHD2B    LFTSS D  V  P A    APT   A TA  N GA AVV  DT          E  149
ZmHD2     EMDL S  E   D  LNV ---   VVKE  K DE KKQ  SQE AV   SKSS DS 145

AtHD2A    ----D      S- I     ----  -------       E DS GE      E------- 162
AtHD2B    E PES      S DE ESE       -- EK         V D S D      SE E     197
ZmHD2     K SKD DDSD E  ET DSD      ET    DE LS   SE G D S D   D TS D   195

AtHD2A    P   --  AS  -S      TT  P A   A        V----         DE K--- 202
AtHD2B    E   --    P IN    P     S     G        P  AAPAS            -----TEK 240
ZmHD2     D   TP    V GK RP ES    L T L D         TPSS---      GG     ---- 238

AtHD2A    -  KA---- ----------  --------        AS      S -  T    229
AtHD2B    K   -- T                -----  KGG  PVNAN     S   G NNN  P     283
ZmHD2     -  AAV V         GKTIV  NND   VKSPK   SA      S P  KP S -S  I  286

AtHD2A      NALE- SH     HAAAK                                    245
AtHD2B      KQFGG N      GSNKGKGKG  RA                            305
ZmHD2       ET   QA- S   R   MGASESQ VQ                           307
```

Figure 9
A
Effector Plasmids
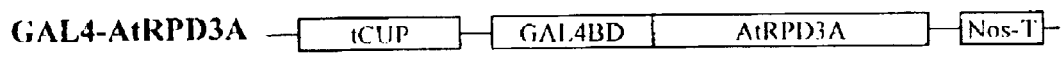
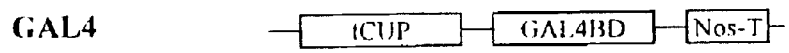
Reporter Plasmid
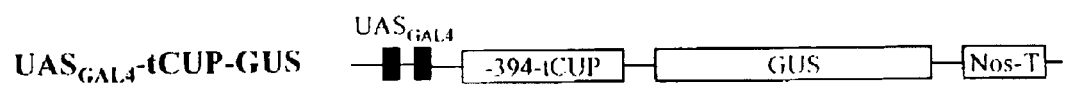
B
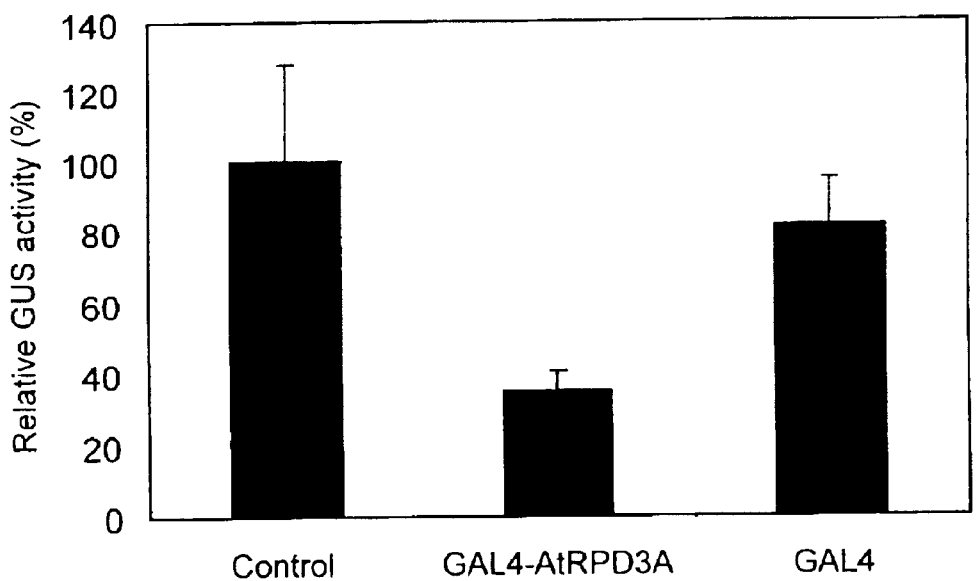

Figure 10
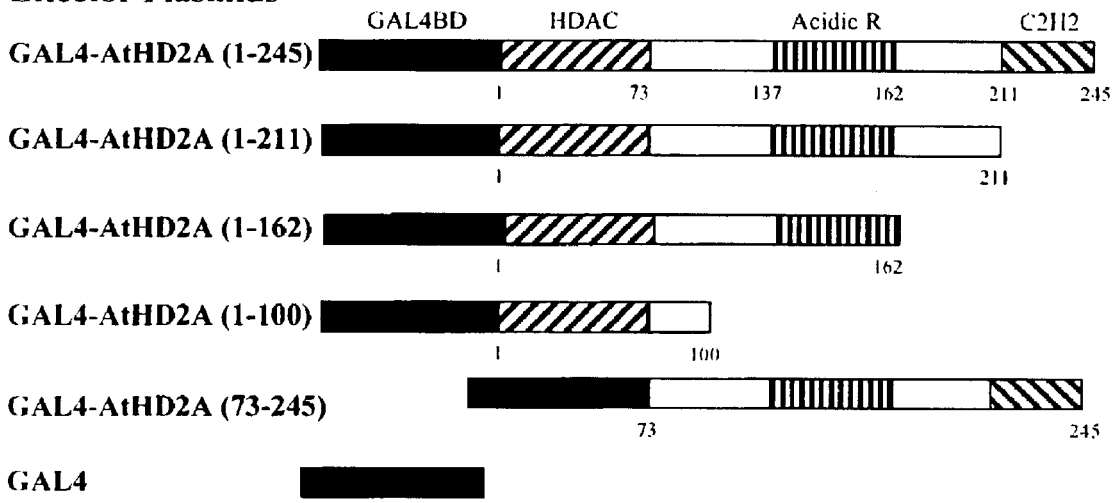
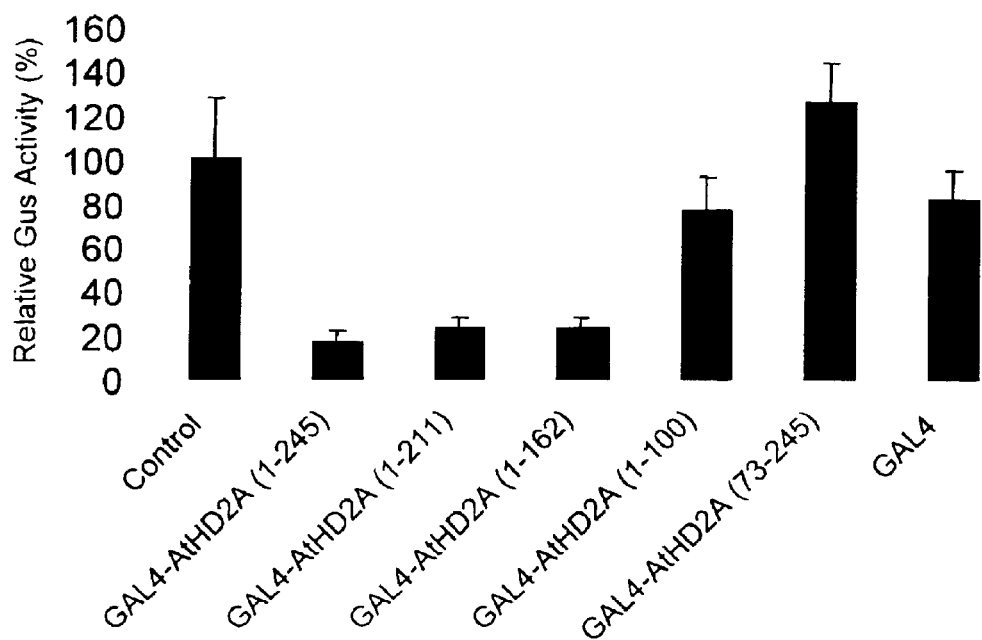

FIGURE 11
A
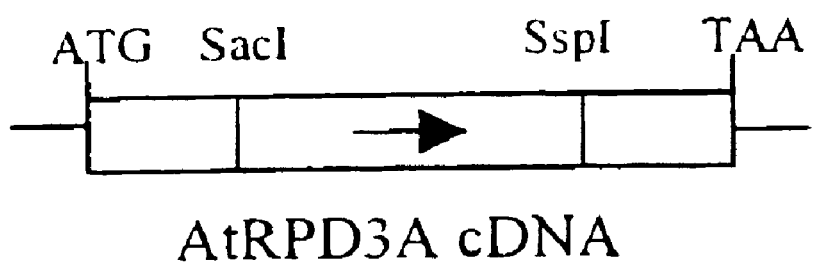
AtRPD3A cDNA
B
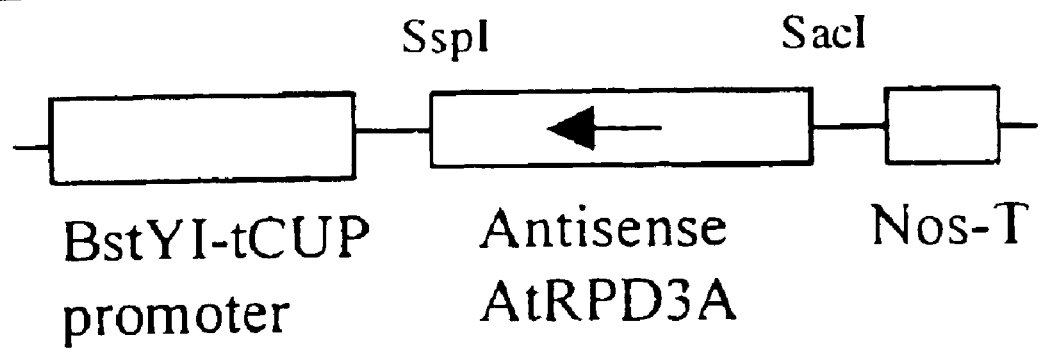

FIGURE 16

A
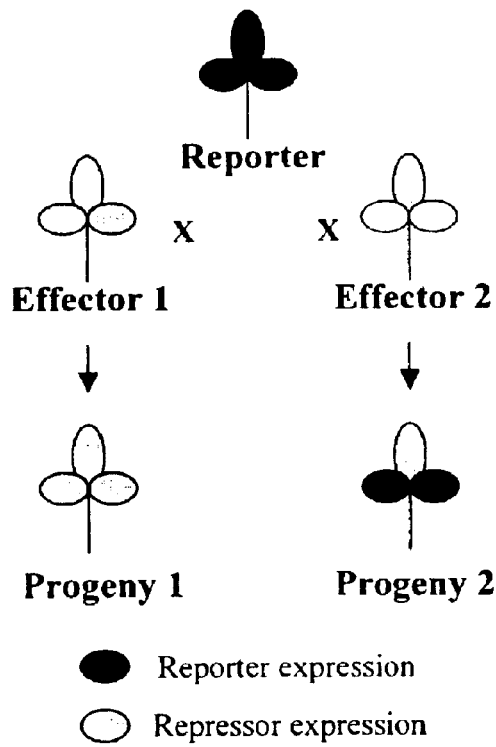
● Reporter expression
○ Repressor expression
B
Effector Plasmids
tCUP-GAL4/AtHD2A (Effector 1)
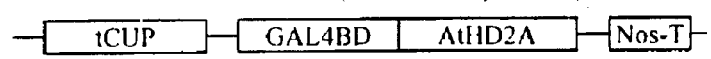
NAP1-GAL4/AtHD2A (Effector 2)
Reporter Plasmid
UAS$_{GAL4}$-tCUP-GUS (or UAS$_{GAL4}$-35S-GUS)
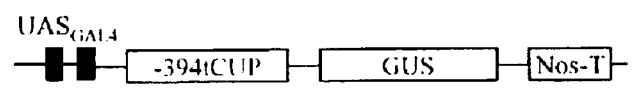
Figure 17

SEQUENCE LISTING

<160> NUMBER OF SEQ ID NOS: 14

<210> SEQ ID NO 1
<211> LENGTH: 1807
<212> TYPE: DNA
<213> ORGANISM: Arabidopsis thaliana

<400> SEQUENCE: 1

```
agagagcagc tcccttcccc tcggcgagga ggaaggaaga agaaagccag agagagagag      60
agagatcatc gcagcttctc ctccgaccat ttgactgcga ctgtgattac aacacaccgt     120
tgatcctacg aaaaagaggt aatggatact ggcggcaatt cgctggcgtc cggacctgat     180
ggtgtgaaga ggaaagtttg ttatttctat gaccctgagg tcggcaatta ctactatggc     240
caaggtcatc ccatgaagcc ccatcgcatc cgcatgaccc atgccctcct cgctcactac     300
ggtctccttc agcatatgca ggttctcaag cccttccctg cccgcgaacg tgatctctgc     360
cgcttccacg ccgacgacta tgtctctttt ctccgcagca ttacccctga acccagcaa     420
gatcagattc gccaacttaa gcgcttcaat gttggtgaag actgtcccgt ctttgacggc     480
ctttattcct tttgccagac ctatgctgga ggatctgttg gtggctctgt caagcttaac     540
cacggcctct gcgatattgc catcaactgg gctggtggtc tccatcacgc taagaagtgc     600
gaggcctctg gcttctgtta cgtcaatgat atcgtcttag ctatcctaga gctccttaag     660
cagcatgagc gtgttcttta tgtcgatatt gatatccacc acggggatgg agtggaggag     720
gcattttatg ctactgacag ggttatgact gtctcgtttc ataaatttgg tgattacttt     780
cccggtacag gtcacattca ggatataggt tatggtagcg aaagtactgt ttctctcaat     840
gtaccactgg atgatggaat cgatgatgag agctatcatc tgttattcaa gcccatcatg     900
gggaaagtta tggaaatttt ccgaccaggg gctgtggtat gcaatgtggt tgctgactcc     960
ctatctgggg atcggttagg ttgcttcaat cttccaatca aggtcatgc tgagtgcgtc    1020
aaatttatga gatcgttcaa tgttccccta ctgctcttgg gtggtggtgg ttacactatc    1080
cgcaatgttg cccgttgctg gtgctacgag actggagttg cacttggagt tgaagttgaa    1140
gacaagatgc cggagcatga atattatgaa tactttggtc cagactatac acttcacgtt    1200
gctccaagta acatggaaaa taagaattct cgtcagatgc ttgaagagat tcgcaatgac    1260
cttctccaca atctctctaa gcttcagcat gctccaagtg taccattca ggaaagacca    1320
cctgatacag agactcccga ggttgatgaa gaccaagaag atggggataa agatgggat    1380
ccggattcag acatggatgt tgatgatgac cgtaaaccta ccaagcag agtaaaaaga    1440
gaagctgttg aaccagatac aaaggacaag gatggactga aggaattat ggagcgtgga    1500
aaaggttgtg aggtggaggt ggatgagagt ggaagcacta aggttacagg agtaaaccca    1560
gtggagtgg aggaagcaag tgtgaaaatg gaagaggag gaacaaacaa gggtggggcg    1620
gagcaggcgt ttcctcctaa aacataagac tcggagcttc taatttcttg ctactttttc    1680
tgtctatcaa atgttgctag ttaagtttct ggagttgttg ttgttgtaag cactcctctg    1740
ttttagagga ttgagcacgg atatgtattt attcgttgca tgtctgaatg atgatatgat    1800
atgacaa                                                              1807
```

<210> SEQ ID NO 2
<211> LENGTH: 501
<212> TYPE: PRT
<213> ORGANISM: Arabidopsis thaliana

<400> SEQUENCE: 2

```
Met Asp Thr Gly Gly Asn Ser Leu Ala Ser Gly Pro Asp Gly Val Lys
 1               5                  10                  15

Arg Lys Val Cys Tyr Phe Tyr Asp Pro Glu Val Gly Asn Tyr Tyr Tyr
            20                  25                  30

Gly Gln Gly His Pro Met Lys Pro His Arg Ile Arg Met Thr His Ala
```

-continued

```
               35                  40                  45
Leu Leu Ala His Tyr Gly Leu Gln His Met Gln Val Leu Lys Pro
 50                  55                  60

Phe Pro Ala Arg Glu Arg Asp Leu Cys Arg Phe His Ala Asp Asp Tyr
 65                  70                  75                  80

Val Ser Phe Leu Arg Ser Ile Thr Pro Glu Thr Gln Gln Asp Gln Ile
                 85                  90                  95

Arg Gln Leu Lys Arg Phe Asn Val Gly Glu Asp Cys Pro Val Phe Asp
                100                 105                 110

Gly Leu Tyr Ser Phe Cys Gln Thr Tyr Ala Gly Gly Ser Val Gly Gly
                115                 120                 125

Ser Val Lys Leu Asn His Gly Leu Cys Asp Ile Ala Ile Asn Trp Ala
130                 135                 140

Gly Gly Leu His His Ala Lys Lys Cys Glu Ala Ser Gly Phe Cys Tyr
145                 150                 155                 160

Val Asn Asp Ile Val Leu Ala Ile Leu Glu Leu Leu Lys Gln His Glu
                165                 170                 175

Arg Val Leu Tyr Val Asp Ile Asp Ile His His Gly Asp Gly Val Glu
                180                 185                 190

Glu Ala Phe Tyr Ala Thr Asp Arg Val Met Thr Val Ser Phe His Lys
                195                 200                 205

Phe Gly Asp Tyr Phe Pro Gly Thr Gly His Ile Gln Asp Ile Gly Tyr
210                 215                 220

Gly Ser Gly Lys Tyr Tyr Ser Leu Asn Val Pro Leu Asp Asp Gly Ile
225                 230                 235                 240

Asp Asp Glu Ser Tyr His Leu Leu Phe Lys Pro Ile Met Gly Lys Val
                245                 250                 255

Met Glu Ile Phe Arg Pro Gly Ala Val Val Leu Gln Cys Gly Ala Asp
                260                 265                 270

Ser Leu Ser Gly Asp Arg Leu Gly Cys Phe Asn Leu Ser Ile Lys Gly
                275                 280                 285

His Ala Glu Cys Val Lys Phe Met Arg Ser Phe Asn Val Pro Leu Leu
290                 295                 300

Leu Leu Gly Gly Gly Gly Tyr Thr Ile Arg Asn Val Ala Arg Cys Trp
305                 310                 315                 320

Cys Tyr Glu Thr Gly Val Ala Leu Gly Val Glu Val Glu Asp Lys Met
                325                 330                 335

Pro Glu His Glu Tyr Tyr Glu Tyr Phe Gly Pro Asp Tyr Thr Leu His
                340                 345                 350

Val Ala Pro Ser Asn Met Glu Asn Lys Asn Ser Arg Gln Met Leu Glu
                355                 360                 365

Glu Ile Arg Asn Asp Leu Leu His Asn Leu Ser Lys Leu Gln His Ala
                370                 375                 380

Pro Ser Val Pro Phe Gln Glu Arg Pro Pro Asp Thr Glu Thr Pro Glu
385                 390                 395                 400

Val Asp Glu Asp Gln Glu Asp Gly Asp Lys Arg Trp Asp Pro Asp Ser
                405                 410                 415

Asp Met Asp Val Asp Asp Arg Lys Pro Ile Pro Ser Arg Val Lys
                420                 425                 430

Arg Glu Ala Val Glu Pro Asp Thr Lys Asp Lys Asp Gly Leu Lys Gly
                435                 440                 445

Ile Met Glu Arg Gly Lys Gly Cys Glu Val Glu Val Asp Glu Ser Gly
450                 455                 460
```

Ser Thr Lys Val Thr Gly Val Asn Pro Val Gly Val Glu Glu Ala Ser
465                 470                 475                 480

Val Lys Met Glu Glu Glu Gly Thr Asn Lys Gly Gly Ala Glu Gln Ala
                485                 490                 495

Phe Pro Pro Lys Thr
            500

<210> SEQ ID NO 3
<211> LENGTH: 1800
<212> TYPE: DNA
<213> ORGANISM: Arabidopsis thaliana
<220> FEATURE:
<221> NAME/KEY: misc_feature
<222> LOCATION: (1374)..(1374)
<223> OTHER INFORMATION: "n" is a or g or c or t

<400> SEQUENCE: 3

| | | | | | |
|---|---|---|---|---|---|
| gtgcccacaa | ctcctagtaa | tgactttctc | aggcattgtt | gacacaaatt | ttgctctgag | 60 |
| taaaacttgg | gaatagagag | agactctgag | tgagagagag | attctgagtg | agagacggag | 120 |
| atggaggcag | acgaaagcgg | catctctctg | ccgtcgggac | ccgacggacg | taagcggcga | 180 |
| gtcagttact | tctacgagcc | gacgatcgga | gactactact | acggtcaagg | ccacccgatg | 240 |
| aagcctcacc | ggatccgtat | ggctcatagc | ctaatcattc | actatcacct | ccaccgtcgc | 300 |
| ttagaaatca | gtcgccctag | cctcgctgac | gcctccgata | tcggccgatt | ccattcgccg | 360 |
| gagtatgttg | acttcctcgc | ttccgtttcg | ccggaatcta | tggcgatcc | ttccgctgca | 420 |
| cgaaacctaa | ggcgattcaa | tgtcggtgag | gattgtcctg | tcttcgacgg | acttttgat | 480 |
| ttttgccgtg | cttccgccgg | aggttctatt | ggtgctgccg | tcaaattaaa | cagacaggac | 540 |
| gctgatatcg | ctatcaattg | ggcggtgggg | cttcaccatg | ctaagaaaag | cgaggcttct | 600 |
| gggttttgct | atgtaaacga | catcgtgcta | gggattctgg | agttgctcaa | gatgtttaag | 660 |
| cgggttctct | acatagatat | tgatgtccac | catggagatg | gagtggaaga | agcgttttac | 720 |
| accactgata | gagttatgac | tgtttctttc | cacaaatttg | gggacttttt | cccaggaact | 780 |
| ggtcacataa | gagatgttgg | cgctgaaaaa | gggaaatact | atgctctaaa | tgttccacta | 840 |
| aacgatggta | tggacgatga | aagtttccgc | agcttgttta | gacctcttat | ccagaaggtt | 900 |
| atggaagtgt | atcagccaga | ggcagttgtt | cttcagtgtg | gtgctgactc | cttaagtggt | 960 |
| gatcggttgg | gttgcttcaa | cttatcagtc | aagggtcacg | ctgattgcct | tcggttctta | 1020 |
| agatcttaca | acgttcctct | catggtgttg | ggtggtgaag | ggtatactat | tcgaaatgtt | 1080 |
| gcccgttgct | ggtgttatga | gactgcagtt | gctgttggag | tagagccgga | caacaaactc | 1140 |
| ccttacaatg | agtattttga | gtatttcggc | ccagattata | cgcttcatgt | cgacccaagt | 1200 |
| cctatggaga | atttaaacac | gcccaaagat | atggagagga | taaggaacac | gttgctggaa | 1260 |
| caactttcgg | gactaataca | cgcacctagc | gtccagtttc | agcacacacc | accagtcaat | 1320 |
| cgagttttgg | acgagccgga | agatgacatg | gagacaagac | caaaacctcg | catntggagt | 1380 |
| ggaactgcga | cttatgaatc | agacagtgac | gatgatgata | aacctcttca | tggttactca | 1440 |
| tgtcgtggtg | gcgcaactac | ggacagggac | tctaccggtg | aagatgaaat | ggatgacgat | 1500 |
| aacccagagc | cagacgtgaa | tcctccatcg | tcttaaacca | gcttgatggt | ttggtgtctc | 1560 |
| ttttgccata | tgataatgtc | ggcagattta | agaaacaagt | taggggaatg | aatgattctt | 1620 |
| tgatgttttt | tcagcaacct | tttgagttct | gtgaaaacgc | tgcattgatt | agaacagtga | 1680 |
| caactgacta | gtattttggc | ccaagttaga | aaatcagaat | atgtgaaaaa | aaaaaaaaa | 1740 |

-continued aaaaaaaagg cggccgctc tagaggatcc aagcttacgt acgcgtgcat gcgacgtcat    1800

<210> SEQ ID NO 4
<211> LENGTH: 471
<212> TYPE: PRT
<213> ORGANISM: Arabidopsis thaliana
<220> FEATURE:
<221> NAME/KEY: MISC_FEATURE
<222> LOCATION: (418)..(418)
<223> OTHER INFORMATION: "Xaa" is any amino acid

<400> SEQUENCE: 4

```
Met Glu Ala Asp Glu Ser Gly Ile Ser Leu Pro Ser Gly Pro Asp Gly
1               5                   10                  15

Arg Lys Arg Arg Val Ser Tyr Phe Tyr Glu Pro Thr Ile Gly Asp Tyr
            20                  25                  30

Tyr Tyr Gly Gln Gly His Pro Met Lys Pro His Arg Ile Arg Met Ala
        35                  40                  45

His Ser Leu Ile Ile His Tyr His Leu His Arg Arg Leu Glu Ile Ser
    50                  55                  60

Arg Pro Ser Leu Ala Asp Ala Ser Asp Ile Gly Arg Phe His Ser Pro
65                  70                  75                  80

Glu Tyr Val Asp Phe Leu Ala Ser Val Ser Pro Glu Ser Met Gly Asp
                85                  90                  95

Pro Ser Ala Ala Arg Asn Leu Arg Arg Phe Asn Val Gly Glu Asp Cys
            100                 105                 110

Pro Val Phe Asp Gly Leu Phe Asp Phe Cys Arg Ala Ser Ala Gly Gly
        115                 120                 125

Ser Ile Gly Ala Ala Val Lys Leu Asn Arg Gln Asp Ala Asp Ile Ala
    130                 135                 140

Ile Asn Trp Gly Gly Gly Leu His His Ala Lys Lys Ser Glu Ala Ser
145                 150                 155                 160

Gly Phe Cys Tyr Val Asn Asp Ile Val Leu Gly Ile Leu Glu Leu Leu
                165                 170                 175

Lys Met Phe Lys Arg Val Leu Tyr Ile Asp Ile Asp Val His His Gly
            180                 185                 190

Asp Gly Val Glu Glu Ala Phe Tyr Thr Thr Asp Arg Val Met Thr Val
        195                 200                 205

Ser Phe His Lys Phe Gly Asp Phe Phe Pro Gly Thr Gly His Ile Arg
    210                 215                 220

Asp Val Gly Ala Glu Lys Gly Lys Tyr Tyr Ala Leu Asn Val Pro Leu
225                 230                 235                 240

Asn Asp Gly Met Asp Asp Glu Ser Phe Arg Ser Leu Phe Arg Pro Leu
                245                 250                 255

Ile Gln Lys Val Met Glu Val Tyr Gln Pro Glu Ala Val Val Leu Gln
            260                 265                 270

Cys Gly Ala Asp Ser Leu Ser Gly Asp Arg Leu Gly Cys Phe Asn Leu
        275                 280                 285

Ser Val Lys Gly His Ala Asp Cys Leu Arg Phe Leu Arg Ser Tyr Asn
    290                 295                 300

Val Pro Leu Met Val Leu Gly Gly Glu Gly Tyr Thr Ile Arg Asn Val
305                 310                 315                 320

Ala Arg Cys Trp Cys Tyr Glu Thr Ala Val Ala Val Gly Val Glu Pro
                325                 330                 335

Asp Asn Lys Leu Pro Tyr Asn Glu Tyr Phe Glu Tyr Phe Gly Pro Asp
```

-continued

```
                340             345             350
Tyr Thr Leu His Val Asp Pro Ser Pro Met Glu Asn Leu Asn Thr Pro
                    355                 360                 365

Lys Asp Met Glu Arg Ile Arg Asn Thr Leu Leu Glu Gln Leu Ser Gly
370                 375                 380

Leu Ile His Ala Pro Ser Val Gln Phe Gln His Thr Pro Pro Val Asn
385                 390                 395                 400

Arg Val Leu Asp Glu Pro Glu Asp Met Glu Thr Arg Pro Lys Pro
                    405                 410                 415

Arg Xaa Trp Ser Gly Thr Ala Thr Tyr Glu Ser Asp Ser Asp Asp
                420                 425                 430

Asp Lys Pro Leu His Gly Tyr Ser Cys Arg Gly Gly Ala Thr Thr Asp
                    435                 440                 445

Arg Asp Ser Thr Gly Glu Asp Glu Met Asp Asp Asn Pro Glu Pro
                450                 455                 460

Asp Val Asn Pro Pro Ser Ser
465                 470
```

<210> SEQ ID NO 5
<211> LENGTH: 939
<212> TYPE: DNA
<213> ORGANISM: Arabidopsis thaliana

<400> SEQUENCE: 5

```
cacgcgtccg taaaaatcct ctctttttct caaccttgat tcttagccat ggagttctgg      60
ggaattgaag ttaaatcagg aaagccagtt acagtgactc ctgaagaagg cattcttatc     120
cacgtttctc aggcatcgct tggagaatgt aaaaacaaga agggagagtt tgtgccttta     180
catgtaaagg ttgggaacca gaacttggtt ctgggaactc tatcgactga aacatccct     240
cagcttttct gtgatttggt attcgacaag gagtttgagc tttctcacac ttggggaaaa     300
ggaagtgttt actttgttgg atacaaaact cccaacattg agccacaagg ctattctgag     360
gaagaagagg aagaagagga agaagttcct gctgggaatg ctgccaaggc tgtagctaaa     420
ccaaaggcta agcctgcaga gtgaagcca gctgttgatg atgaagagga tgagtctgat     480
tctgacggaa tggatgaaga tgattctgat ggtgaggatt ctgaggaaga agagcctaca     540
cctaagaagc ctgcatcaag caagaagaga gctaatgaaa ctaccctaa agcacctgtg     600
tcagcaaaga aggcgaaagt agcagttact cctcagaaaa cagatgagaa gaagaaaggg     660
ggaaaggctg caaccagag cccaaagtcg gccagtcaag tctcatgtgg ttcatgcaag     720
aagactttca actcagggaa tgcacttgag tctcacaaca aggccaagca cgctgctgcc     780
aagtgaagtg gtttcttatt agagcttgtg atttctatgg aattttgcct gtagtcttta     840
tgaaaccttc ggattttctt atattttctt ttgataacaa gagtcttaat gaaagagagc     900
cagttggagt cttaaaaaaa aaaaaaaaag ggcggccgc                            939
```

<210> SEQ ID NO 6
<211> LENGTH: 245
<212> TYPE: PRT
<213> ORGANISM: Arabidopsis thaliana

<400> SEQUENCE: 6

```
Met Glu Phe Trp Gly Ile Glu Val Lys Ser Gly Lys Pro Val Thr Val
1               5                   10                  15

Thr Pro Glu Glu Gly Ile Leu Ile His Val Ser Gln Ala Ser Leu Gly
            20                  25                  30
```

```
Glu Cys Lys Asn Lys Lys Gly Glu Phe Val Pro Leu His Val Lys Val
            35                  40                  45
Gly Asn Gln Asn Leu Val Leu Gly Thr Leu Ser Thr Glu Asn Ile Pro
 50                  55                  60
Gln Leu Phe Cys Asp Leu Val Phe Asp Lys Glu Phe Glu Leu Ser His
 65                  70                  75                  80
Thr Trp Gly Lys Gly Ser Val Tyr Phe Val Gly Tyr Lys Thr Pro Asn
                 85                  90                  95
Ile Glu Pro Gln Gly Tyr Ser Glu Glu Glu Glu Glu Glu Glu Glu Glu
            100                 105                 110
Val Pro Ala Gly Asn Ala Ala Lys Ala Val Ala Lys Pro Lys Ala Lys
            115                 120                 125
Pro Ala Glu Val Lys Pro Ala Val Asp Asp Glu Glu Asp Glu Ser Asp
130                 135                 140
Ser Asp Gly Met Asp Glu Asp Ser Asp Gly Glu Asp Ser Glu Glu
145                 150                 155                 160
Glu Glu Pro Thr Pro Lys Lys Pro Ala Ser Ser Lys Lys Arg Ala Asn
                165                 170                 175
Glu Thr Thr Pro Lys Ala Pro Val Ser Ala Lys Lys Ala Lys Val Ala
            180                 185                 190
Val Thr Pro Gln Lys Thr Asp Glu Lys Lys Gly Gly Lys Ala Ala
            195                 200                 205
Asn Gln Ser Pro Lys Ser Ala Ser Gln Val Ser Cys Gly Ser Cys Lys
210                 215                 220
Lys Thr Phe Asn Ser Gly Asn Ala Leu Glu Ser His Asn Lys Ala Lys
225                 230                 235                 240
His Ala Ala Ala Lys
            245

<210> SEQ ID NO 7
<211> LENGTH: 1212
<212> TYPE: DNA
<213> ORGANISM: Arabidopsis thaliana

<400> SEQUENCE: 7
gtctttcgct tctaaaaaaa aacctaacaa cctctcttct ctcttcctcg ttcaacaaca     60
atggagttct ggggagttgc ggtgacacca aaaaacgcta ctaaggtgac tcctgaagaa    120
gacagccttg tccacatttc tcaggcttca cttgactgca cagtgaaatc tggagaatct    180
gtggttttga gtgtgactgt tggtggggct aaacttgtta ttggaacact tcacaagac    240
aagttccctc agattagctt tgatttggtt tttgataaag agtttgagct ttcacacagc    300
ggtaccaaag caaatgttca tttcattggc tacaaatccc caacatcga gcaggatgac    360
ttcactagtt cggatgatga ggatgttcct gaagctgttc ctgctcctgc cctactgct    420
gttactgcca acggaaatgc tggagcagct gttgtcaagg ctgacacaaa gccaaaggcc    480
aaacctgccg aagtgaagcc tgcagaagag aagcctgaat cagacgagga agatgagtct    540
gatgatgaag atgagtctga agaggatgat gactctgaga aggaatggga tgttgatgaa    600
gatgactcag atgatgacga ggaggaggat tctgaggatg aagaagagga ggagactcct    660
aagaagcctg agccaatcaa caagaagagg ccaaatgaat ctgtatccaa acacccgtc    720
tctggaaaga aggcaaaacc agcagcagca ccagcttcta ctcctcagaa gacagagaag    780
aagaaaggag gacacaccgc cacaccacac ccagctaaga agggtggaaa gtctcctgtg    840
```

```
aatgctaacc agagccccaa gtctggaggt caatcatccg gtggtaacaa caacaagaag      900
ccattcaact caggcaaaca atttggtggt tccaacaaca agggttctaa caagggcaag      960
ggaaagggta gagcttaagg acgtggatca aggagaggtt ttgggttttc gagtagatga     1020
tgaaaacact tggaagtgtg gttttggatt tttatcttat tttattagta aacttgtta     1080 tcggatgagc tattttgagt atttgcaatt tctactttcc tatgtaattc agtatatgaa     1140
tatttgctga aatgagaaag aagactcgaa ttgcaaacaa aaaaaaaaaa aaaaaaaaa      1200 aagggcggcc gc                                                         1212
```

<210> SEQ ID NO 8
<211> LENGTH: 305
<212> TYPE: PRT
<213> ORGANISM: Arabidopsis thaliana

<400> SEQUENCE: 8

```
Met Glu Phe Trp Gly Val Ala Val Thr Pro Lys Asn Ala Thr Lys Val
1               5                   10                  15

Thr Pro Glu Glu Asp Ser Leu Val His Ile Ser Gln Ala Ser Leu Asp
            20                  25                  30

Cys Thr Val Lys Ser Gly Ser Val Val Leu Ser Val Thr Val Gly
        35                  40                  45

Gly Ala Lys Leu Val Ile Gly Thr Leu Ser Gln Asp Lys Phe Pro Gln
    50                  55                  60

Ile Ser Phe Asp Leu Val Phe Asp Lys Glu Phe Glu Leu Ser His Ser
65                  70                  75                  80

Gly Thr Lys Ala Asn Val His Phe Ile Gly Tyr Lys Ser Pro Asn Ile
                85                  90                  95

Glu Gln Asp Asp Phe Thr Ser Asp Asp Asp Val Pro Glu Ala
            100                 105                 110

Val Pro Ala Pro Ala Pro Thr Ala Val Thr Ala Asn Gly Asn Ala Gly
        115                 120                 125

Ala Ala Val Val Lys Ala Asp Thr Lys Pro Lys Ala Lys Pro Ala Glu
    130                 135                 140

Val Lys Pro Ala Glu Glu Lys Pro Glu Ser Asp Glu Glu Asp Glu Ser
145                 150                 155                 160

Asp Asp Glu Asp Glu Ser Glu Glu Asp Asp Ser Glu Lys Gly Met
                165                 170                 175

Asp Val Asp Glu Asp Asp Ser Asp Asp Asp Glu Glu Glu Asp Ser Glu
            180                 185                 190

Asp Glu Glu Glu Glu Thr Pro Lys Lys Pro Glu Pro Ile Asn Lys
        195                 200                 205

Lys Arg Pro Asn Glu Ser Val Ser Lys Thr Pro Val Ser Gly Lys Lys
    210                 215                 220

Ala Lys Pro Ala Ala Pro Ala Ser Thr Pro Gln Lys Thr Glu Lys
225                 230                 235                 240

Lys Lys Gly Gly His Thr Ala Thr Pro His Pro Ala Lys Lys Gly Gly
                245                 250                 255

Lys Ser Pro Val Asn Ala Asn Gln Ser Pro Lys Ser Gly Gly Gln Ser
            260                 265                 270

Ser Gly Gly Asn Asn Lys Lys Pro Phe Asn Ser Gly Lys Gln Phe
        275                 280                 285

Gly Gly Ser Asn Asn Lys Gly Ser Asn Lys Gly Lys Gly Lys Gly Arg
    290                 295                 300
```

```
Ala
305

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
cggaggactg tcctccgatc ggaggactgt cctccgtgca                              40

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
aattgagctc agccatggag ttctgggg                                          28

<210> SEQ ID NO 11
<211> LENGTH: 29
<212> TYPE: DNA
<213> ORGANISM: Artificial Sequence
<220> FEATURE:
<223> OTHER INFORMATION: primer

<400> SEQUENCE: 11
acgtggatcc agaaaccact tcacttggc                                         29

<210> SEQ ID NO 12
<211> LENGTH: 513
<212> TYPE: PRT
<213> ORGANISM: Zea mays

<400> SEQUENCE: 12

Met Asp Pro Ser Ser Ala Gly Ser Gly Gly Asn Ser Leu Pro Ser Val
  1               5                  10                  15

Gly Pro Asp Gly Gln Lys Arg Arg Val Cys Tyr Phe Tyr Asp Pro Asp
                 20                  25                  30

Val Gly Asn Tyr Tyr Tyr Gly Gln Gly His Pro Met Lys Pro His Arg
             35                  40                  45

Ile Arg Met Thr His Ser Leu Leu Ala Arg Tyr Gly Leu Leu Asn Gln
         50                  55                  60

Met Gln Val Tyr Arg Pro Asn Pro Ala Arg Glu Arg Glu Leu Cys Arg
 65                  70                  75                  80

Phe His Ala Glu Glu Tyr Ile Asn Phe Leu Arg Ser Val Thr Pro Glu
                 85                  90                  95

Thr Gln Gln Asp Gln Ile Arg Leu Leu Lys Arg Phe Asn Val Gly Glu
                100                 105                 110

Glu Cys Pro Val Leu Asp Gly Leu Tyr Ser Phe Cys Gln Thr Tyr Ala
            115                 120                 125

Gly Ala Ser Val Gly Gly Ala Val Lys Phe Asn His Gly His Asp Ile
        130                 135                 140

Ala Ile Asn Trp Ser Gly Gly Leu His His Ala Lys Lys Cys Glu Ala
145                 150                 155                 160

Ser Gly Phe Cys Tyr Val Asn Asp Ile Val Leu Ala Ile Leu Glu Leu
                165                 170                 175
```

```
Leu Lys His His Glu Arg Val Leu Tyr Val Asp Ile Asp Ile His His
        180                 185                 190

Gly Asp Gly Val Glu Ala Phe Tyr Thr Thr Asp Arg Val Met Thr
        195                 200                 205

Val Ser Phe His Lys Phe Gly Asp Tyr Phe Pro Gly Thr Gly Asp Ile
        210                 215                 220

Arg Asp Ile Gly His Ser Lys Gly Lys Tyr Tyr Ser Leu Asn Val Pro
225                 230                 235                 240

Leu Asp Asp Gly Ile Asp Asp Glu Ser Tyr Gln Ser Leu Phe Lys Pro
                245                 250                 255

Ile Met Gly Lys Val Met Glu Val Phe Arg Pro Gly Ala Val Val Leu
            260                 265                 270

Gln Cys Gly Ala Asp Ser Leu Ser Gly Asp Arg Leu Gly Cys Phe Asn
        275                 280                 285

Leu Ser Ile Lys Gly His Ala Glu Cys Val Arg Tyr Met Arg Ser Phe
        290                 295                 300

Asn Val Pro Leu Leu Leu Gly Gly Gly Gly Tyr Thr Ile Arg Asn
305                 310                 315                 320

Val Ala Arg Cys Trp Cys Tyr Glu Thr Gly Val Ala Leu Gly Gln Glu
                325                 330                 335

Pro Glu Asp Lys Met Pro Val Asn Glu Tyr Tyr Glu Tyr Phe Gly Pro
            340                 345                 350

Asp Tyr Thr Leu His Val Ala Pro Ser Asn Met Glu Asn Lys Asn Thr
        355                 360                 365

Arg Gln Gln Leu Asp Asp Ile Arg Ser Lys Leu Ser Lys Leu Arg His
        370                 375                 380

Ala Pro Ser Val His Phe Gln Glu Arg Val Pro Asp Thr Glu Ile Pro
385                 390                 395                 400

Glu Gln Asp Glu Asp Gln Asp Pro Asp Glu Arg His Asp Pro Asp
                405                 410                 415

Ser Asp Met Glu Val Asp His Lys Ala Val Glu Glu Ser Ser Arg
            420                 425                 430

Arg Ser Ile Leu Gly Ile Lys Ile Lys Arg Glu Phe Gly Glu Asn Ala
        435                 440                 445

Thr Arg Val Gln Asp Gly Gly Arg Val Ala Ser Glu His Arg Gly Leu
        450                 455                 460

Glu Pro Met Ala Glu Asp Ile Gly Ser Ser Lys Gln Ala Pro Gln Ala
465                 470                 475                 480

Asp Ala Ser Ala Met Ala Ile Asp Glu Pro Ser Asn Val Lys Asn Glu
                485                 490                 495

Pro Glu Ser Ser Thr Lys Leu Gln Gly Gln Ala Ala Ala Tyr His Lys
            500                 505                 510

Pro

<210> SEQ ID NO 13
<211> LENGTH: 433
<212> TYPE: PRT
<213> ORGANISM: Saccharomyces cerevisiae

<400> SEQUENCE: 13

Met Val Tyr Glu Ala Thr Pro Phe Asp Pro Ile Thr Val Lys Pro Ser
1               5                   10                  15

Asp Lys Arg Arg Val Ala Tyr Phe Tyr Asp Ala Asp Val Gly Asn Tyr
            20                  25                  30
```

-continued

```
Ala Tyr Gly Ala Gly His Pro Met Lys Pro His Arg Ile Arg Met Ala
         35                  40                  45
His Ser Leu Ile Met Asn Tyr Gly Leu Tyr Lys Lys Met Glu Ile Tyr
 50                  55                  60
Arg Ala Lys Pro Ala Thr Lys Gln Glu Met Cys Gln Phe His Thr Asp
 65                  70                  75                  80
Glu Tyr Ile Asp Phe Leu Ser Arg Val Thr Pro Asp Asn Leu Glu Met
                 85                  90                  95
Phe Lys Arg Glu Ser Val Lys Phe Asn Val Gly Asp Cys Pro Val
             100                 105                 110
Phe Asp Gly Leu Tyr Glu Tyr Cys Ser Ile Ser Gly Gly Ser Met
             115                 120                 125
Glu Gly Ala Ala Arg Leu Asn Arg Gly Lys Cys Asp Val Ala Val Asn
130                 135                 140
Tyr Ala Gly Gly Leu His His Ala Lys Lys Ser Glu Ala Ser Gly Phe
145                 150                 155                 160
Cys Tyr Leu Asn Asp Ile Val Leu Gly Ile Ile Glu Leu Leu Arg Tyr
                 165                 170                 175
His Pro Arg Val Leu Tyr Ile Asp Ile Asp Val His Gly Asp Gly
             180                 185                 190
Val Glu Glu Ala Phe Tyr Thr Thr Asp Arg Val Met Thr Cys Ser Phe
             195                 200                 205
His Lys Tyr Gly Glu Phe Phe Pro Gly Thr Gly Glu Leu Arg Asp Ile
             210                 215                 220
Gly Val Gly Ala Gly Lys Asn Tyr Ala Val Asn Val Pro Leu Arg Asp
225                 230                 235                 240
Gly Ile Asp Asp Ala Thr Tyr Arg Ser Val Phe Glu Pro Val Ile Lys
                 245                 250                 255
Lys Ile Met Glu Trp Tyr Gln Pro Ser Ala Val Val Leu Gln Cys Gly
             260                 265                 270
Gly Asp Ser Leu Ser Gly Asp Arg Leu Gly Cys Phe Asn Leu Ser Met
             275                 280                 285
Glu Gly His Ala Asn Cys Val Asn Tyr Val Lys Ser Phe Gly Ile Pro
290                 295                 300
Met Met Val Val Gly Gly Gly Gly Tyr Thr Met Arg Asn Val Ala Arg
305                 310                 315                 320
Thr Trp Cys Phe Glu Thr Gly Leu Leu Asn Asn Val Val Leu Asp Lys
                 325                 330                 335
Asp Leu Pro Tyr Asn Glu Tyr Tyr Glu Tyr Tyr Gly Pro Asp Tyr Lys
             340                 345                 350
Leu Ser Val Arg Pro Ser Asn Met Phe Asn Val Asn Thr Pro Glu Tyr
             355                 360                 365
Leu Asp Lys Val Met Thr Asn Ile Phe Ala Asn Leu Glu Asn Thr Lys
             370                 375                 380
Tyr Ala Pro Ser Val Gln Leu Asn His Thr Pro Arg Asp Ala Glu Asp
385                 390                 395                 400
Leu Gly Asp Val Glu Glu Asp Ser Ala Glu Ala Lys Asp Thr Lys Gly
                 405                 410                 415
Gly Ser Gln Tyr Ala Arg Asp Leu His Val Glu His Asp Asn Glu Phe
             420                 425                 430
Tyr
```

```
<210> SEQ ID NO 14
<211> LENGTH: 307
<212> TYPE: PRT
<213> ORGANISM: Zea mays

<400> SEQUENCE: 14

Met Glu Phe Trp Gly Leu Glu Val Lys Pro Gly Ser Thr Val Lys Cys
1               5                   10                  15

Glu Pro Gly Tyr Gly Phe Val Leu His Leu Ser Gln Ala Ala Leu Gly
            20                  25                  30

Glu Ser Lys Lys Ser Asp Asn Ala Leu Met Tyr Val Lys Ile Asp Asp
        35                  40                  45

Gln Lys Leu Ala Ile Gly Thr Leu Ser Val Asp Lys Asn Pro His Ile
    50                  55                  60

Gln Phe Asp Leu Ile Phe Asp Lys Glu Phe Glu Leu Ser His Thr Ser
65                  70                  75                  80

Lys Thr Thr Ser Val Phe Phe Thr Gly Tyr Lys Val Glu Gln Pro Phe
                85                  90                  95

Glu Glu Asp Glu Met Asp Leu Asp Ser Glu Asp Glu Asp Glu Glu Leu
            100                 105                 110

Asn Val Pro Val Val Lys Glu Asn Gly Lys Ala Asp Glu Lys Lys Gln
        115                 120                 125

Lys Ser Gln Glu Lys Ala Val Ala Ala Pro Ser Lys Ser Ser Pro Asp
    130                 135                 140

Ser Lys Lys Ser Lys Asp Asp Asp Ser Asp Glu Asp Glu Thr Asp
145                 150                 155                 160

Asp Ser Asp Glu Asp Glu Thr Asp Asp Ser Asp Glu Gly Leu Ser Ser
            165                 170                 175

Glu Glu Gly Asp Asp Asp Ser Ser Asp Glu Asp Asp Thr Ser Asp Asp
        180                 185                 190

Glu Glu Glu Asp Thr Pro Thr Pro Lys Lys Pro Glu Val Gly Lys Lys
    195                 200                 205

Arg Pro Ala Glu Ser Ser Val Leu Lys Thr Pro Leu Ser Asp Lys Lys
210                 215                 220

Ala Lys Val Ala Thr Pro Ser Ser Gln Lys Thr Gly Gly Lys Lys Gly
225                 230                 235                 240

Ala Ala Val His Val Ala Thr Pro His Pro Ala Lys Gly Lys Thr Ile
                245                 250                 255

Val Asn Asn Asp Lys Ser Val Lys Ser Pro Lys Ser Ala Pro Lys Ser
            260                 265                 270

Gly Gly Ser Val Pro Cys Lys Pro Cys Ser Lys Ser Phe Ile Ser Glu
        275                 280                 285

Thr Ala Leu Gln Ala His Ser Arg Ala Lys Met Gly Ala Ser Glu Ser
    290                 295                 300

Gln Val Gln
305
```

REPRESSING GENE EXPRESSION IN PLANTS

This is a Continuation-in-Part of application Ser. No. 09/383,971 (now abandoned), filed Aug. 27, 1999. The entire disclosure of the prior application is hereby incorporated by reference in its entirety.

The present invention relates to repression of gene expression. More specifically the invention relates to repression of -ene expression in plants by histone deacetylase, and histone deacetylase enzyme homologs.

BACKGROUND OF THE INVENTION

Posttranslational modifications of histones in chromatin are important mechanisms in the regulation of gene expression. Acetylation of core histones is correlated with transcriptionally active chromatin of eukaryotic cells. Acetylation is thought to weaken the interactions of histones with DNA and induce alterations in nucleosome structure. These alterations enhance the accessibility of promoters to components of the transcription machinery, and increase transcription.

Histone deacetylation is thought to lead to a less accessible chromatin conformation, resulting in the repression of transcription (e.g. Pazin and Kadonaga, 1997; Struhl, 1998). The role of the yeast histone deacetylase, RPD3, in transcriptional repression was first discovered through a genetic screen for transcriptional repressors in *S. cerevisiae* (Vidal and Gaber, 1991). Since then, a number of yeast and mammalian histone deacetylase genes have been cloned (Rundlett et al., 1996; Emiliani et al., 1998; Hassig et al., 1998; Verdel and Khochbin, 1999). Most eukaryotic histone deacetylases show some sequence homology to yeast RPD3, suggesting that these proteins are all members derived from a single gene family (Khochbin and Wolffe, 1997; Verdel and Khochbin, 1999). In yeast and mammalian cells, the RPD3 histone deacetylases mediate transcriptional repression by interacting with specific DNA-binding proteins or associated corepressors and by recruitment to target promoters (Alland et al., 1997; Kadosh and Struhl, 1997; Hassig et al., 1997; Nagy et al., 1997; Gelmetti et al., 1998). Recently, a second family of histone deacetylases, HDA1 and related proteins, were identified in yeast and mammalian cells (Rundlett et al., 1996; Fischle et al., 1999; Verdel and Khochbin, 1999). The deacetylase domain of HDA 1-related proteins is homologous to but significantly different from that of RPD3 (Fischle et al. 1999; Verdel and Khochbin, 1999). These proteins also appear to be functionally different from RPD-like proteins in yeast cells (Rundlett et al., 1996). WO 97/35990 discloses mammalian-derived histone deacetylase (HD) gene sequences, gene products, and uses for these sequences and products. There is no disclosure of the use of these gene products for repressing gene expression.

In plants, an RPD3 homolog was first discovered in maize and it complemented the phenotype of a rpd3 null mutant of the yeast *S. cerevisiae* (Rossi et al, 1998). HD2 was also identified from maize that shows no sequence homology to yeast RPD3 or RPD3-related proteins (Lusser et al., 1997).

Even though histone deacetylation is thought to lead to repression of transcription, this has never been tested in plant systems. WO 98/48825 discloses the use of histone deacetylase (HD) for repressing gene expression in mammalian cell culture, however, the use of HD, or modified HD in plant gene repression is not disclosed. There is a plethora of information relating to the up-regulation of gene expression in plants, however, little is known on systems that can down regulate gene-expression. Thus, there is a need to develop regulatory systems for selectively repressing gene expression in plants.

The present invention pertains to novel histone deacetylase enzymes obtained from a plant. Four novel genes encoding histone deacetylases (AtRPD3A, AtRPD3B, AtHD2A and AtHD2B) and fragments thereof, were shown to be involved in the regulation of gene transcription within plants.

It is an object of the invention to overcome disadvantages of the prior art.

The above object is met by the combination of features of the main claims, the sub-claims disclose further advantageous embodiments of the invention.

SUMMARY OF THE INVENTION

The present invention relates to repression of gene expression by histone deacetylase enzymes. More specifically the invention relates to repression of gene expression in plants by histone deacetylase enzymes.

According to the present invention there is provided a method of regulating gene expression in a transgenic plant comprising, introducing into a plant:

i) a first chimeric nucleotide sequence comprising a first regulatory element in operative association with a coding sequence of interest, and a controlling sequence; and ii) a second chimeric nucleotide sequence comprising a second regulatory clement in operative association with a nucleotide sequence encoding histone deaceytlase and a nucleotide sequence encoding a DNA binding protein, the DNA binding protein having an affinity for the controlling sequence, to produce the transgenic plant, and growing the transgenic plant.

The present invention is directed to the above method wherein the step of introducing comprises transforming the plant with the first, and the second, chimeric nucleotide sequence. Furthermore, the step of introducing comprises transforming a first plant with the first chimeric nucleotide sequence, and transforming a second plant with the second chimeric nucleotide sequence, followed by a step of crossing the first and the second plant, to produce the transgenic plant. Also included is the above method, wherein the step of introducing comprises transforming a plant with the first chimeric nucleotide sequence, followed by transforming the same plant with the second chimeric nucleotide sequence, or co-transforming a plant with both the first and second chimeric nucleotide sequences.

The present invention embraces the method as described above wherein the histone deacetylase, within the step of introducing, is selected from the group consisting of AtRPD3A, AtRPD3B, AtHD2A AtHD2B, an analogue, fragment, or derivative of AtRPD3A, AtRPD3B, AtHD2A AtHD2B, and a nucleotide sequence that hybridizes to AtRPD3A, AtRPD3B, AtHD2A AtHD2B at 65° C. in 0.5 M $Na_2HPO_4$ (pH 7.2), 7% SDS, and 1 mM EDTA, wherein the analog, fragment, derivative, or nucleotide sequence that hybridizes encodes a product that exhibits repression of gene expression activity.

The present invention also relates to the method as described above wherein the upstream activating sequence and the DNA binding protein, within the step of introducing, are a Gal14 upstream activating sequence and a GAL4-binding protein, respectively. Furthermore, the first and the second regulatory region are selected from the group consisting of constitutive, tissue specific, developmentally-regulated, and inducible regulatory elements.

This invention is also directed to an isolated nucleotide sequence, selected from the group consisting of:

i) SEQ ID NO.:1, SEQ ID NO:3, SEQ ID NO:5, SEQ ID NO:7;

ii) an analog, derivative, fragment of SEQ ID NO:1, SEQ ID NO:3, SEQ ID NO:5, SEQ ID NO:7; and iii) a nucleotide sequence that hybridizes to SEQ ID NO:1, SEQ ED NO:3, SEQ ID NO:5, SEQ ID NO:7 at 65° C. in 0.5 M $Na_2HPO_4$ (pH 7.2), 7% SDS, and 1 mM EDTA, wherein the analog, derivative, fragment or the nucleotide sequence that hybridizes encodes a product that exhibits repression of gene expression activity. Furthermore, according to the present invention, there is also provided a chimeric construct comprising a regulatory element in operative association with the isolated nucleotide sequence as defined above, as well as a vector comprising the chimeric construct.

The present invention also pertains to an isolated amino acid sequence, selected from the group consisting of:

i) SEQ ID NO:2, SEQ ID NO:4, SEQ ID NO:6, SEQ ID NO:8; and ii) an analog, derivative, fragment of SEQ ID NO:2, SEQ ID NO:4, SEQ ID NO:6, SEQ ID NO:8, wherein the analog, derivative, or fragment exhibits repression of gene expression activity.

The present invention includes a transgenic plant, a transgenic plant cell, a transgenic seed, comprising said isolated nucleotide sequence as defined above.

The present invention is directed to a method of regulating Gene expression in a plant comprising:

i) introducing into the plant a chimeric nucleotide sequence comprising a regulatory element in operative association with a nucleotide sequence encoding, histone deaceytlase and a nucleotide sequence encoding a DNA binding protein, to produce a transgenic plant; and ii) crowing the transgenic plant, wherein the DNA binding protein has an affinity for a native controlling sequence within the plant.

The present invention also provides a method for altering a biochemical, physiological or developmental pathway of an organism comprising:

i) introducing into an organism a chimeric nucleotide sequence comprising a regulatory element in operative association with a nucleotide sequence encoding histone deaceytlase and a nucleotide sequence encoding a DNA binding protein specific for a controlling sequence; and ii) growing the organism.

The present invention includes a method for identifying a DNA binding protein comprising:

i) introducing into a plant a chimeric nucleotide sequence comprising a regulatory element in operative association with a nucleotide sequence encoding histone deaceytlase fused with a nucleotide sequence of interest and of unknown function, to produce a transgenic plant;

ii) growing the transgenic plant; and iii) examining the transgenic plant to determine whether the chimeric nucleotide sequence comprising the nucleotide sequence of interest has an effect on plant phenotype.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows the nucleotide and predicted amino acid sequences of several HD's of the present invention. FIG. 1(A) shows the nucleotide and amino acid of AtRPD3A (SEQ ID NO's:1 and 2, respectively). FIG. 1(B) shows the nucleotide and amino acid sequence of AtRPD3B (SEQ ID NO's:3 and 4, respectively).

FIG. 2 shows nucleotide and predicted amino acid sequences of several more HD's of the present invention. FIG. 2(A) shows the nucleotide and amino acid of AtHD2A (SEQ ID NO's:5 and 6, respectively). FIG. 2(B) shows the nucleotide and amino acid of AtHD2B (SEQ ID NO's: 7 and 8, respectively).

FIG. 3 displays the amino acid sequence alignment of the AtRPD3A (SEQ ID NO:2), AtRPD3B (SEQ ID NO:4), maize RPD3 (ZmRPD3; SEQ ID NO:12) and yeast RPD3 (SEQ ID NO:13). Identical amino acids are shaded in black. The amino acids with asterisks represent residues with potential roles in deacetylase activity.

FIG. 4 displays the amino acid sequence alignment of AtHD2A (SEQ ID NO:6), AtHD2B (SEQ ID NO:8) and maize HD2 (ZmHD2; SEQ ID NO:14). Identical amino acids are shaded in black. The amino acids with asterisks are the predicted histone deacetylase catalytic residues. The extended acidic domains are underlined.

FIG. 9 shows a schematic of the effector and reporter plasmids comprising AtRPD3A, and the repression of the $UAS_{GAL4}$-BtCUP-GUS fusion gene by AtRPD3A protein in transient expression assays. FIG. 9(A) shows aschematic diagram of the effector and reporter constructs used in co-bombardment experiments. The effector constructs contained the tCUP promoter fused to the AtRPD3A coding region which was fused to the DNA binding domain of GAL4 (GAL4BD) and the polyadenylation signal of nopaline synthelase gene:(Nos-T). The reporter construct (UAS$_{GAL4}$-BtCUP-GUS) contained the upstream activating sequence of GAL4 protein tandemly repeated two times (UAS$_{GAL4}$) fused to the -394tCUP promoter-GUS construct. FIG. 9(B) shows repression of the UAS$_{GAL4}$-BtCUP-GUS fusion gene by AtRPD3A protein. The reporter gene was co-bombarded with each effector plasmid or a control plasmid pUC19 as a control treatment. GUS activity was reported as picomoles of 4-methylumbelliferone per milligram of protein per minute. Bars indicate the standard error of three replicates.

FIG. 10 shows the repression of the UAS$_{GAL4}$-BtCUP-GUS fusion gene by AtHD2A protein in transient expression assays. FIG. 10(A) shows a schematic diagram of the effector and reporter constructs used in cobombardment experiments. The reporter construct contains the upstream activating sequence of GAL4 tandem repeated two times (UAS$_{GAL4}$×2) and fused to the -394-tCUP promoter-GUS construct. The effector constructs contain the GAL4 DNA binding domain (amino acids 1–147) fused to the full-length AtHD2A (AtHD2A, 1–245) or a series deletions of AtHD2A. HDAC refers to the predicted histone deacetylase catalytic domain. Acidic R refers to the extended acidic amino acid domain and C2H2 refers to the putative zinc finger. FIG. 10(B) shows repression of the UAS$_{GAL4}$-BtCUP-GUS fusion gene by AtHD2A and its deletions. The reporter gene was cobombarded with each effector plasmid, or control plasmid pUS19 as control treatments. GUS activity was reported as picomoles of4-methylumbelliferone per milligram of protein per minute. Bars indicate the standard error of three replicates.

FIG. 11 displays the structure of the plasmids used for Arabidopsis transformation of AtRPD3A. FIG. 11(A) shows full-length AtRPD3A cDNA in which the positions of SacI and SspI restriction sites are indicated. FIG. 11(B) shows antisense construct in which the 519 bp fragment of the truncated AtRPD3A cDNA in an antisense orientation was driven by the -394-tCUP promoter. Nos-T refers to the polyadenylation signal of the nopaline synthetase gene.

FIG. 16 displays scanning electron micrographs of siliques. FIG. 16(A) shows siliques formed on the wild-type plant. FIG. 16(B) shows siliques formed on an antisense AtHD2A transgenic plant.

FIG. 17 shows an outline of an experiment to demonstrate repression of expression of a gene in a tissue-specific manner. FIG. 17(A) outlines a binary transrepression system involving the use of a tissue-specific regulatory element and constructs shown in FIG. 17(B). A reporter gene (expression construct) under the control of a constitutive promoter is active when introduced into a reporter plant. Effector genes, under control of tissue specific regulatory regions are introduced into effector plants. Transgene repression is achieved by crossing reporter plant lines with effector lines that express a repressor (e.g. histone deacetylase), and a controlling sequence binding domain that specifically recognizes a control sequences of the reporter gene. The pattern of reporter gene repression will reflect the pattern of repressor expression, allowing a coding sequence of interest to be repressed under a variety of regimes by crossing to an appropriate effector line. The upper lob of the schematic plant represents the fruiting body of the plant, for example the seeds, while the horizontal lobes represent leaves. Black areas represent tissues exhibiting reporter gene expression, while grey and white areas represent no reporter gene expression. Grey regions indicate expression of the HD/CS-BD (effector) constructs, for example, either NAP1-GAL4/HD, or tCUP-GAl4/HD. FIG. 17(B) shows a schematic of the plasmids used for repressing transgene expression in transgenic plants. The effector constructs contained the tCUP promoter (Effector 1) or napin promoter (NAP; Effector 2)) fused to the fusion of the GAL4BD with the AtHD2A coding region and the polyadenylation signal of nopaline synthetase gene (Nos-T). The reporter constructs (GAL4$_{UAS}$-tCUP-GUS and GAL4$_{UAS}$-35S-GUS) contained the upstream activating sequence of GAL4 protein tandem repeated two times (GAL4$_{UAS}$) fused to the -394-tCUP or 35S promoter-GUS constructs.

FIG. 18(A) Histochemical analysis of GUS expression in the seedlings, flowers and seeds of the reporter line UAS$_{GAL4}$-tCUP-GUS. FIG. 18 (B). GUS expression is repressed in the seedlings, flowers and seeds of the crossing tCUP-GAL4/AtHD2A X UAS$_{GAL4}$-tCUP-GUS F1 progeny. FIG. 18(C). GUS expression is specifically repressed in the seeds of the crossing: NAP1-GAL4/AtHD2A X UAS$_{GAL4}$-tCUP-GUS F1 progeny.

FIG. 19 shows GUS expression in the plants following crossing reporter lines and effector lines progeny as outlined in FIG. 17, or sequential transformation of plants with reporter and effector constructs.

AtHD2A (NAP1-GAL4A:tCUP-GUS). Control 3, plants transformed with 35S-GAL4/AtHD2A only. Three plants were assayed for each treatment.

Figure 20:
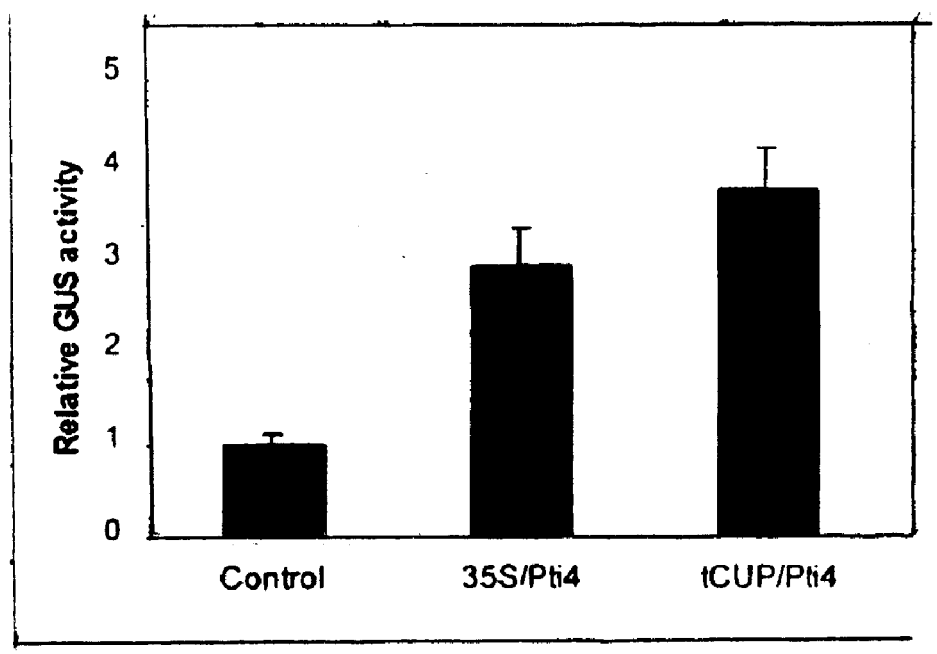

FIG. 20 shows activation of the GCC box-mediated transcription of GUS reporter gene by Pti4 protein in transient expression assays. FIG. 20(A) outlines a schematic diagram of the effector and reporter constructs used in co-bombardment experiments. The reporter construct contains two GCC-boxes fused to the -62tCUP minimal promoter-GUS construct. The effector constructs contain the Pti4 cDNA fused to the Nos terminator driven by the 35S or tCUP promoter. FIG. 20(B) shows activation of the GCC/GUS fusion gene by Pti4. The reporter plasmid, GCC/GUS, was co-bombarded with each effector plasmid or the control plasmid pUC19. GUS activity was reported as picomoles of 4-methylumbelliferone per milligram of protein per minute. Bars indicate the standard error of three replicates.

Figure 21:
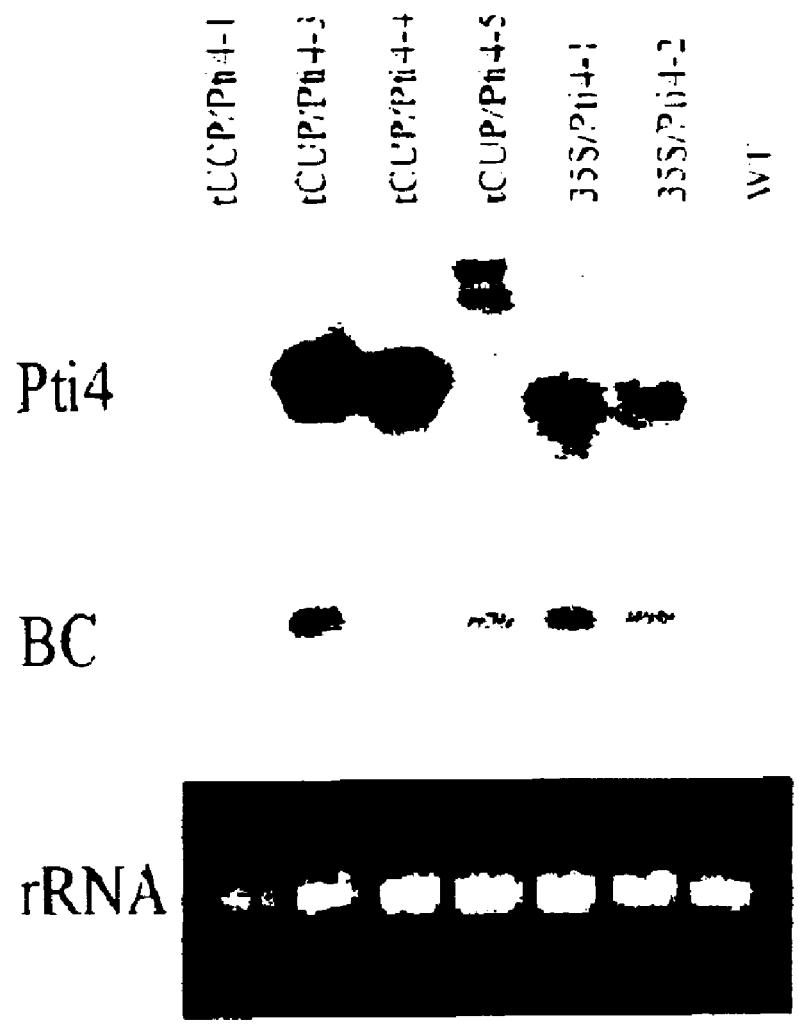

FIG. 21 shows Northern blot analysis of the Pti4 transgenic plants. Total RNA was isolated from wild-type (WT) and transgenic lines (1–6). Lanes 1 to 6 correspond to transgenic lines tCUP/Pti4-1, tCUP/Pti4-3, tCUP/Pti4-4, tCUP/Pti4-5, 35S/Pti4-1, and 35S/Pti4-2, respectively. Five micrograms of total RNA were probed with a Pti4 cDNA probe and a basic chitinase (BC) probe. Photographs of the 25S rRNA bands on the ethidium-bromide-stained gel are shown as a measure of approximately equal loading of the gels.

Figure 22:
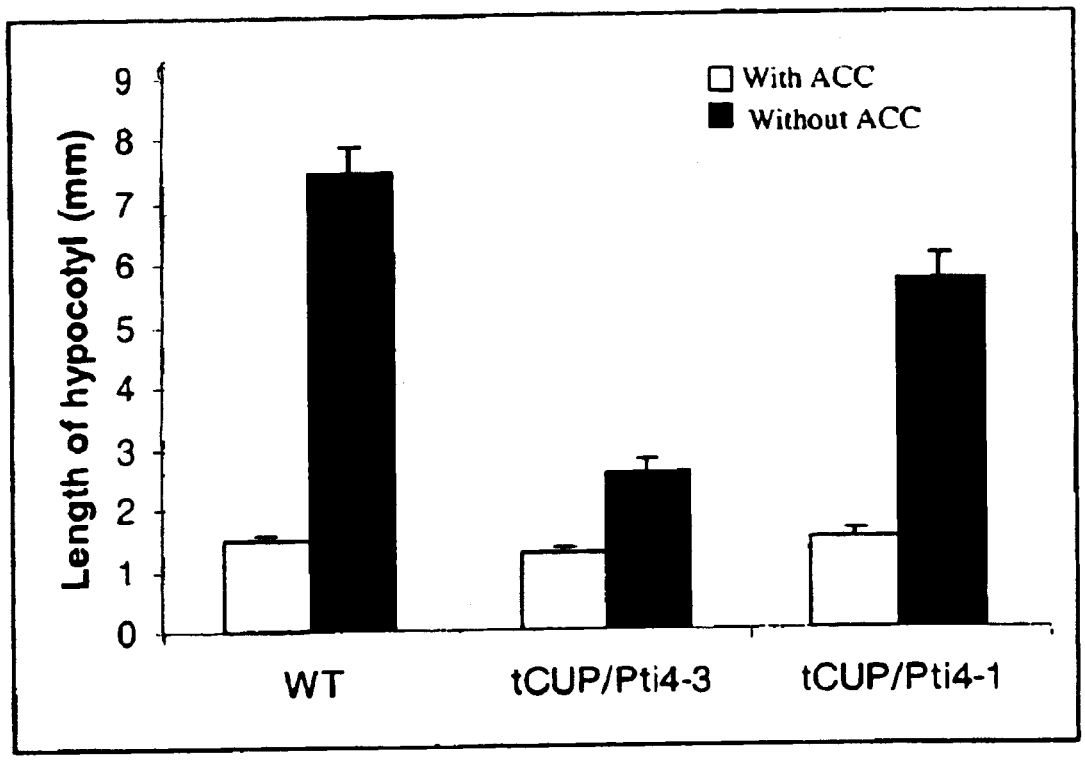

FIG. 22 shows length of hypocotyl of transgenic Arabidopsis seedlings. Surface-sterilized seeds from wild-type (WT) and transgenic lines (tCUP/Pti4-3 and tCUP/Pti4-1) were planted in growth medium and cold treated at 4° C. for 4 days before germination and growth in the dark at 23° C. for 72 hr in the presence (with ACC) or absence (without ACC) of 1-aminocyclopropane-1-carboxylic acid. The lengths of seedling hypocotyls were measured to the closest millimeter. 14 to 20 seedlings from each line were measured. Error bars correspond to the standard error.

Figure 23:
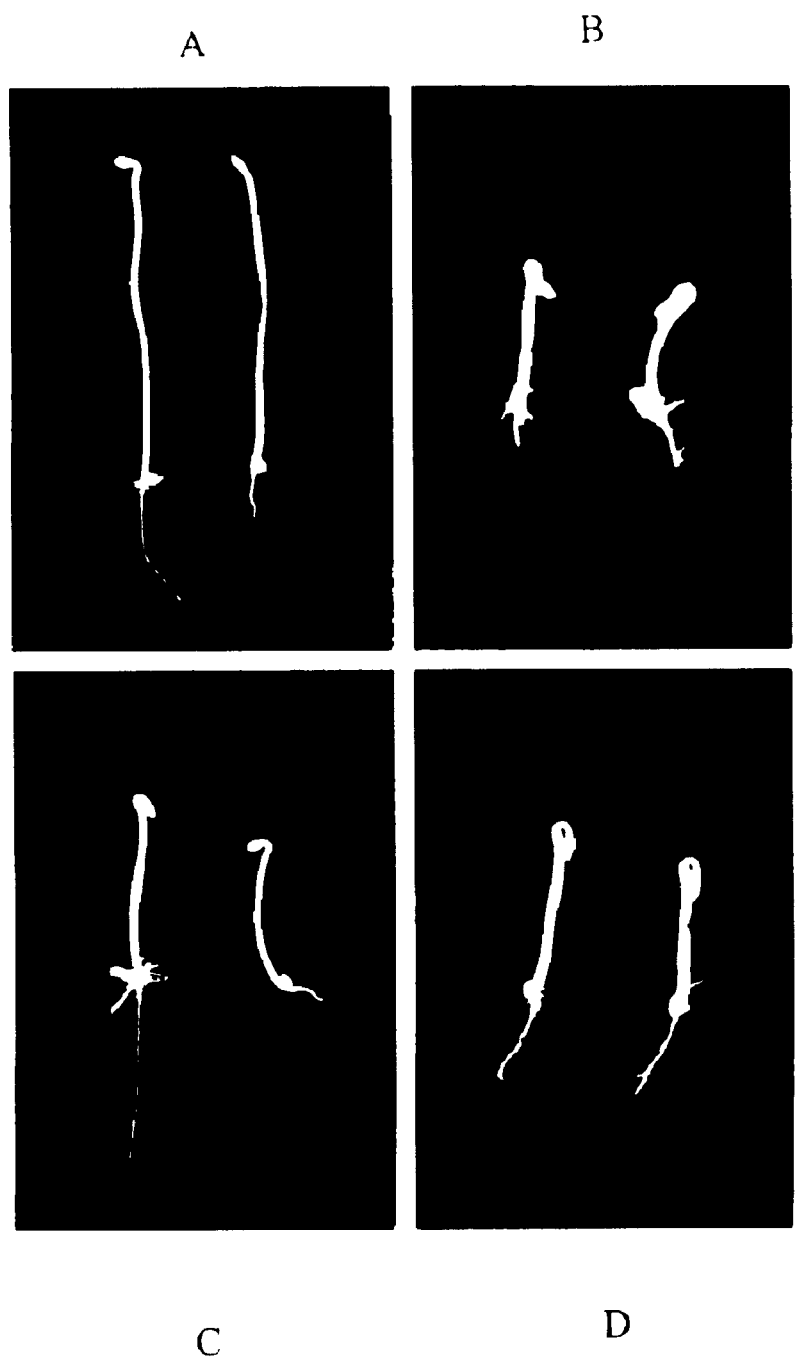

FIG. 23 Phenotype of Pti4 overexpression in transgenic seedlings. Each panel is composed of two etiolated Arabidopsis seedling. Surface-sterilized seeds were planted in growth medium and cold treated at 4° C. for 4 days before germination and growth in the dark at 23° C. for 72 hr. FIG. 23(A) Wild-type incubated without aminocyclopropane carboxylic acid (ACC); FIG. 23(B) Wild-type displaying the triple response in the presence of 10 µM ACC; FIG. 23(C) tCUP/Pti4-3 transgenic seedlings incubated without ACC; FIG. 23(D) tCUP/Pti4-3 transgenic seedlings incubated in the presence of 10 µM ACC.

Figure 24:
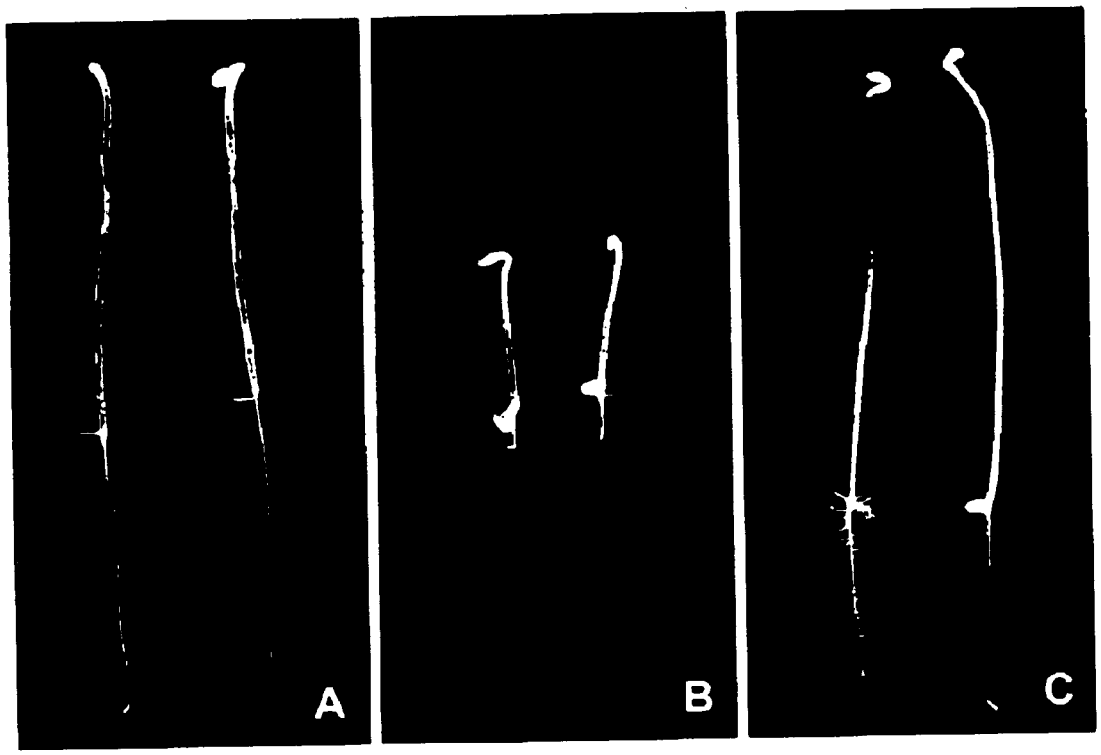

FIG. 24 shows the phenotype of Pti4-AtHD2A overexpression in transgenic seedlings. Each panel is composed of two etiolated Arabidopsis seedling. Surface-sterilized seeds were planted in growth medium and cold treated at 4° C. for 4 days before germination and growth in the dark at 23° C. for 72 hr. FIG. 24(A) shows the wild-type. FIG. 24(B) shows tCUP/Pti4-3 plants. FIG. 24(C) shows tCUP/Pti4-AtHD2A seedlings. The photos were taken after plants were grown for 5 weeks in a growth chamber (16 hr of light and 8 hr of darkness at 23° C.).

DESCRIPTION OF PREFERRED EMBODIMENT

The present invention relates to repression of gene expression by histone deacetylase enzymes. More specifically the invention relates to repression of gene expression in plants by histone deacetylase enzymes, and histone deacetylase enzyme homologs.

The following description is of a preferred embodiment by way of example only and without limitation to the combination of features necessary for carrying the invention into effect.

Histone deacetylases (HD) can be grouped into three families: (1) *S. cerevisiae* RPD3 and RPD3-related proteins (Rundlett et al., 1996; Emilliani et al., 1998); (2) *S. cerevisiae* HDA1 and related proteins (Fischle et al., 1999; Verdel and Khochibin, 1999) and; (3) Zea mays HD2 and related proteins (Lusser et al., 1997). Sequence analysis performed on these proteins showed that most of them display conserved features. For example, RPD3 related proteins maintain a highly-homologous N-terminal domain and a more variable short C-terminal region (Khochbin and Wolffe, 1997). The RPD3 homology domain is also shared by several prokaryotic proteins interacting with various acetylated substrates (Leipe and Landsman, 1997; Ladomery et al.,1997). Mutagenesis analysis of this homology domain confirmed that this domain is inextricably linked to its deacetylase enzymatic activity (Hassig et al., 1998; Kadosh and Struhl, 1998). The second family of histone deacetylases, comprising HDA1 and related-proteins also maintain a highly homologous deacetylase domain, but the domain is significantly different from that of RPD3 and RPD3-like proteins. Similarly, HD2 and HD2-like proteins show no sequence homology to RPD3-like and HDA1-like families of histone deacetylases.

As described in more detail below, a plant EST database was screened using yeast RPD3 or maize HD2. Two EST clones were identified corresponding to the yeast RPD3 sequence and two clones were identified corresponding to the maize HD2 sequence (FIG. 1 and 2). These clones were termed AtRPD3A (SEQ ID NO:1), AtRPD3B (SEQ ID NO:3)., AtHD2A (SEQ ID NO:5) and AtHD2B (SEQ ID NO:7), respectively.

The expression of AtRPD3A and AtRPD3B transcripts, determined by Northern hybridization (FIGS. 7 and 8) revealed that AtRPD3A RNA accumulated to relatively high levels in the leaves, stems, flowers and young siliques. The pattern of AtHD2A and AtHD2B RNA expression indicated that AtHD2A RNA accumulated in the flowers and young siliques, while AtHD2B RNA, accumulated the stem, flowers and young siliques and to a somewhat lower level in the leaves.

The HD's of the present invention, and those of the prior art, may be used to repress the expression of a coding sequence of interest within a plant by targeting a desired HD to a nucleotide sequence containing the coding sequence of interest. While not wishing to be bound by theory, the repression of gene expression activity via locally altering chromatin structure is made possible by targeting a HD to a nucleotide sequence within the vicinity of a coding sequence of interest. The localized deacetylation of histones may result in the observed repression of transcription as described herein. By "histone deacetylase" (HD) it is meant any HD as known within the art. These include the HD's as described of the present invention as well as other plant, animal or microbial HD's. Furthermore, by "repression of gene expression activity" it is meant the reduction in the level of mRNA, protein, or both mRNA and protein, encoded by the coding sequence of interest. Repression of gene expression activity may result from the down regulation of transcription.

By "regulatory region" or "regulatory element" it is meant a portion of nucleic acid typically, but not always, upstream of a gene, which may be comprised of either DNA or RNA, or both DNA and RNA. A regulatory element may be capable of mediating organ specificity, or controlling developmental or temporal gene activation. A "regulatory element" includes promoter elements, basal (core) promoter elements, elements that are inducible in response to an external stimulus, elements that mediate promoter activity such as negative regulatory elements or transcriptional enhancers. "Regulatory element", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region. In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. A promoter element comprises a basal promoter element, responsible for the initiation of transcription, as well as other regulatory elements (as listed above) that modify gene expression.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well.

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods. Inducible elements may be derived from either plant or non-plant genes (e.g. Gatz, C. and Lenk, I. R. P., 1998, Trends Plant Sci. 3, 352–358; which is incorporated by reference). Examples, of potential inducible promoters include, but not limited to, teracycline-inducible promoter (Gatz, C.,1997, Ann. Rev. Plant Physiol. Plant Mol. Biol. 48, 89–108; which is incorporated by reference), steroid inducible promoter (Aoyama, T. and Chua, N. H., 1997, Plant J. 2, 397404; which is incorporated by reference) and ethanol-inducible promoter (Salter, M. G., et al, 1998, Plant Journal 16, 127–132; Caddick, M. X., et al,1998, Nature Biotech. 16, 177–180, which are incorporated by reference) cytokinin inducible IB6 and CK11 genes (Brandstatter, I. and Kieber, J. J.,1998, Plant Cell 10, 1009–1019; Kakimoto, T., 1996, Science 274, 982–985; which are incorporated by reference) and the auxin inducible element, DR5 (Ulmasov, T., et al., 1997, Plant Cell 9. 1963–1971; which is incorporated by reference).

A constitutive regulatory element directs the expression of a gene throughout the various parts of a plant and continuously throughout plant development. Examples of known constitutive regulatory elements include promoters associated with the CaMV 35S transcript. (Odell et al., 1985, Nature, 313: 810–812), the rice actin 1 (Zhang et al, 1991, Plant Cell, 3: 1155–1165) and triosephosphate isomerase 1 (Xu et al, 1994, Plant Physiol. 106: 459–467) genes, the maize ubiquitin 1 gene (Comejo et al, 1993, Plant. Mol. Biol. 29: 637–646), the Arabidopsis ubiquitin 1 and 6 genes (Holtorf et al, 1995, Plant Mol. Biol. 29: 637–646), and the tobacco translational initiation factor 4A gene (Mandel et al, 1995 Plant Mol. Biol. 29: 995–1004). The term "constitutive" as used herein does not necessarily indicate that a gene under control of the constitutive regulatory element is expressed at the same level in all cell types, but that the gene is expressed in a wide range of cell types even though variation in abundance is often observed.

An "analogue" includes any substitution, deletion, or additions to the sequence of the HD of the present invention provided that the analogue maintains at least one property associated with the activity of HD as described herein. One such property includes repressing gene expression.

The DNA sequences of the present invention include the DNA sequences of SEQ ID NO: 1, 3, 5 and 7 and fragments thereof, as well as analogues of, or nucleic acid sequences comprising about 80% similarity with the nucleic acids as defined in SEQ ID NO's: 1, 3, 5 and 7. Analogues (as defined above), include those DNA sequences which hybridize under stringent hybridization conditions (see Maniatis et al., in Molecular Cloning (A Laboratory Manual), Cold Spring Harbor Laboratory, 1982, p. 387–389) to any one of the DNA sequence of SEQ ID NO: 1, 3, 5 or 7 provided that said sequences maintain at least one property of the activity of the HD as defined herein.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 4×SSC at 42° C. Analogues also include those DNA sequences which hybridize to any one of the sequences of SEQ ID NO: 1, 3, 5 or 7 under relaxed hybridization conditions, provided that said sequences maintain at least one regulatory property of the activity of the regulatory element. Examples of such non-hybridization conditions includes hybridization in 4×SSC at 50° C. or with 30–40% formamide at 42° C. Another set of hybridization conditions include: 65° C. in 0.5 M $Na_2HPO_4$ (pH 7.2), 7% SDS, and 1 mM EDTA, followed by washing for 15 min in 2×SSC with 0.1% SDS at room temperature, then twice for 20 min in 0.1×SSC, 0.1% SDS at 65° C.

The present invention is further directed to one or more chimeric gene constructs comprising a coding sequence of interest operatively linked to a regulatory element. Any exogenous coding sequence can be used as a coding sequence of interest and manipulated according to the present invention to result in the regulated expression of the exogenous coding sequence.

The one or more chimeric gene constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

One or more of the chimeric gene constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

To aid in identification of transformed plant cells, the constructs of this invention may be further manipulated to include plant selectable markers. Useful selectable markers include enzymes which provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (β-glucuronidase), or luminescence, such as luciferase are useful.

Also considered part of this invention are transgenic plants containing the chimeric gene construct of the present invention. However, it is to be understood that the chimeric gene constructs of the present invention may also be combined with a coding sequence of interest for expression within a range of plant hosts.

By "coding sequence of interest" it is meant any nucleotide sequence that encodes a protein and that is to be expressed within a host organism. Such a coding sequence of interest may include, but is not limited to, a coding sequence whose product has an effect on plant growth or yield, for example a plant growth regulator such as an auxin or cytokinin and their analogues, or a coding sequence of interest may comprise a herbicide or a pesticide resistance gene, which are well known within the an. A coding sequence of interest may also include a nucleotide sequence that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-τ, blood clotting factors, for example, Factor VIII, Factor IX, or tPA or combinations thereof. A coding sequence of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures (for example, Clough and Bent, 1998)

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561–579 (1997); Clough and Bent (1998)). The present invention further includes a suitable vector comprising the chimeric gene construct.

The present invention relates to chimeric constructs and a method for regulating the expression of a coding sequence of interest through the use of at least one HD. The chimeric constructs include:

a first chimeric construct (the expression construct) comprising a first regulatory element, a controlling sequence (CS), a coding sequence of interest, and a terminator. The first regulatory element may permit the constitutive, developmental or temporal expression of the coding sequence of interest within a plant; and a second chimeric construct (the effector construct), comprising a second regulatory element, a nucleotide sequence encoding a CS binding domain (CS-BD), and HD, and a terminator sequence. The second regulatory element may permit the constitutive, developmental, temporal or induced expression of the HD within a plant.

The method includes introducing the first and second chimeric constructs as described above, within a plant in order to obtain controlled expression of the coding sequence of interest. The introduction of the two chimeric constructs within a plant may take place using techniques well known within the art such as transformation wherein both chimeric constructs are introduced into the same plant, or through mating plants that each comprise one of the desired constructs in order to obtain a plant that expresses both chimeric constructs.

The CS and CS-BD are characterized in that they exhibit an affinity for each other and arc capable of interacting in vivo. In this manner, the product of the effector construct, comprising CS-BD and HD, is targeted to the CS of the expression construct. Results described herein demonstrate that the activity of the expression construct is repressed through the targeting of an effector construct product comprising HD. While not wishing to be bound by theory, this repression may result from the localized deacetylation of histones by HD which results in the repression of transcription of the coding sequence of interest.

By "controlling sequence" (or CS) it is meant, a nucleotide sequence, for example, but not limited to, a regulatory region of a gene, that interacts with a DNA binding protein. However, a CS may include any nucleotide sequence that interacts with a DNA binding protein. The CS is preferably located in proximity with the coding sequence of interest, either upstream or downstream of the gene. An example of a CS and CS-BD may include, but are not limited to, the GAL4 binding domain (GAL4-BD) and the GAL4 upstream activating sequence (GAL4-UAS). However, it is to be understood that other recognition sequences may be used for this purpose as are known to one of skill within the art. For example, a CS may be an endogenous CS associated with a gene, that is involved within a gene expression cascade, for example but not limited to a developmental cascade. In this embodiment the CS is preferably associated with a gene that is involved at an early stage within the gene cascade, for example homeotic genes. Examples of CS and CS-DB's that are involved in initiating a gene cascade, including homeotic genes are well known to one of skill in the art and include, but are not limited to, transcription factor proteins and associated regulatory regions, for example controlling sequences that bind AP2 domain containing transcription factors, for example, APETALA2 (a regulator of meristem identity, floral organ specification, seedcoat development and floral homeotic gene expression; Jofuku et al., 1994), PRbox (pathogen resistance binding proteins), and several stress induced DNA binding proteins, or CCAAT box-binding transcription factors (e.g. LEC1; WO 98/37184; Lotan, T., et al., 1998, Cell 93, 1195–1205). Other examples which are not to be considered limiting in any manner of such a regulatory region include BNM3, a regulator of embryogenesis (EP 99201745.9-2105; filed Jun. 2, 1999), or the controlling factor associated with PICKLE, a gene that produces a thickened, primary root meristem (Ogas, J., et al., 1997, Science 277, 91–94.)

The first and second regulatory elements denoted above may be the same or different. For example, which is not to be considered limiting in any manner, the second regulatory element may be active before, during, or after the activity of the first regulatory element thereby either initially repressing expression of the coding sequence of interest followed by permitting the expression of the coding sequence of interest, or, following expression of the coding sequence of interest, the second regulatory element becomes active which results in the repression of the expression of the coding sequence of interest. Other examples, which are not to be considered limiting, include the second regulatory element being an inducible regulatory element that is activated by an external stimulus so that repression of gene expression may be controlled through the addition of an inducer. The second regulatory element may also be active during a specific developmental stage preceding, during, or following that of the activity of the first regulatory element. In this way the expression of the coding sequence of interest may be repressed or activated as desired within a plant (see Examples 4 and 5).

It is also within the scope of the present invention that the chimeric construct may comprise the elements of the expression construct, as described above, and those of the effector construct, as described above in a contiguous manner, so that all of the elements for expressing a coding sequence of interest and expressing HD are provided for on one chimeric construct. The first and second regulatory regions may be the same or different, and selected to provide for the constitutive, developmental, temporal or induced expression of either the coding sequence of interest or HD as desired.

The present invention is also directed to a method of regulating gene expression in a transgenic plant that involves the use of only one chimeric construct comprising HD. For example, a method for regulating gene expression may involve:

i) introducing into a plant a chimeric nucleotide sequence comprising a regulatory element in operative association with a nucleotide sequence encoding histone deaceytlase and a nucleotide sequence encoding a controlling sequence binding protein, to produce said transgenic plant; and ii) growing the transgenic plant, wherein the controlling sequence binding protein has an affinity for a native nucleotide sequence within said plant (see Example 6). Preferably the controlling sequence binding protein, for example, but not limited to aDNA binding protein, has an affinity for a controlling sequence, for example a UAS. By selectively binding the controlling sequence, the chimeric construct results in localized deacetylation of histones by HD which results in the repression of transcription of the gene involved in initiating a gene expression cascade.

This invention also pertains to a method for identifying an endogenous DNA binding protein comprising:

i) introducing into an organism a chimeric nucleotide sequence comprising a nucleotide sequence encoding histone deaceytlase and a marker;

ii) growing the organism;

iii) screening mutants that exhibit a mutant phenotype and assaying for the presence of the marker to obtain a mutant organism; and iv) isolating a nucleotide sequence comprising the endogenous DNA binding protein from said mutant organism.

With this method a "promoterless" HD randomly inserts within the host DNA. Several of these insertion events result in the HD lying within the vicinity of an endogenous DNA binding protein. The occurrence of the production of a DNA binding protein-HD chimera represses the expression of the gene typically mediated by the DNA binding protein through the interaction of the DNA binding protein and the controlling sequence. Such an event will result in a mutant phenotype that may then be correlated with the occurrence of the HD-marker within the mutant. Once such a mutant phenotype is identified, the adjacent nucleotide sequence may be obtained using the nucleotide sequence encoding the HD, marker, or both the HD and marker, and the DNA binding protein identified. The controlling sequence may also be identified via methods known within the art, for example South-Western analysis.

The HD of the present invention may also be used for altering the development of an organism. This method comprises:

i) transiently introducing into an organism a chimeric nucleotide sequence comprising a regulatory element in operative association with a nucleotide sequence encoding histone deaceytlase and a nucleotide sequence encoding a DNA binding protein specific for a controlling sequence; and ii) growing the organism.

With this method, by binding a controlling sequence and repressing the expression of its associated gene via HD, the development of the organism may be altered. Preferably the UAS and associated gene are involved at an early stage within the developmental cascade. As a result only the transient expression of the chimeric nucleotide construct comprising HD is required. Such methods for transient expression are well known in the art, and include, but are not limited to viral transformation, or particle bombardment systems (Klein, T. M., Wolf, E. D., Wu, R. and Sanford, J. C.,1987, Nature 327,70–73, which is incorparated by reference).

To identify RPD3 and HD2 homologues in *Arabidopsis thaliana*, a screen of the Arabidopsis expressed sequence tags (ESTs) database was performed with either the yeast RPD3 sequence or the maize HD2 sequence. Two EST clones were identified corresponding to the yeast RPD3 sequence and two clones were identified corresponding to the maize HD2 sequence. These clones were termed AtRPD3A (SEQ ID NO: 1), AtRPD3B (SEQ ID NO:3), AtHD2A (SEQ ID NO:5) and AtHD2B (SEQ ID NO:7), respectively. The deduced amino acid sequences of AtRPD3A (SEQ ID NO: 2) and AtRPD3B (SEQ E) NO:4) showed high levels of overall homology to each other (55% identity). Analysis of the sequence of AtRPD3A revealed the existence of an ORF (open reading frame) of 1509 base pairs encoding a putative protein of 502 amino acids (SEQ ID NO:2; FIG. 1(A)).

Figure 5:
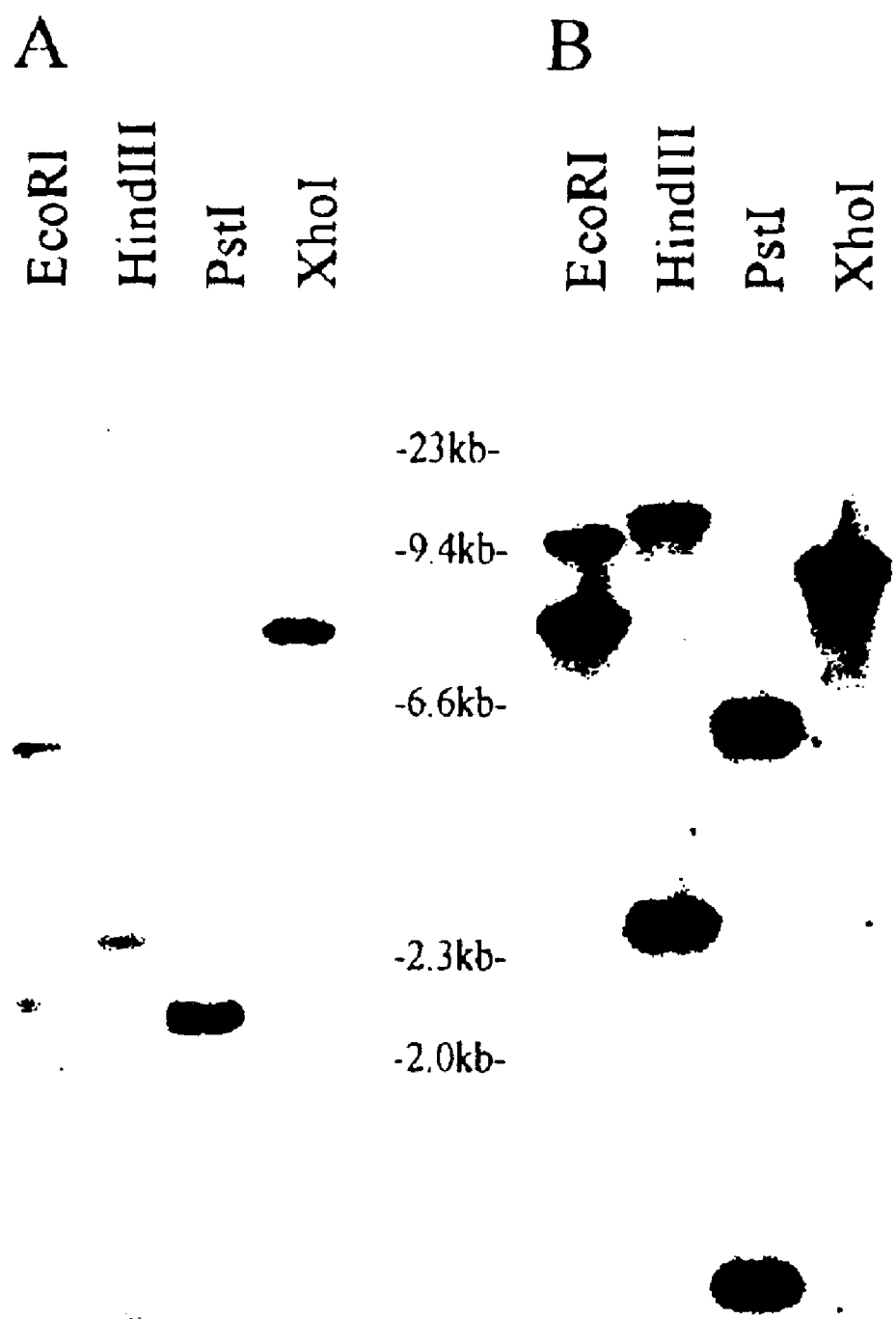
FIG. 5 shows a Genomic Southern blot analysis of AtRPD3A and AtRPD3B. Arabidopsis genomic DNA (approximately 10 μg) was digested with EcoRI, HindIII, PstI, or XhoI, fractionated by agarose gel electrophoresis, transferred to a nylon membrane, and hybridized with the $^{32}$P-labeled AtRPD3A (A) and AtRPD3B (B) cDNA probes.
Figure 6:
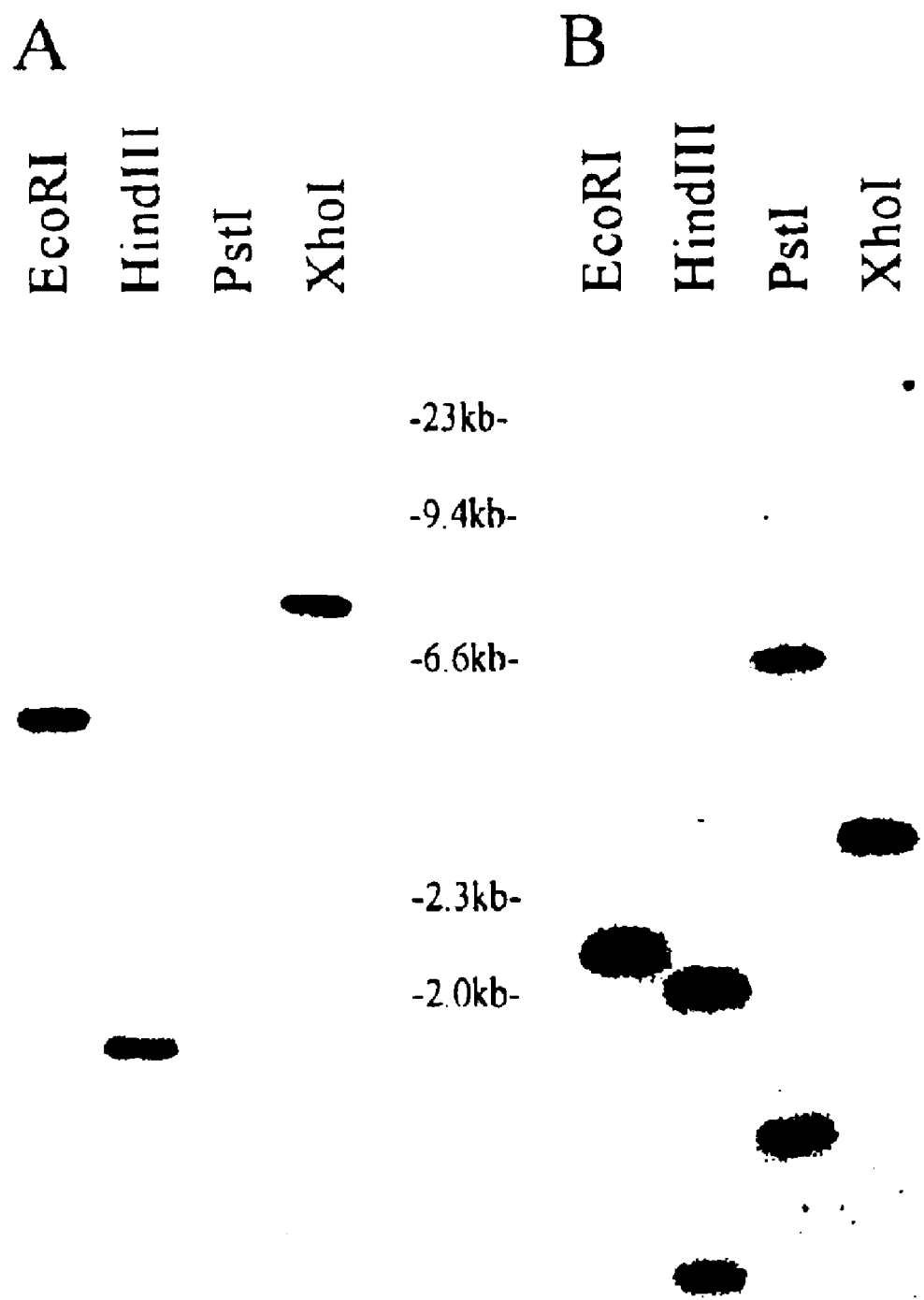
FIG. 6 shows a Genomic Southern blot analysis of AtHD2A and AtHD2B. Arabidopsis genomic DNA (approximately 10 μg) was digested with EcoRI (lane 1), HindIII (lane 2). PstI (lane 3), or XhoI (lane 4), fractionated by agarose gel electrophoresis, transferred to a nylon membrane, and hybridized with the $^{32}$P-labeled AtHD2A (A) and AtHD2B (B) cDNA probes.

To investigate the copy number of AtRPD3A, AtRPD3B, AtHD2A and AtHD2B genes in the Arabidopsis genome, $^{32}$P-labeled AtRPD3A, AtRPD3B, AtHD2A and AtHD2B cDNA probes were hybridized to Arabidopsis genomic DNA digested with EcoRI, HindIII, PstI and XhoI restriction enzymes (FIGS. 5 and 6). One single band or two bands were observed in each lane, indicating that AtRPD3A, AtRPD3B, AtHD2A and AtHD2B genes are present as a single copy in the Arabidopsis genome.

Figure 7:
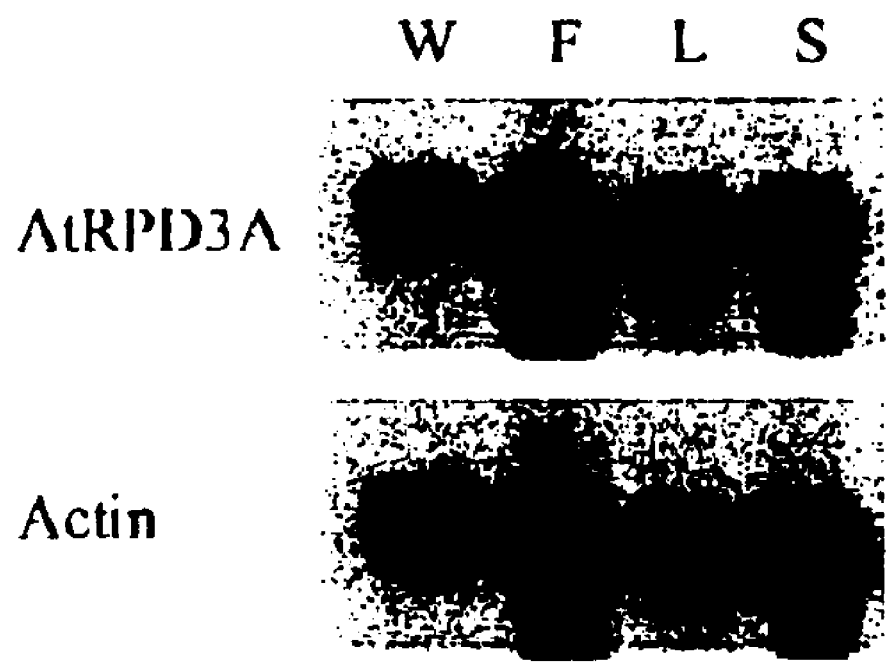
FIG. 7 displays a Northern blot analysis of the AtRPD3A transcripts. Total RNA was isolated from leaves (L), stems (S), flowers and young siliques (F), and whole plants (W) of *Arabidopsis thaliana*. Five microgram of total RNA was probed with AtRPD3A and a loading control probe (actin).

The expression levels of AtRPD3A and AtRPD3B transcripts in Arabidopsis plants were analyzed by Northern hybridization. As shown in FIG. 7, AtRPD3A RNA accumulated to relatively high levels in the leaves, stems, flowers and young siliques. AtRPD3B RNA, however, was not detectable under the same experimental conditions (data not shown), suggesting that AtRPD3B was not expressed or expressed at a very low level in these organs.

Figure 8:
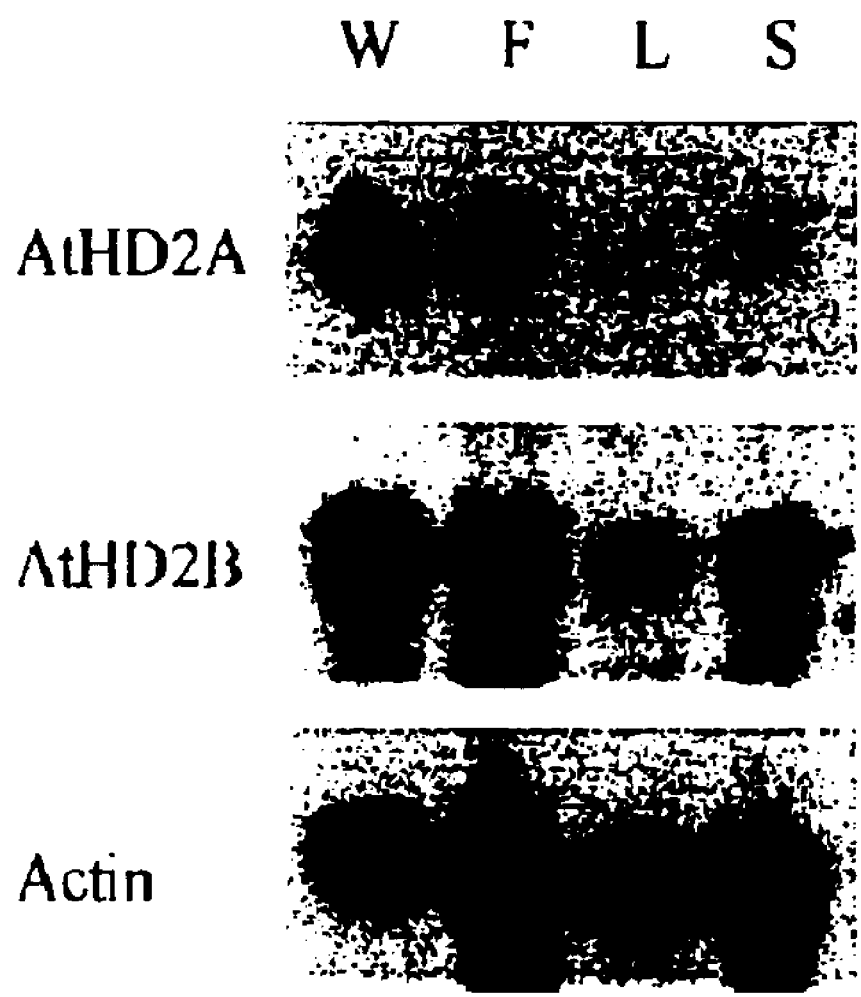
FIG. 8 displays a Northern blot analysis of the AtHD2A and AtHD2B transcripts. Total RNA was isolated from leaves (L), stems (S), flowers and young siliques (F), and whole plants (W) of *Arabidopsis thaliana*. Five microgram of total RNA was probed with AtHD2A, AtHD2B and a loading control probe (actin).

The pattern of AtHD2A and AtHD2B RNA expression in Arabidopsis plants was similarly analyzed by Northern hybridization (FIG. 8). AtHD2A RNA accumulated in the flowers and young siliques. AtHD2B RNA, however, accumulated to relative high levels in the stem, flowers and young siliques and to a somewhat lower level in the leaves.

Repression of Gene Expression by AtRPD3A and AtHD2A

To determine if Arabidopsis RPD3-like and HD-like proteins possess gene repression activity, effector plasmids were constructed A GAL4-AtRPD3A effector plasmid was designed and constructed in which the AtRPD3A protein was fused with the DNA-binding domain of the yeast transcription factor GAL4 (Giniger et al., 1985; Ma et al., 1988) and driven by full length tCUP, a strong constitutive promoter (Foster et al., 1999) (See FIG. 9(A) for effector and reporter constructs). A report plasmid, UAS$_{GAL4}$-tCUP-GUS, was constructed using a GUS reporter gene and in which two GAL4-binding sites (UAS$_{GAL4}$) were fused to a truncated tCUP promoter, -394-tCUP (Foster et al., 1999). Each of the effector plasmids, either GAL4-AtRPD3A or GAL4, was co-bombarded into tobacco leaves together with the reporter plasmid UAS$_{GAL4}$-tCUP-GUS, the idea being that the fusion protein would target AtRPD3A to promoters containing the GAL4-binding sites (UAS$_{GAL4}$). In the case of the control, the reporter plasmid was cobombarded with the control plasmid pUC19.

As shown in FIG. 9(B) the levels of GUS activity were essentially the same when the reporter plasmid was co-bombarded with either the control plasmid pUS19, or GAL4 effector plasmid. However, an approximate 2-fold repression in GUS activity was observed in the presence of GAL4-AtRPD3A when compared with the other two treatments. This demonstrates that the protein product of AtRPD3A gene expression is capable of mediating transcriptional repression of transgenic sequences and suggest that transcriptional repression occurs by targeted histone deacetylation and the establishment of a locally repressive chromatin structure.

Similar constructs were tested in a like manner for AtHD2A proteins. A reporter plasmid was constructed with a GUS reporter gene (UAS$_{GAL4}$-tCUP-GUS) in which GAL4-binding sites (UAS$_{GAL4}$) were fused to the strong constitutive promoter -394-tCUP (Foster et al., 1999). The reporter gene was designed to be repressed by the fusion protein encoded by the effector plasmid GAL4-AtHD2A. As shown in FIG. 10(A), the AtHD2A protein (AtHD2A, 1-245) was fused with the DNA-binding domain of the yeast transcription factor GAL4 (GAL4BD) (Giniger et al., 1985; Ma et al., 1988). Several deletions of AtHD2A were also prepared and tested in association with the reporter construct. Each of the effector plasmids also contained the 35S promoter. Tobacco leaves were cobombarded with the reporter construct and either GAL4, one of the AtHD2A effector plasmids, or the control plasmid pUS19, and GUS activity determined.

Co-bombardment of leaves with either reporter and the control construct or reporter and GAL4 resulted in a high level of GUS activity (FIG. 10(B)), while co-bombardment with AtHD2A significantly reduced GUS activity. These results again indicate that AtHD2A can mediate transcriptional repression of a targeted reporter gene in vivo. To determine the protein domains of AtHD2A responsible for gene repression, a series of deletion constructs of AtHD2A were made (FIG. 10(B)) and tested by transient expression in Arabidopsis plants. Deletion of C-terminal residues up until the amino acid 162 of AtHD2A (GAL4-AtHD2A, 1–211 and GAL4-AtHD2A, 1–162) did not affect the repression activity of the molecules (FIG. 10(B)). However, further deletions to the amino acid 100 of the C-terminal residue (GAL4-AtHD2A, 1–100) resulted in a complete loss of gene repression activity. This observation indicates that the region between the amino acid residues 101 to 161 is important for repression activity. This region also includes an extensive acidic amino acid domain, which is important for association with basic tails of histories (Philpott and Leno, 1992). Deletion of the domain containing predicted catalytic residues (GAL4-AtHD2A, 73–245) resulted in complete loss of repression activity (FIG. 10(B)). Collectively, these results demonstrate that both the deacetylase catalytic activity and HD binding with histones is essential for gene repression activity. Furthermore, these results indicate that fragments or analogs of HD are active in repressing the expression of a coding sequence of interest.

Antisense Expression of AtRPD3A and AtHD2A

Figure 12:
FIG. 12 shows the Northern analysis of AtRPD3A mRNA in transgenic plants. Analysis of AtRPD3A expression in wild-type line (WT) and antisense lines (B2, B5 and A1). Five microgram of total RNA isolated from leaves was probed with AtRPD3A cDNA probe and a loading control probe (actin).

The difference in AtRPD3A and AtRPD3B expression suggests that these genes and their corresponding proteins might function in different roles during plant growth and development. To test this hypothesis. Arabidopsis plants were transformed with an antisense construct of the AtRPD3A cDNA. Transgenic Arabidopsis plants were generated that expressed antisense AtRPD3A driven by the strong constitutive promoter, -394-tCUP (Foster et al., 1999). A truncated 519 bp fragment of AtRPD3A cDNA driven by -394-tCUP promoter was used to make an antisense construct (FIG. 11). The expression of antisense AtRPD3A RNA in the transgenic lines was monitored by Northern analysis (FIG. 12). Because a truncated AtRPD3A cDNA was used to make the antisense constructs, it was expected that the antisense transcript would be smaller than the endogenous sense transcript. Indeed, two transcripts, a large transcript (1.6 kb) and a smaller transcript (0.6 kb), were detected using an AtRPD3A cDNA probe in the antisense transgenic lines FIG. 12). The smaller transcript was absent from the wild-type plants and represented the AtRPD3A antisense transcript. As shown in FIG. 12, different levels of endogenous sense AtRPD3A transcript were detected in three independent antisense lines with high levels of expression of antisense transcript. Two antisense lines. B5 and A1, also showed a considerable reduction of endogenous transcripts compared with wild-type.

Figure 14:
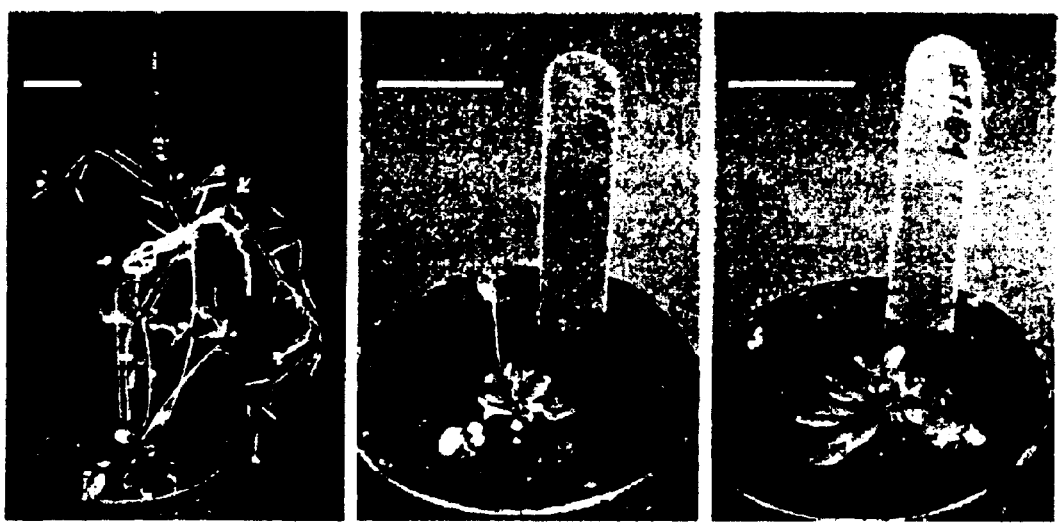
FIG. 14 displays the phenotypic abnormalities of plants expressing AtRPD3A antisense RNA. Wild-type plant (A) and antisense AtRPD3A transgenic plants (B and C) were grown for 6 weeks. The transgenic plants show a delay in flowering compared to the wild-type plant.

The two independent antisense lines with reduced endogenous AtRPD3A transcripts had a delayed-flowering phenotype compared with wild-type plants. As shown in FIG. 14, control wild-type plants started flowering alter approximately 3 weeks of vegetative growth. In contrast, flowering of the antisense lines A1 and B5 was delayed for two to three weeks. These results suggest that AtRPD3A is important for normal plant growth and development.

In Arabidopsis, the difference in AtHD2A and AtHD2B expression patterns also suggests that these genes and their corresponding proteins may play different roles during normal plant growth and development. AtHD2B appears to be expressed constitutively in Arabidopsis. Whereas AtHD2A, shows a restricted pattern of expression within the flowers and siliques.

Figure 13:
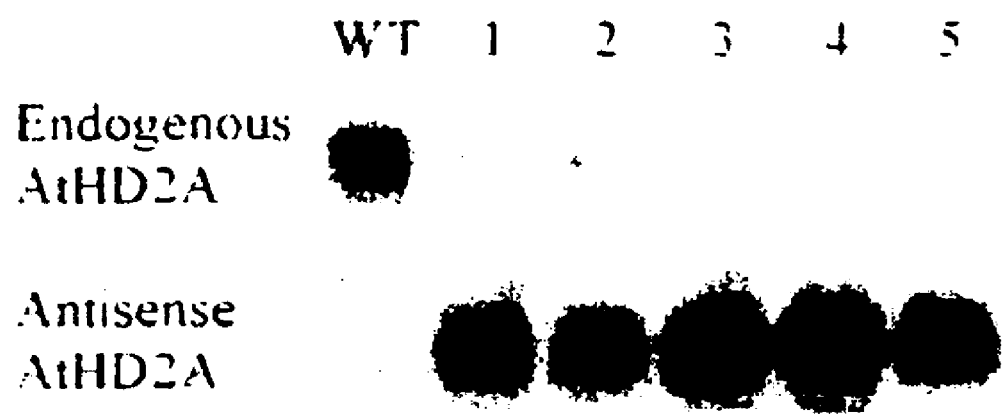
FIG. 13 shows the Northern analysis of AtHD2A antisense plants. Analysis of endogenous AtRPD2A expression of wild-type line (WT) and antisense transgenic lines (1–5). Five microgram of total RNA isolated from flower and young siliques was probed with an endogenous AtRPD3A specific probe and an anti sense AtRPD3A specific probe.

To further study the function of HD2-like proteins, transgenic Arabidopsis (ecotype Columbia) were constructed. These plants that expressed antisense AtHD2A from a strong constitutive promoter, -394-tCUP. The expression of the AtHD2A antisense gene in the transgenic lines was verified by Northern analysis. An antisense specific probe derived from the 5' untranslated region of the AtHD2A antisense construct was used to monitor the expression of the AtHD2A antisense gene. As shown in FIG. 13, five independent transgenic lines showed high expression of antisense AtHD2A transcript. A 3' untranslated region of AtHD2A cDNA which was absent from the AtHD2A antisense construct was used to detect the endogenous AtHD2A mRNA. As shown in FIG. 13, the levels of endogenous AtHD2A transcript were significantly reduced in the transgenic lines, suggesting that antisense transcripts might trigger AtHD2A mRNA degradation.

Figure 15:
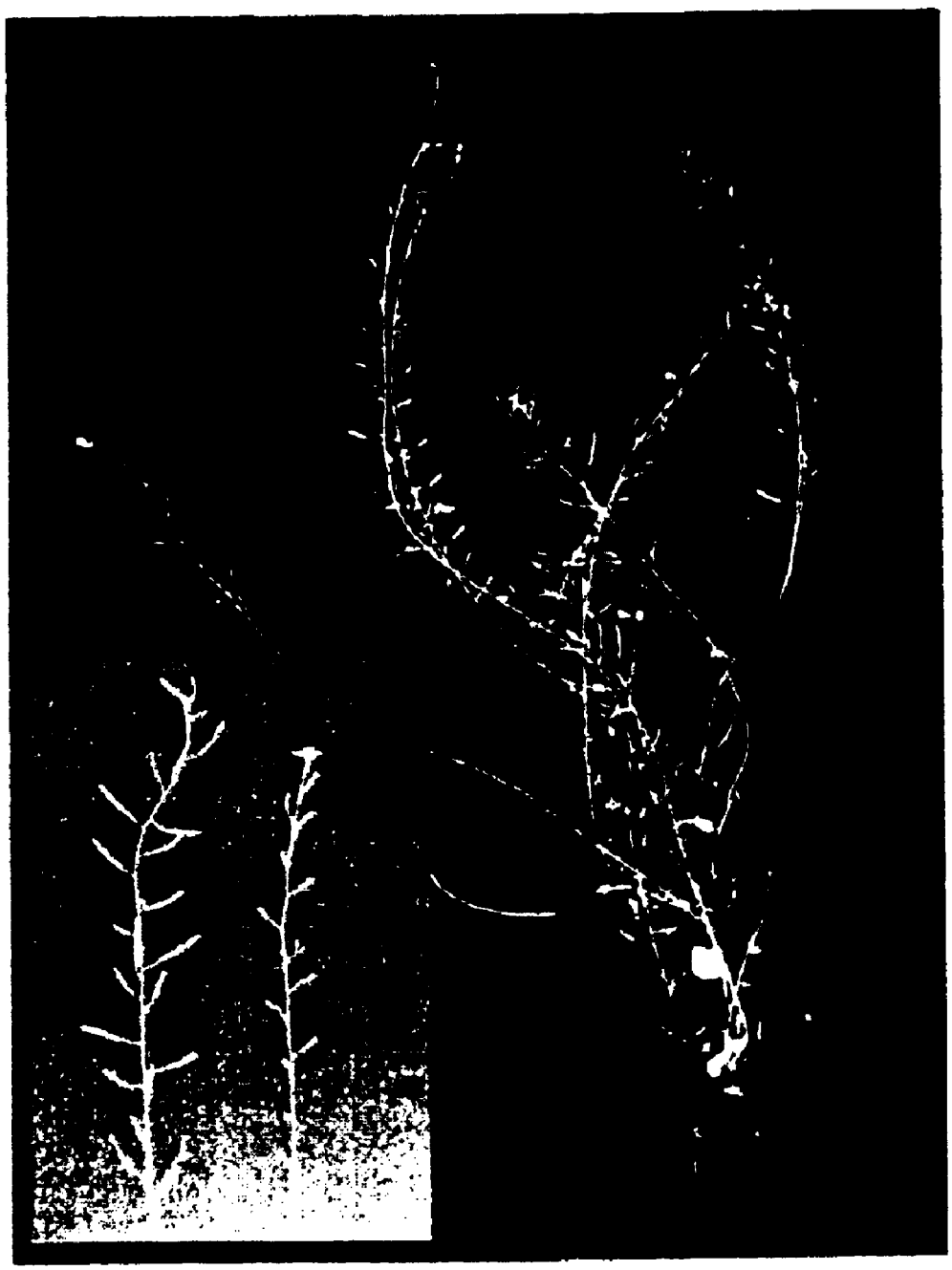
FIG. 15 displays the phenotype of AtHD2A antisense plants. An AtHD2A antisense plant is semi-sterile and exhibits a reduced seed set. The insert shows a wild-type stem with full silique elongation (left) and a stem from an AtHD2A antisense plant with stunted siliques (right).
Figure 18:
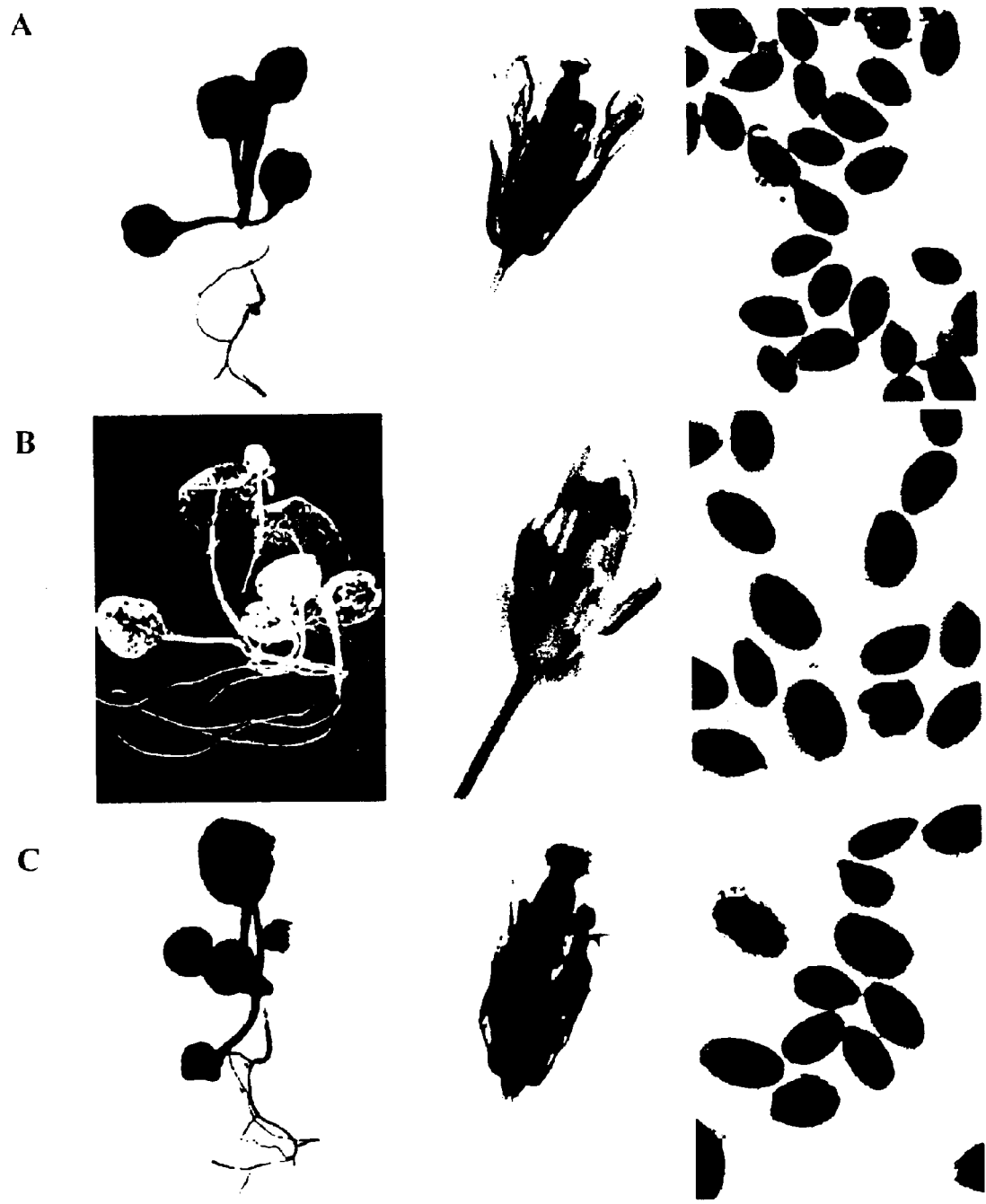
FIG. 18 shows reporter gene activity within plants produced following the experiment outlined in FIG. 17.

The five independent transgenic lines with reduced endogenous AtHD2A RNA levels had stunted siliques and produced fewer seeds compared with wild-type (FIG. 15), and they were therefore semi-sterile. The wild-type plants were distinguished from the transgenic plants by the length of the siliques and the seed set. In the semi-sterile transgenic plants, silique length and seed set varied along the stem and from inflorescence to inflorescence. Siliques from the wild type and the sterile transgenic plants were dissected and examined by stereomicroscopy and scanning electron microscopy. As shown in FIG. 16, the transgenic mature siliques contained aborted seeds, which were significantly smaller than the healthy seeds from the wild-type plants.

Antisense expression of histone deacetylase genes may have resulted in an alteration in the chromatin structure by hyperacetylation of histones, which subsequently affected gene transcription. Our study indicates that histone deacetylases play an important role in regulating different developmental pathways of plants and that the developmental abnormalities seen in deacetylase antisense plants may be due to dysregulation of gene expression.

Tissue Specific Gene Repression

Tissue-specific repression of gene expression is also observed in plants using tissue-specific regulatory elements to drive the expression of either the expression, effector, or bothe the expression and effector construct. As described herein, which is not to be considered limiting in any manner, seed specific expression of either the expression or effector construct may be obtained using the napin promoter. Results demonstrate that repression of an expression construct under the control of a constitutive regulatory element in a tissue-specific manner may be obtained by either crossing plants expressing the expression construct with plants expressing tissue-specific expression of the effector construct (see Example 4), by sequentially transforming plants with an expression construct, and then re-transforming the plant with an effector construct to produce a dual transgenic plant (see Example 5), or co-transforming a plant with both the expression and effector construct at the same time (e.g. Example 2). An outline of the experimental approach for crossing plants expressing an expression construct with plants expressing an effector construct to produce a dual transgenic plant is presented in FIG. 17(A). Non-limiting examples of constructs that exemplify this procedure are schematically presented in FIG. 17 (B), however, it is to be understood that other expression effector constructs may be used to drive repression of a desired gene in a plant.

Plants transformed with $UAS_{GAL4}$-tCUP-GUS were crossed with either tCUP-GAL4/AtHD2A (constitutive expression) and NAP-GAL4/AtHD2A (tissue specific expression) effector lines. Analysis of the F1 progeny from a cross between $UAS_{GAL4}$-tCUP-GUS X 35S-GAL4/AtHD2A, and $UAS_{GAL4}$-tCUP-GUS X NAP1-GAL4/AtHD2A are presented in FIG. 19(A). High levels of expression of a coding sequence of interest (e.g. reporter gene activity) are observed in leaves and seeds in control plants expressing GUS under the control of the constitutive regulatory element tCUP. In F1 progeny of plants derived from a cross between $UAS_{GAL4}$-tCUP-GUS X 35S-GAL4/AtHD2A, reduced reporter gene expression is observed in both leaves and seeds, due to the constitutive expression of the HD/GAL4BD, and the $UAS_{GAL4}$-reporter genes. High levels of expression of a coding sequence of interest (e.g. a reporter gene) are observed in leaf tissue of F1 progeny derived from a cross between $UAS_{GAL4}$-tCUP-GUS X NAP1-GAL4/AtHD2A due to a lack of expression of the effector construct under the control of the tissue-specific promoter. However, in seed tissues, reporter expression is dramatically reduced due to the targeted expression of the HD/GAL4BD.

Similar results are obtained in dual transgenic plants that have been transformed sequentially, that is, following the initial transformation of a plant with an expression gene (for example GUS), the transgenic plant is re-transformed with an effector gene. As shown in FIGS. 19(B) and (C), plants transformed with both an expression construct and re-transformed with either 35S-GAL4/AtHD2A, or NAP1-GAL4/AtHD2A display similar patterns of repression of the coding sequence of interest as that observed following crossing expression X effector plant lines. In plants sequentially transformed with the reporter construct and an effector construct that is constitutively expressed in the plant (35S-GAL4/HD). ,repression of GUS activity is observed in both leaves and seed (FIGS. 19(B) and (C)). Repression of GUS activity is only observed in seed tissues in dual transgenic plants sequentially transformed with the expression construct followed by the seed specific effector construct NAP1-GAL4/HD. No repression of reporter gene activity was observed in leaf tissue in dual transgenic plants re-transformed with the seed specific effector construct.

Plant Transcription Factors may be Used to Repress Developmental, Physiological, or Biochemical Pathways The methods as described herein may also be used to repress developmental, physiological and metabolic pathways in plants. In this embodiment, protein factors bind specific DNA sequences within a regulatory region of a gene. These protein factors function as a controlling sequence binding domain (CS-BD), and the specific DNA sequence to which the CS-BD binds function as a controlling sequence (CS).

An example, which is not to be considered limiting in any manner, involves the use of an effector construct comprising HD associated with a CS-BD. The CS-BD, for example, but not limited to a transcription factor, is capable of binding an endogenous CS within the plant, thereby permitting the associated HD to repress expression of a gene associated with the CS. If the CS is associated with a gene involved with a developmental or metabolic cascade, for example but not limited to a homeotic gene, then repression of the coding sequence of interest ensures that the cascade is not initiated.

An example to demonstrate that developmental, physiological or biochemical pathways can be regulated by the methods as disclosed herein, involves the repression of a developmental or metabolic pathway associated with the ethylene response in plants using the transcriptional factor Pti4 fused with histone deacetylase.

Pti4 is a tomato transcription factor that belongs to the ERF (ethylene-responsive element binding factor) family of proteins. It interacts with the Pto kinase in tomato, which confers resistance to the *Pseudomonas syringae* pv tomato pathogen that causes bacterial speck disease. To study the function of Pti4, transgenic Arabidopsis plants were generated that expressed tomato Pti4 driven by the strong constitutive promoters, CaMV 35S and -394-tCUP.

Pti4 enhanced GCC box-mediated transcription of a coding sequence of interest with which it was co-transformed (FIG. 20). Solano et al. (1998) reported that overexpression of another ERF (ethylene-responsive element binding factor) protein, ERF1, in transgenic: Arabidopsis plants induced basic chitinase gene expression. Basic chitinase is an ethylene-responsive gene, which contains the GCC box in its promoter (Samac et al., 1990). The GCC-box contains a conserved AGCCGCC sequence, which was first identified from the promoters of ethylene-inducible PR genes in tobacco (Ohme-Takagi and Shinshi, 1995). Without wishing to be bound by theory, it has been suggested that this sequence is a target in the ethylene signal transduction pathway because deletion of the GCC box eliminates ethylene responsiveness (Broglie et al., 1989; Shinshi et al., 1995). Therefore, the expression of tomato Pti4 in Arabidopsis was examined to determine if Pti4 could induce the expression of the Arabidopsis basic chitinase gene. Northern analysis also showed that expression of Pti4 in transgenic Arabidopsis plants induced the expression of a GCC box-containing, endogenous, PR gene, basic chitinase, in Arabidopsis (FIG. 21).

The ethylene-responsive phenotype is exhibited in Arabidopsis by an inhibition of root and hypocotyl elongation, radial swelling of the hypocotyl and root, and exaggeration in the curvature of the apical hook (Ecker, 1995; Chang and Shockey, 1999). The hypocotyls of etiolated transgenic seedlings were measured 72 hrs after germination. Plants expressing Pti4/HD construct showed inhibition of hypocotyl elongation, a phenotype similar to those observed in the constitutive ethylene response-mutants or in wild-type plants exposed to ethylene (Solano et al., 1998). As shown in the FIGS. 22 and 23, the seedlings from the transgenic line tCUP/Pti4-1 displayed strong inhibition of hypocotyl elongation similar to that seen in plants treated with ethylene (ACC), suggesting that the Pti4 gene is involved in the regulation of a subset of ethylene responsive genes which contain the GCC box, and indicate that tomato Pti4 acts as a transcriptional activator to regulate expression of GCC box-containing genes.

To test the effect of Pti4-AtHD2A protein on the ethylene signaling pathway, transgenic plants overexpressing Pti4-AtFD2A were examined for the ethylene-responsive phenotype. The hypocotyls of the etiolated transgenic seedlings were measured 72 hrs after germination. As shown in the FIGS. 24, wild type seedlings (FIG. 24(A)) exhibited hypocotyl elongation. Seedlings overexpressing Pti4 (FIG. 24(B) exhibited the ethylene responsive phenotype (inhibition of hypocotyl elongation). However, seedlings from the transgenic line Pti4-HDA (FIG. 24(C)) did not display inhibition of hypocotyl elongation, demonstrating that Pti4-AtHDA fusion proteins repressed ethylene responsive phenotype in transgenic plants.

Therefore the present invention is directed to a method of regulating the expression of a coding sequence of interest in a plant comprising:

i) introducing into the plant a chimeric nucleotide sequence comprising a regulatory element in operative association with a nucleotide sequence encoding histone deaceytlase fused with a nucleotide sequence encoding a controlling sequence binding domain that has an affinity for a native controlling sequence upstream within the gene, to produce a transgenic plant; and ii) growing the transgenic plant.

The controlling sequence binding domain may be for example a DNA binding protein, and the controlling sequence may be an upstream activating sequence.

Similarly, the above method may be used to regulate a developmental, physiological, or biochemical pathway within a plant by introducing into the plant a chimeric nucleotide sequence comprising a regulatory element in operative association with a nucleotide sequence encoding histone deaceytlase fused with a nucleotide sequence encoding a DNA binding protein that has an affinity for a native upstream activating sequence within the coding sequence of interest known to be associated with a developmental, physiological or biochemical cascade, for example a homeotic gene, to produce a transgenic plant.

Identification of DNA Binding Proteins

The method of repressing gene expression as disclosed herein may also be used as a functional test for identifying a phenotype associated with perturbing a gene comprising a controlling sequence, as well as identifying controlling sequences, upstream activating sequences, controlling sequence binding domains, transcription factors, or DNA binding proteins in general.

In this method, a nucleotide sequence of unknown function, for example a putative transcription factor, can be tested to see if it targets the repression of gene expression, when fused with a histone deacetylase. If an altered phenotype can be determined as a result of the introduction of the construct into the plant, then this indicates that the unknown nucleotide sequence interacts with a controlling sequence associated with a gene in such as manner so as to permit HD to modify/repress the expression of the gene. Such a functional test can be used to screen nucleotide sequences thought to comprise DNA binding proteins, and determine the associated phenotype arising from repressing expression of the gene comprising the controlling sequence.

Therefore, the present invention also provides for a method for identifying DNA binding protein comprising:

i) introducing into the plant a chimeric nucleotide sequence comprising a regulatory element in operative association with a nucleotide sequence encoding histone deaceytlase fused with a nucleotide sequence of interest and of unknown function (e.g. a putative DNA binding protein), to produce a transgenic plant;
  ii) growing the transgenic plant; and
  iii) examining the phenotype of the transgenic plant to determine whether the chimeric nucleotide sequence, comprising the nucleotide sequence of interest has an effect on the plant phenotype.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLE 1

Growth of Plant Material

*Arabidopsis thaliana* (ecotype Columbia) was grown in a growth chamber (16 hr of light and 8 hr of darkness at 23° C.) after a 24 day vernalization period. For growth under sterile conditions, seeds were surface sterilized (15 min incubation in 5% [v/v] sodium hypochlorite, and a threefold rinse in sterile distilled water) and sown on half-strength Murashige and Skoog (MS) salts (Sigma) (Murashige and Skoog. 1962) supplemented with 1% sucrose, pH 5.7, and 0.8% (w/v) agar in Petri dishes.

Isolation of AtRPD3 and AtHD2

To identify RPD3 and HD2 homologues in Arabidopsis thaliana, a screen of the Arabidopsis expressed sequence tags (ESTs) database was performed with either the yeast RPD3 sequence or the maize HD2 sequence. Two EST clones were identified corresponding to the yeast RPD3 sequence and two clones were identified corresponding to the maize HD2 sequence. The clones were termed AtRPD3A, AtRPD3B, AtHD2A and AtHD2B, respectively.

DNA and Protein Sequence Analysis

Dye primer sequencing of cDNA clone inserts and dye terminator sequencing of PCR products were performed using an automated sequencing system (Applied Biosystems). DNA and protein sequence analysis was carried out using BLAST searches (Altschul et al., 1990) and the DNASIS program (Hitachi Software Engineering Co., Ltd).

The isolated clones were sequenced AtRPD3A (SEQ ID NO:1), AtRPD3B (SEQ ID NO:3), AtHD2A (SEQ ID NO:5) and AtHD2B (SEQ ID NO:7), respectively (see also FIGS. 1 and 2).

The sequence of cDNA clone AtRPD38 is truncated at the 5' extremity in comparison to AtRPD3A. The genomic sequence of AtRPD3B was identified on chromosome S of Arabidopsis (GenBank accession no. AB008265). The sequence of AtRPD3B encodes an ORF of 1416 base pairs encoding a putative protein of 471 amino acids (SEQ ID NO:4; FIG. 1(B)).

Analysis of the sequences of the AtHD2A revealed an ORF of 738 base pairs encoding a putative protein of 245 amino acids whereas the sequence of the AtHD2B contained an ORF of 918 base pairs encoding a putative protein of 305 amino acids (SEQ ID NO's: 6 and 8, respectively; FIG. 2).

The deduced protein sequences of AtRPD3A and AtRPD3B were aligned with yeast RPD3, and the maize RPD3 homolog, ZmRPD3 (Rossi et al., 1998). As shown in FIG. 3, AtRPD3A is more closely related to maize ZmRPD3 (73% identity) than to yeast RPD3 (49% identity). AtRPD3B, however, shows 57% and 55% amino acid identity with maize ZmRPD3 and yeast RPD3, respectively. The putative residues essential for histone deacetylase activity (Hassig et al., 1998) were strictly conserved in all of these proteins (FIG. 3).

The deduced protein sequences of AtHD2A and AtHD2B was aligned with maize HD2, ZmHD2 (Lusser et al., 1997; FIG. 4). The AtHD2A and AtHD2B sequences share 52% amino acid identity to each other, and they share 44% and 46% amino acid identity with the ZmHD2, respectively. As shown in FIG. 4, the predicted histone deacetylase catalytic residues (Aravind and Koonin, 1998) are conserved in the N-terminal domains of both AtHD2A and AtHD2B. Similarly, both proteins contain an extended acidic amino acid domain, with high sequence homology to nucleolar proteins from several organisms (Lusser et al., 1998). Additionally, a putative zinc finger is encoded at the C-terminal domain of AtHD2A, but not at the C-terminal of AtHD2B.

Southern and Northern Blot Analysis

Total genomic DNA from Arabidopsis was extracted as described (Dellaporta et al. 1983). For Southern blots, Arabidopsis genomic DNA was digested with restriction enzymes, separated by agarose gel electrophoresis, and transferred to nylon membranes (Sambrook et al., 1989). For Northern analysis, total RNA was isolated from 100–200 mg Arabidopsis tissues using Tri™Pure Reagent as described by the manufacturer (Boehringer Mannheim). Northern blots were prepared by electrophoresis of 5–10 µg samples of total RNA through agarose gels in the presence of formaldehyde (Strommer et al., 1993), followed by transfer to nylon membranes. Southern and Northern blots were probed with $^{32}$P-labeled probes. Prehybridization and hybridization were performed at 65° C. in 0.5 M $Na_2HPO_4$ (pH 7.2), 7% SDS, and 1 mM EDTA. Filters were washed once for 15 min in 2×SSC with 0.1% SDS at room temperature, then twice for 20 min in 0.1×SSC, 0.1% SDS at 65° C. The damp filters were autoradiographed at −80° C. using two intensifying screens. Filters were stripped in 5 mM Tris-HCl, pH 7.5, 1 mM EDTA, 0.05% SDS at 100° C. for 2 min when reprobing was required. As a control, all Northern blots were also probed with an Arabidopsis actin (EST clone 40F11 from the Arabidopsis Biological Resource Center, Ohio State University).

To investigate the copy number of AtRPD3A, AtRPD3B, AtHD2A and AtHD2B genes in the Arabidopsis genome, $^{32}$P-labeled AtRPD3A, AtRPD3B, AtHD2A and AtHD2B cDNA probes were hybridized to Arabidopsis genomic DNA digested with EcoRI, HindIII, PstI and XhoI restriction enzymes (FIGS. 5 and 6). One single band or two bands were observed in each lane, indicating that AtRPD3A, AtRPD3B, AtHD2A and AtHD2B genes are present as a single copy in the Arabidopsis genome.

The expression levels of AtRPD3A, AtRPD3B, AtHD2A and AtHD2B transcripts in Arabidopsis plants were analyzed by Northern hybridization (FIGS. 7 and 8). AtRPD3A RNA accumulates to relatively high levels in the leaves, stems, flowers and young siliques. AtRPD3B RNA, however, was not detectable under the same experimental conditions (data not shown), suggesting that AtRPD3B was not expressed or expressed at a very low level in these organs (FIG. 7). AtHD2A RNA accumulated in the flowers and young siliques. AtHD2B RNA, however, accumulated to relative high levels in the stem, flowers and young siliques and to a somewhat lower level in the leaves (FIG. 8).

EXAMPLE 2

Construction of Transformation Plasmids

To construct a reporter construct (an expression construct), the CaMV 35S promoter of pBI221 (Clontech) was replaced with a truncated tCUP promoter, -394-tCUP (Foster et al., 1999) to generate the pBI-BtCUPvector. A 76-bp fragment (CGGAGGACTGTCCTCCGATCGGAG GACTGTCCTCCGTGCA: SEQ ID NO: 9) containing two upstream activating sequence of the yeast GAL4 protein (UAS$_{GAL4}$) was ligated into the PstI site located upstream of the -394-tCUP promoter.

AtRPD3A Effector Plasmids

To construct the effector plasmids, we replaced the 35S promoter of pBI221 with the tCUP promoter (Foster et al., 1999), to generate the pBI-tCUP vector. The GUS gene in the pBI-tCUP was replaced with the AtRPD3A coding region, and the DNA-binding domain of GAL4 (amino acids 1–147) was subcloned in-frame into the XbaI and XmaI sites.

AtHD2A Effector Plasmids

To construct the effector plasmids, the GUS gene in the pBst-tCUP was replaced with the AtHD2A and its deletions, then the DNA binding domain of GAL4 was subcloned in-frame into the XbaI and XmaI sites.

Particle Gun Delivery Assays

Tobacco (SR1) plants were maintained in vitro in half-strength MS medium (Murashige and Skoog, 1962) in Magenta containers (Magenta Corp., Chicago) in a growth chamber at 25° C. After transfer to fresh medium for two to three weeks, uniform-sized leaves (about 3 cm in width) were cut off from the plants and placed on a medium consisted of MS salts, B5 vitamins (Gamborg et al., 1968), 1 mg/L 6-benzyladenine, 0.1 mg/L naphthalene acetic acid, 3% sucrose and 0.25% Gelrite in a 20×15 mm Petri dish. The leaves were preconditioned on this medium for one day prior to gene delivery.

Plasmid DNA was isolated using a QIAGEN Plasmid Midi Kit. The reporter plasmid was mixed with an effector plasmid at 1:1 ratio (weight). In the control, the reporter was mixed with an equal amount of control plasmid pUS19. A modified particle inflow gun (Brown et al., 1994) was used for DNA delivery. DNA was precipitated onto tungsten particles by using the following protocol: a 5 µd sample of mixed DNA (1 µg/µ) was added to 25µ tungsten particles (100 mg/ml) and followed by the addition of 25 µl of 2.5 M CaCl$_2$ and 5 µl of 0.1 M spermidine. The leaves were bombarded once at a distance 16 cm from the screen and under the pressure of 1000 kPa He gas.

Bombarded leaves were maintained on the same medium for 1 day. Gene expression was determined by histochemical and fluorometric assays (Jefferson 1988). GUS activity was reported as picomoles of 4-methylumbelliferone per milligram of protein per minute.

Repression of Gene Expression by AtRPD3A and AtHD2A

Each of the effector plasmids (as described above), either GAL4-AtRPD3A or GAL4, was cobombarded into tobacco leaves together with the reporter plasmid UAS$_{GAL4}$-tCUP-GUS (as described above). In the case of the control, the reporter plasmid was co-bombarded with the control plasmid pUS19.

As shown in FIG. 9(B) an approximate 2-fold repression in GUS activity was observed when GAL4-AtRPD3A was co-bombarded with the reported construct, when compared with the the control or GAL4 contructs. These results indicate that the protein product encoded by AtRPD3A is capable of mediating transcriptional repression of transgenic sequences.

Similar constructs, prepared as indicated above, were tested in a like manner for AtHD2A proteins. Co-bombardment of leaves with either reporter and control construct or reporter and GAL4 resulted in a high level of GUS activity (FIG. 10(B)). Co-bombardment with AtHD2A resulted in reduced GUS activity. These results again indicate that AtHD2A mediates transcriptional repression of a targeted reporter gene in vivo.

A series of deletion constructs of AtHD2A were made (FIG. 10(B) and tested by transient expression in Arabidopsis plants. Deletion of C-terminal residues up until the amino acid 162 of AtHD2A (GAL4-AtHD2A, 1–211 and GAL4-AtHD2A,1–162) did not affect the repression activity of the molecules (FIG. 10(B). Deletion of the domain containing predicted catalytic residues (GAL4-AtHD2A, 73–245) resulted in complete loss of repression activity (FIG. 10(B)). Furthermore, GA1-AtHD2A, 1–100 (with deletions to the amino acid 100 of the C-terminal residue) resulted in a complete loss of ,ene repression activity. This region includes an extensive acidic amino acid domain, which is known to intereact with basic tails of histones.

Collectively, these results demonstrate that both the deacetylase catalytic activity and HD binding with histones is essential for gene repression activity. Furthermore, these results indicate that fragments or analogs of HD are active in repressing the expression of a coding sequence of interest.

EXAMPLE 3

Antisense Constructs

To generate the antisense constructs, pBI-BtCUP was digested with EcoRI and HindIII, and the resulting fragment containing the -394-tCUP promoter and the GUS gene was then subcloned into the multi-cloning sites of pCAM-BIA2300 binary vector (Cambia, Canberra, Australia) to generate the pCBtCUP vector. AtRPD3A cDNA was digested by SacI and SspI, and the resulting 519 bp fragment of the truncated AtRPD3A cDNA in the antisense orientation was used to replace the GUS gene of the pCBtCUP.

To generate AtHD2A antisense construct, the AtHD2A cDNA fragment was obtained using the polymerase chain reaction procedure. The 738 bp of full-length AtHD2A cDNA was amplified in two primer pairs (AATTGAGCTCAGCCATGGAGITCTGGGG: SEQ ID NO:10 and ACGTGGATCCAGAAACCACTTCACT-TGGC: SEQ ID NO:11). All primers had additional nucleotides at the 5' ends to give suitable restriction sites for cloning of the resulting fragments. The PCR product was digested by SacI and XmaI and used to replace the GUS gene of pCBtCUP.

Plant Transformation and Selection

Plant transformation plasmids were electroporated into *Agrobacterium tumefaciens* GV3101 (Van Larebeke et al. 1974) as described by Shaw (1995). The Agrobacterium-mediated transformation of *Arabidopsis thaliana* was performed as described previously (Clough and Bent, 1998), with the following modifications. Plants with immature floral buds and few siliques were dipped into a solution containing *Agrobacterium tumefaciens*, 2.3 g/L MS salts (Sigma), 5% (w/v) sucrose and 0.03% Silwet L-77 (Lehle Seeds, Round Rock, Tex.) for 1–2 min. T1 seeds were collected, dried at 25° C., and sown on sterile media containing 40 μg/mL kanamycin to select the transformants. Surviving T1 plantlets were transferred to soil to set seeds (T2).

Microscopic Analysis

For scanning electron microscopy, green siliques were dissected under the stereomicroscope and fixed in 4% glutaraldehyde and 4% paraformaldehyde in 0.1 M sodium phosphate buffer (pH7.2) for 16 hr. The samples were then dehydrated in a graded ethanol series (50–100%). The treated siliques were critical-point-dried using liquid $CO_2$ and mounted on scanning electron microscope stubs. The mounted specimens were coated with gold and observed with a scanning electron microscope.

The expansion of antisense AtRPD3A RNA in the transgenic lines was monitored by Northern analysis (FIG. 12). Two transcripts, a large transcript (1.6 kb) and a smaller transcript (0.6 kb), were detected using an AtRPD3A cDNA probe in the antisense transgenic lines (FIG. 12). The smaller transcript was absent from the wild-type plants and represented the AtRPD3A antisense transcript. As shown in FIG. 12, different levels of endogenous sense AtRPD3A transcript were detected in three independent antisense lines with high levels of expression of antisense transcript. As shown in FIG. 14, control wild-type plants started flowering after approximately 3 weeks of vegetative growth. In contrast, flowering of the antisense lines A1 and B5 was delayed for two to three weeks. These results suggest that AtRPD3A is important for normal plant growth and development.

To further study the function of HD2-like proteins, transgenic Arabidopsis (ecotype Columbia) were constructed. These plants expressed antisense AtHD2A from a strong constitutive promoter, -394-tCUP. The expression of the AtHD2A antisense gene in the transgenic lines was verified by Northern analysis. An antisense specific probe derived from the 5' untranslated region of the AtHD2A antisense construct was used to monitor the expression of the AtHD2A antisense gene. As shown in FIG. 13, five independent transgenic lines showed high expression of antisense AtHD2 transcript. A 3' untranslated region of AtHD2A cDNA, which was absent from the AtHD2A antisense construct was used to detect the endogenous AtHD2A mRNA. As shown in FIG. 13, the levels of endogenous AtHD2A transcript were significantly reduced in the transgenic lines, indicating that antisense transcripts might trigger AtHD2 mRNA degradation.

The five independent transgenic lines with reduced endogenous AtHD2A RNA levels had stunted siliques and produced fewer seeds compared with wild-type (FIG. 15), and they were therefore semi-sterile. The wild-type plants were distinguished from the transgenic plants by the length of the siliques and the seed set. In the semi-sterile transgenic plants, silique length and seed set varied along the stem and from inflorescence to inflorescence. Siliques from the wild type and the sterile transgenic plants were dissected and examined by stereomicroscopy and scanning electron microscopy. As shown in FIG. 16, the transgenic mature siliques contained aborted seeds, which were significantly smaller than the healthy seeds from the wild-type plants.

EXAMPLE 4

Tissue Specific Gene Repression

The above examples demonstrate repression of GUS reporter gene activity regulated by a constitutive regulatory element fused to a controlling sequence (for example a yeast upstream activating sequence) specific for a controlling sequence binding domain (for example the yeast GAL4 protein DNA binding domain; $UAS_{GAL}$). This example demonstrates the repression of gene expression in a tissue dependant manner using a tissue-specific regulatory element, for example the napin promoter (a seed specific regulatory element) that drives the expression of the GAL4-HD protein. Results presented below demonstrate that the expression of a target gene that is regulated by any promoter (including a constitutive promoter) may be repressed in a tissue-specific manner. An outline of the experimental approach is presented in FIG. 17(A). Constructs used are schematically presented in FIG. 17(B).

$UAS_{GAL4}$-tCUP-GUS and $UAS_{GAL4}$-35S-GUS reporter constructs (FIG. 17(B)) were used to transform Arabidopsis using standard techniques (Clough and Bent, 1998) to generate reporter lines. Thirteen $UAS_{GAL4}$-tCUP-GUS lines and eight $UAS_{GAL4}$-35S-GUS lines were generated and the expression of GUS gene was screened for GUS activity by histochemical assay. All of thirteen $UAS_{GAL4}$-tCUP-GUS reporter lines and six of eight $UAS_{GAL4}$-35S-GUS reporter lines showed intense GUS staining.

Effector lines were generated by using effector plasmids, tCUP-GAL4/AtHD2A and NAP-GAL4/AtHD2A (FIG. 15(B)). Thirteen tCUP-GAL4/AtHD2A and six NAP-GAL4/At2A effector lines were generated Southern analysis indicated that all of the effector lines carry GAL4/AtHD2A gene (data not shown). Northern analysis indicated that four of the thirteen tCUP-GAL4/AtHD2A effector showed strong expression of GAL4/AtHD2A mRNA (data not shown).

Three $UAS_{GAL4}$-tCUP-GUS lines were crossed with three tCUP-GAL4/AtHD2A and NAP-GAL4/AtHD2A effector lines, respectively. Analysis of the F1 progeny from a cross between $UAS_{GAL4}$-tCUP-GUS X 35S-GAL4/AtHD2A (Effector 1), and $UAS_{GAL4}$-tCUP-GUS X NAP1-GAL4/AtHD2A (Effector 2) is presented in FIG. 19. High levels of reporter gene activity are observed in leaves and seeds in control plants expressing GUS under the control of the constitutive regulatory element tCUP. In F1 progeny of plants derived from a cross between UAS$_{Gal4}$-tCUP-GUS X 35S-GAL4/AtHD2A (Effector 1), reduced reporter gene expression is observed in both leaves and seeds, due to the constitutive expression of the HD/GAL4BD, and the UAS$_{Gal4}$-reporter genes. In F1 progeny derived from a cross between UAS$_{Gal4}$-tCUP-GUS X NAP1-GAL4/AtHD2A (Effector 2), high levels of reporter gene expression are observed in leaf tissue only, with seed specific reporter expression is dramatically reduced due to the targeted expression of the HD/GAL4BD gene in seed tissues only.

These results indicate that tissue specific repression of gene activity can be achieved though tissue specific expression of a gene encoding a controlling sequence-binding domain.

EXAMPLE 5

Sequential Transformation of Plants with Target and Effector Constructs

Repression of a coding sequence of interest may occur within a plant following sequential transformation of a target gene, for example GUS, followed by transformation with an effector gene. To demonstrate the efficacy of this approach, Arabidopsis plants were transformed using standard techniques (Clough and Bent, 1998) using the construct UAS$_{GAL4}$-tCUP-GUS (tCUP-GUS; reporter gene). As shown in FIGS. 19(B) and (C), these plants (indicated as control 1, 2) exhibit GUS activity in both leaves and seeds. Transformed plants expressing GUS were then re-transformed with one of two effector constructs, 35S-GAL4/AtHD2A, or NAP1-GAL4/AtHD2A. The levels of GUS activity within the dual transgenics are shown in FIGS. 19(B) and (C).

Figure 19A:
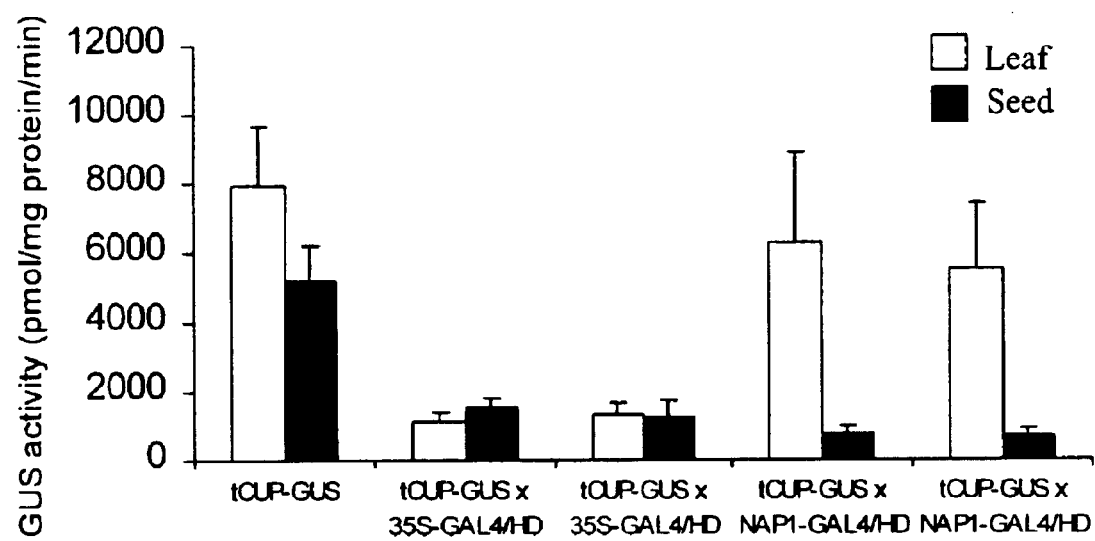
FIG. 19(A) shows GUS specific activity analyzed in the leaves and seeds of the reporter line tCUP-GUS and F1 progeny produced from the cross between tCUP-GUS X 35S-GAL4/AtHD2A, and tCUP-GUS X NAP1-GAL4/AtHD2A. Ten to 15 plants from the reporter line and each cross were analyzed.
Figure 19B:
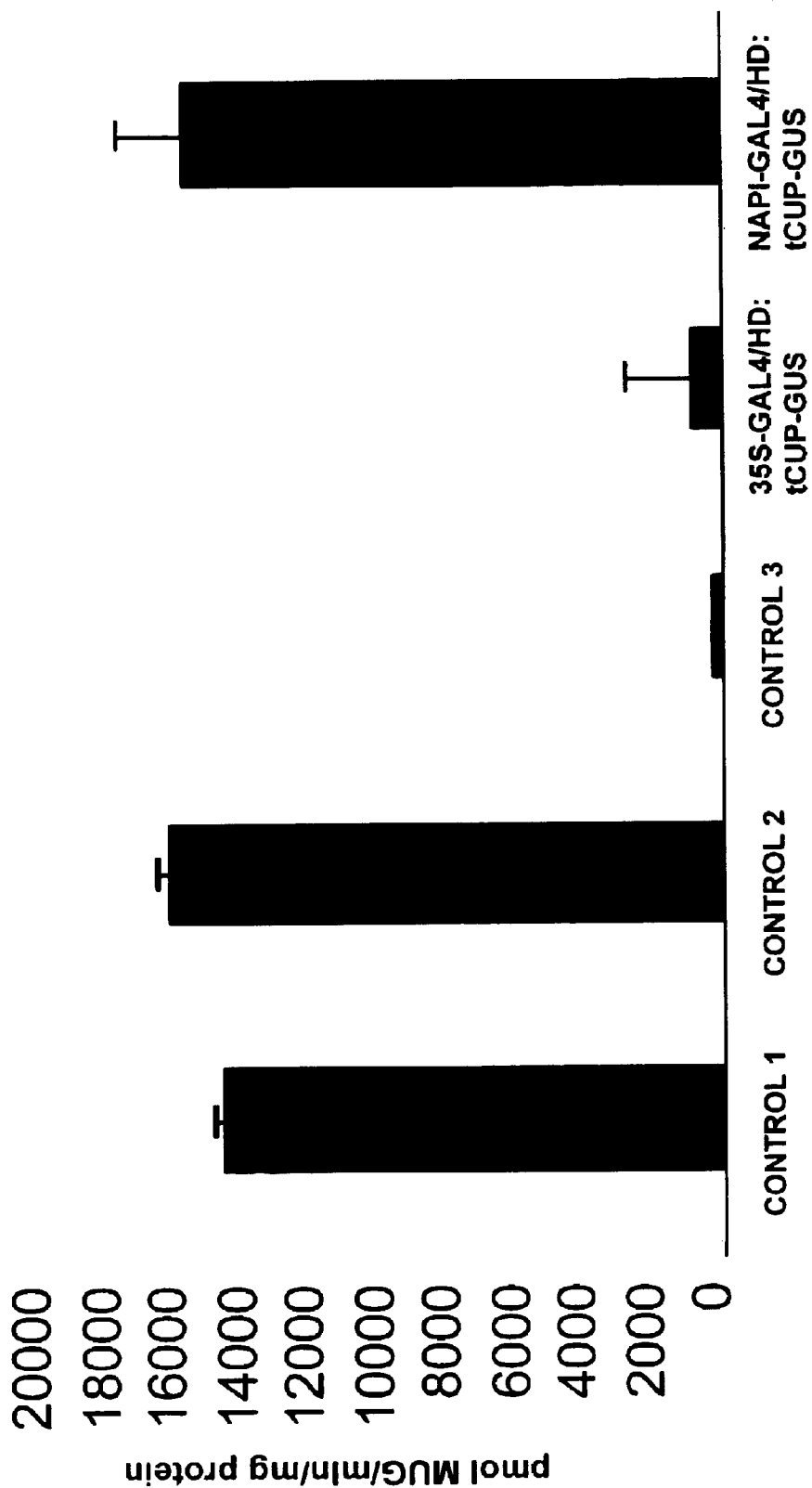
FIG. 19(B) shows GUS specific activity analyzed in leaves of plants transformed with tCUP-GUS (UAS$_{GAL4}$-tCUP-GUS) (control 1, 2), and plants sequentially transformed with tCUP-GUS (UAS$_{GAL4}$-tCUP-GUS) followed by a second transformation with either 35S-GAL4/AtHD2A (35S-GAL4/HD:tCUP-GUS) or Napin-GAL4/AtHD2A (NAP1-GAL4/HD:tCUP-GUS). Control 3, plants transformed with 35S-GAL4/AtHD2A only. Three plants were assayed for each treatment.
Figure 19C:
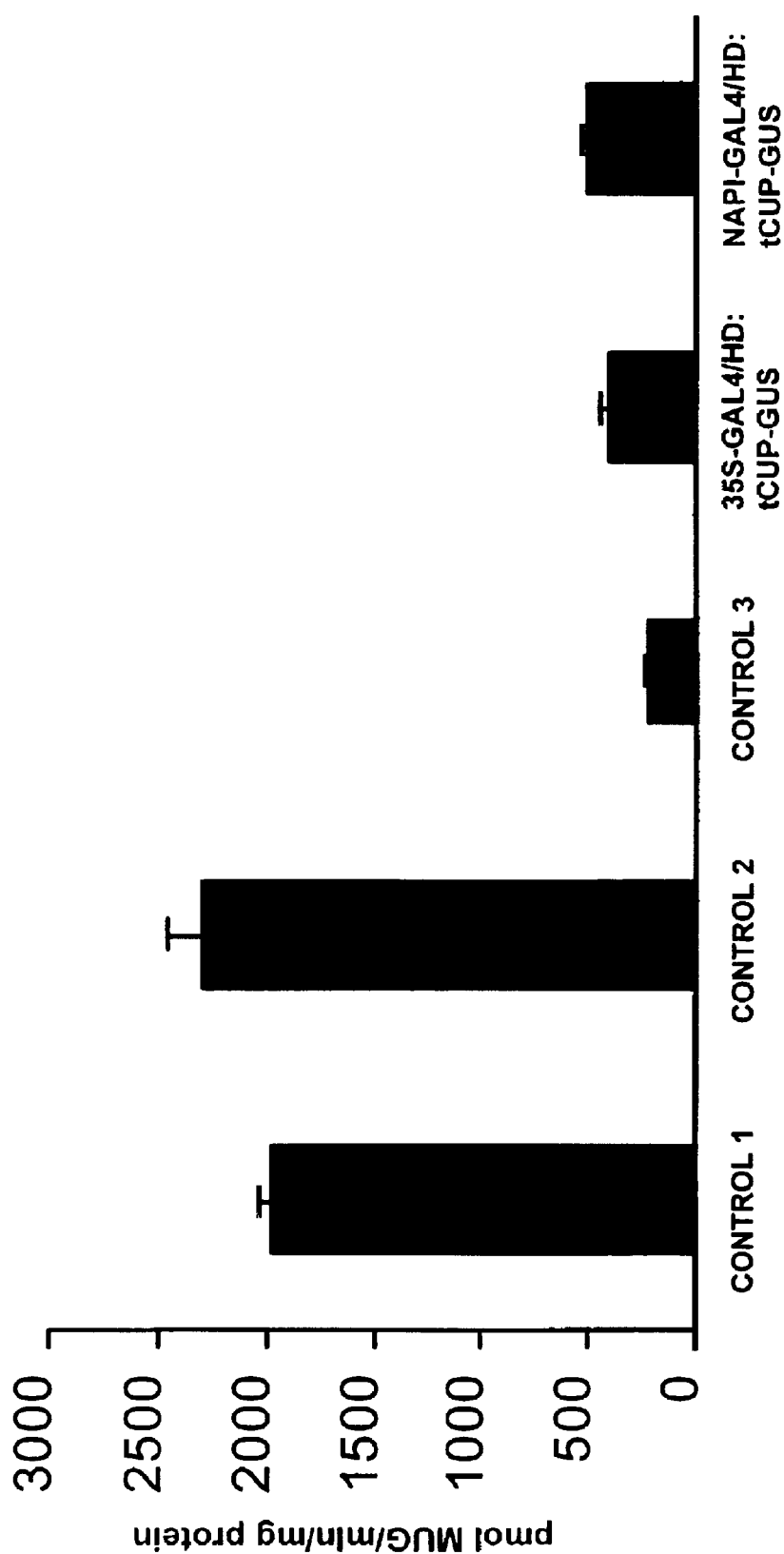
FIG. 19(C) shows GUS specific activity analyzed in seeds of plants transformed with tCUP-GUS (UAS$_{GAL4}$-tCUP-GUS) (control 1, 2), and plants sequentially transformed with tCUP-GUS (UAS$_{GAL4}$-tCUP-GUS) followed by a second transformation with either35S-GAL4/AtHD2A (35S-GAL4/HD:tCUP-GUS) or Napin-GAL4/

In plants sequentially transformed with the reporter construct and an effector construct that is constitutively expressed in the plant (35S-GAL4/HD), repression of GUS activity was observed in both leaves and seed (FIGS. 19(A) and (B)). The repression of GUS activity was only observed in seed tissues on plants re-transformed with the seed specific effector construct NAP1-GAL4/HD. No repression of reporter gene activity was observed in leaf tissue in dual transgenic plants re-transformed with the seed specific effector construct (FIGS. 19(A) and (B)).

These results demonstrate that sequentially transformed plants exhibit a similar repression of an expression construct (i.e. reporter gene) by an effector construct, as that observed in progeny produced from crosses between reporter plants (comprising an expression construct) and effector plants (comprising an effector construct). Furthermore, these results show that repression of gene expression may be specifically targeted in a tissue-specific manner.

EXAMPLE 6

Use of Plant Transcription Factors to Repress Developmental Pathway

Since the targeting of histone deacetylases to specific gene sequences using transcription factor DNA binding domains provides an effective method for repressing or silencing target genes. It was examined whether this approach is also useful for the repression of developmental, and metabolic pathways in plants. This example demonstrates that the plant transcriptional factor Pti4 and histone deacetylase fusion proteins can be used to control plant developmental pathways.

Pti4 is a tomato transcription factor that belongs to the ERF (ethylene-responsive element binding factor) family of proteins. It interacts with the Pto kinase in tomato, which confers resistance to the *Pseudomonas syringae* pv tomato pathogen that causes bacterial speck disease. To study the function of Pti4, transgenic Arabidopsis plants were generated that expressed tomato Pti4 driven by the strong constitutive promoters, CaMV 35S and -394tCUP.

Northern analysis (see below) demonstrate that expression of Pti4 in transgenic Arabidopsis plants induced the expression of a GCC box-containing PR gene, basic chitinase, in Arabidopsis. It was also observed that Pti4 enhanced GCC box-mediated transcription of a reporter gene (see below). Expression of tomato Pti4 in transgenic Arabidopsis plants produced a phenotype similar to that seen in plants treated with ethylene, suggesting that the Pti4 gene is involved in the regulation of a subset of ethylene responsive genes which contain the GCC box. These results therefore suggest that tomato Pti4 acts as a transcriptional activator to regulate expression of GCC box-containing genes.

The Pti4 activator was therefore used as a controlling sequence-binding domain. Since Pti4 is capable of interacting with a controlling sequence, in this case a GCC box, the introduction of a Pti4-AtHD2A fussion into a plant should result in the repression of the phenotype associated with ethylene response. This in fact is observed, as the expression of the Pti4-AtHD2A fussion in transgenic Arabidopsis, represssed the ethylene-responsive phenotype.

Pti4 Protein Activates GCC Box-mediated Transcription of a Reporter Gene

To test if the tomato Pti4 protein can interact with the GCC-box, Pti4 effector plasmids were constructed in which the Pti4 cDNA was driven by the strong constitutive promoters, CaMV 35S or tCUP (FIG. 20(A)). The reporter plasmids, GCC/GUS and mGCC/GUS (not shown), were constructed using a GUS reporter gene. Two GCC-boxes or mutated GCC-boxes (mGCC) (Ohme-Takagi and Shinshi, 1995) were fused to a minimal promoter, 62tCUP (Foster et al., 1999) to drive the GUS reporter gene expression. The effector plasmids were cobombarded into tobacco leaves together with a reporter plasmid. As shown in FIG. 20(B), co-transfection of the reporter plasmid GCC/GUS with a effector plasmid resulted in a 3 to 4fold increase in GUS expression, indicating that Pti4 protein can interact with the GCC-boxes in the promoter of the reporter construct to activate transcription. Transcription of the reporter gene that had a mutated GCC-box was not activated by Pti4 (data not shown).

Ectopic Expression of Tomato Pti4 Induces Resident Basic Chitinase Gene Expression Transgenic Arabidopsis plants were generated that expressed Pti4 driven by the strong constitutive promoters, CaMV 35S or tCUP (Foster et al., 1999). Southern blot analysis was performed to determine whether the genomic DNA of the putative transformants contained the transgenic DNA (data not shown). Four of the transgenic lines (tCUP/Pti4-1, tCUP/Pti4-3 and tCUP/Pti4-4, tCUP/Pti4-5) contained the Pti4 transgene driven by tCUP promoter and two transgenic lines (35S/Pti4-3 and 35S/Pti4-6) contained Pti4 transgene driven by CaMV 35S promoter.

The expression of Pti4 RNA in the transgenic lines was determined by Northern analysis. The predicted 1 kb transcript was detected in five transgenic lines, tCUP/Pti4-3, tCUP/Pti4-4, tCUP/Pti4-5, 35S/Pti4-1 and 35S/Pti4-2, using the Pti4 cDNA probe. Low expression was also noted in tCUP/Pti4-3, and no expression was observed in wild-type plants (WT; FIG. 21). One transgenic line, tCUP/Pti4-5, showed bands that were larger in size than the bands in the other lanes of the transgenic plants. This is most likely due to the downstream termination of transcription. Different levels of Pti4 transcript accumulation were detected in the transgenic lines, with the transgenic line tCUP/Pti4-1 having the lowest level of Pti4 expression.

Solano et al. (1998) reported that overexpression of another ERF (ethylene-responsive element binding factor) protein, ERF1, in transgenic Arabidopsis plants induced basic chitinase gene expression. Basic chitinase is an ethylene-responsive gene, which contains the GCC box in its promoter (Samac et al., 1990). Therefore, the expression of tomato Pti4 in Arabidopsis was examined to determine if Pti4 could induce the expression of the Arabidopsis basic chitinase gene.

As shown in the FIG. 21, the basic chitinase (BC) gene was expressed at a relative low level in the wild-type but was induced in the transgenic lines tCUP/Pti4-3, tCUP/Pti4-4, tCUP/Pti4-5, 35S/Pti4-1 and 35S/Pti4-2. The transgenic line tCUP/Pti4-1, which had the lowest level of Pti4 expression among the 6 transgenic lines, did not show the induction of chitinase expression. The transgenic line tCUP/Pti4-3 that had the highest level of Pti4 mRNA expression showed the highest level of basic chitinase mRNA accumulation. These data indicated that there was a general correlation between Pti4 expression and chitinase RNA accumulation, suggesting that Pti4 induced the expression of the basic chitinase gene in Arabidopsis.

Transgenic Pti4 Plants Display an Ethylene-responsive Phenotype

To evaluate the involvement of Pti$^4$ in the ethylene signaling pathway, Pti4 transgenic plant lines were examined for the ethylene-responsive phenotype. This phenotype is characterised by a triple response in Arabidopsis which includes inhibition of root and hypocotyl elongation, radial swelling of the hypocotyl and root, and exaggeration in the curvature of the apical hook (Ecker, 1995; Chang and Shockey, 1999). The hypocotyls of the etiolated transgenic seedlings were measured 72 hrs after germination. Among the 6 independent transgenic lines, four transgenic lines (tCUP/Pti4-3, tCUP/Pti4-4, tCUP/Pti4-5 and 35S/Pti4-1) with high Pti4 gene expression showed inhibition of hypocotyl elongation, a phenotype similar to those observed in the constitutive ethylene response-mutants or in wild-type plants exposed to ethylene (Solano et al., 1998). As shown in the FIGS. 22 and 23, the seedlings from the transgenic line tCUP/Pti4-1 displayed strong inhibition of hypocotyl elongation. A similar response (inhibition of hypocotyl elongation) is observed in plants exposed to 1-aminocyclopropane-1-carboxylic acid (AAC), a precursor of ethylene biosynthesis (FIGS. 22, 23). The seedlings from the transgenic line tCUP/Pti4-1, which had a lower level of Pti4 transgenic expression, showed weak inhibition of hypocotyl elongation (FIG. 22). These data indicated that there was a correlation between the Pti4 expression and the inhibition of hypocotyl elongation

Expression of Pti4.AtHD2A Represses Ethylene-responsive Phenotype

To test the effect of Pti4-At2A protein on the ethylene signaling pathway, transgenic plants overexpressing Pti4-AtFD2A were generated by using tCUP promoter. The Arabidopsis transgenic plants expressing Pti4-HD2A fusion protein was examined for the ethylene-responsive phenotype. The hypocotyls of the etiolated transgenic seedlings were measured 72 hrs after germination. As shown in the FIG. 24, wild type seedlings (FIG. 24(A)) exhibited hypocotyl elongation. Seedlings overexpressing Pti4 (FIG. 24(B)) exhibited the ethylene responsive phenotype (inhibition of hypocotyl elongation). However, seedlings from the transgenic line Pti4-HDA (FIG. 24(C)) did not display inhibition of hypocotyl elongation, demonstrating that Pti4-AtHDA fusion proteins repressed ethylene responsive phenotype in transgenic plants. These results indicate that the Pti4 functions as a controlling sequence-binding domain and is capable of interacting with a controlling sequence (GCC box), and target HD to repress gene expression of an endogenous gene in a targeted manner.

All citations are herein incorporated by reference.

The present invention has been described with regard to preferred embodiments. However, it will be obvious to persons skilled in the art that a number of variations and modifications can be made without departing from the scope of the invention as described herein.

References

Alland, L., Muhlw, R., Hou, H., Jr, Postes., Chin, L., Schreiber-Agus, N., and De Pinho, R. A. (1997) Role of NcoR and histone deacetylase in Sin3-mediated transcriptional and oncogenic repression, Nature 387, 49–55.

Altschul, S. F., Gish, W., Miller, W., Myers, E. W., and Lipman, D. J. (1990) Basic local alignment search tool. J. Mol. Biol. 215, 403–10

Aravind, L., and Koonin. E. V. (1998) Second family of histone deacetylases. Science 280, 1167a.

Broglie K E, Biddle P, Cressman R. Broglie R (1989) Functional analysis of DNA sequences responsible for ethylene regulation of a bean chitinase gene in transgenic tobacco. Plant Cell 1: 599–607.

Brown, D. C. W., Tian, L. -N., Buckley, D. J., Lefebvre, M., McGrath, A., and Webb, J. (1994) Development of a simple particle bombardment device for gene delivery into plant cells. Plant Cell Tiss. Org. Cult. 37: 47–53.

Chang C, Shockey J A (1999) The ethylene-response pathway: signal perception to gene regulation. Curr. Opin. Plant Biol. 2: 352–358.

Clough, S. J., and Bent, A. F. (1998) Floral dip: a simplified method for Agrobacterium-mediated transformation of Arabidopsis thaliana. Plant J. 16, 735–743.

Dellaporta, S. L, Wood, J., and Hicks, J. B. (1983) A plant DNA minipreparation, version II. Plant Mol. Rep. 1, 19–21

Ecker J R (1995) The ethylene signal transduction pathway in plants. Science 268: 667–675.

Emiliani, S., Fischle W., Lint V., Al-Abed Y., and Verdin E. (1998) Characterization of a human RPD3 ortholog, HDAC3. Proc. Nati. Acad. Sci. USA 95, 2795–2800

Fischle, W., Emiliani, S., Hendzel, M. J., Nagase, T., Nomura, N., Voelter, W., and Verdin, E. (1999) A new family of human histone deacetylases related to Saccharomyces cerevisiae HDA1p. J. Biol. Chem. 274, 11713–11720.

Foster E, Hattori J, Labbe H, Oucliet T, Fobert P, James L, Miki B (1999) A tobacco cryptic constitutive promoter, tCUP, revealed by T-DNA tagging. Plant Mol. Biol. 41: 45–55.

Garnborg, O. L., Miller, R. A., and Ojima, K. (1968) Nutrient requirement suspension cultures of soybean root cells. Exp. Cell Res. 50, 151–158.

Gelmetti, V., Zhang, J., Fanelli, M., Minucci, S., Pelicci, P. G., and Lazar, M. A. (1998) Aberrant recruitment of the nuclear receptor corepressor-histone deacetylase complex by the acute myeloid leukemia fusion partner ETO. Mol. Cell. Biol. 18, 7185–7191.

Giniger, E., Varnum, S. M., and Ptashne, M. (1985) Specific DNA binding of GAL4, a positive regulatory protein of yeast. Cell 40, 767–774.

Hassig, C. A., Fleischer, T. C., Billin, A. N., Schreiber, S. L., and Ayer, D. E. (1997) Histone deacetylase activity is required for full transcriptional repression by mSin3A. Cell 89, 341–347.

Hassig, C. A., Tong J. K., Fleischer, T. C., Owa T., Grable P. G., Ayer D. E., and Schreiber S. L. (1998) A role for histone deacetylase activity in HDAC1-mediated transcriptional repression. Proc. Natl. Acad. Sci. USA 95, 3519–3524.

Jefferson, R. (1988) Plant reporter genes: the GUS gene fusion system. In Genetic Engineering: Principles and Methods, J. K. Setlow and A. Hollaender, eds (New York, Plenum Press), pp. 247–263.

Kadosh, D., and Struhl, K. (1997) Repression by Ume6 involves recruitment of a complex containing Sin3 corepressor and Rpd3 histone deacetylase to target promoter. Cell 89, 365–371.

Kadosh, D., and Struhl, K. (1998) Histone deacetylase activity of Rpd3 is important for transcriptional repression in vivo. Genes Dev. 12, 797–805.

Khochbin, S., and Wolffe A. P. (1997) The origin and utility of histone deacetylases. FEBS Lett. 419,157–160.

Ladomery, M., Lyons, S., and Sommerville. J. (1997) Xenopus HDm, a maternally expressed histone deacetylase, belongs to an ancient family of acetyl-metabolizing enzymes Gene 198. 275–280.

Leipe, D., and Landsman, D. (1997) Histone deacetylases, acetoin utilization proteins and acetylpolyamine amidohydrolases are members of an ancient protein superfamily. Nucleic Acids Res. 18, 3693–3697.

Lusser, L., Broach, G., Ladle, A., Haaf, H., and Ladle, P. (1997) Identification of maize histone deacetylase HD2 as an acidic nucleolar phosphoprotein. Science 277, 88–91.

Ma, J., Przibilla, E., Hu., J., Bogorad, L., and Ptashne, M. (1988) Yeast activators stimulate plant gene expression. Nature 334, 631–633.

Murashie, T., and Skoog, F. (1962) A revised medium for rapid growth and bioassay with tobacco tissue cultures. Physiol. Plant. 15: 473497.

Nagy, L., Kao, H. Y., Chakravarti, D., Lin, R. J., Hassig, C. A., Ayer, D. E., Schreiber, S. L., and Evans, R. M. (1997) Nuclear receptor repression mediated by a complex containing SMRT, mSin3A, and histone deacetylase. Cell 89, 1261–1270.

Ohme-Takagi M, Shinshi H (1995) Ethylene-inducible DNA binding proteins that interact with an ethylene-responsive element. Plant Cell 7: 173–182.

Pazin, M. J., and Kadonaga, J. T. (1997) What's up and down with histone deacetylation and transcription. Cell 89, 325–328.

Philpott, A., and Leno, G. H. (1992) Nucleoplasmin remodels sperm chromatin in Xenopus egg extracts. Cell 69, 759–767.

Rossi, V., Hartings, H., and Motto, M. (1998) Identification and characterization of an RPD3 homologue from maize (Zea mays L.) that is able to complement an rpd3 null mutant of Saccharomyces cerevisiae. Mol. Gen. Genet. 258, 288–296.

Rundlett, S. E., Carmen, A. A., Kobyashi, R., Bavykin, S., Turner, B. M., and Grunstein, M. (1996) HDA1 and RPD3 are members of distinct histone deacetylase complexes that regulate silencing and transcription. Proc. Natl. Acad. Sci. USA 93, 14503–14508.

Samac D A, Hironaka C M, Yallaly P E, Shah D M (1990) Isolation and characterization of the genes encoding basic and acidic chitinase in Arabidopsis thaliana, Plant Physiol. 93: 907–914.

Sambrook, J., Fritsch, E. F., and Maniatis, T. (1989) Molecular Cloning: A Laboratory Manual, Ed 2. (Cold Spring Harbor Laboratory Press, Cold Spring Harbor, N.Y.).

Shaw, C. H. (1995) Introduction of cloning plasmids in to Agrobacterium tumefaciens. Meth. Mol. Biol. 49, 33–37.

Shinshi H, Usami S, Ohme-Takagi M (1995) Identification of an ethylene-responsive region in the promoter of a tobacco class 1 chitinase gene. Plant Mol. Biol. 27: 923–32.

Solano R, Stepanova A, Chao Q, Ecker J R (1998) Nuclear events in ethylene signaling: a transcriptional cascade mediated by ETHYLENE-INSENSITIVE3 and ETHYLENE-RESPONSE-FACTOR1.Genes Dev. 12: 3703–3714.

Stromnmer, J., Gregerson, R., and Vayda, M. (1993) Isolation and characterization of plant mRNA. In Methods in Plant Molecular Biology and Biotechnology, B. R. Glik, and J. E. Thompson, eds (CRC Press, Boca Raton), pp. 49–66.

Struhl, K. (1998) Histone acetylation and transcriptional regulatory mechanisms. Genes Dev. 12, 599–606.

Taunton, J., Hassig, C. A., and Schreiber, S. L. (1996) A mammalian histone deacetylase related to a yeast transcriptional regulator Rpd3. Science 272, 408–411.

Van Larebeke, N., Engler, G., Holsters, M., Van den Elscker, S., Zainen, I., Schilperoort, R. A., and Schell, J. (1974) Large plasmid in Agrobacterium tumefaciens essential for crown gall-inducing ability. Nature 252,169–170.

Verdel, A., and Khochbin, S. (1999) Identification of a new family of higher eukaryotic histone deacetylases. J. Biol. Chem. 274, 2440–2445.

Vidal, M., and Gaber, R. F. (1991) RPD3 encodes a second factor required to achieve maximum positive and negative transcriptional states in Saccharomyces cerevisiae. Mol. Cell. Biol. 11, 6317–6327.

Workman, J. L., and Kingston, R. E. (1998) Alteration of nucleosome structure as a mechanism of transcriptional regulation. Annu. Rev. Biochem. 67, 545–579.

What is claimed is:

1. A method of repressing transcription of a coding sequence of interest in a transgenic plant, comprising:

a) introducing into a plant:

i) a first chimeric nucleotide sequence comprising a first regulatory element in operative association with said coding sequence of interest, and a controlling sequence; and ii) a second chimeric nucleotide sequence comprising a second regulatory element in operative association with a nucleotide sequence encoding a histone deacetylase fused with a DNA binding protein, said DNA binding protein interacting with said controlling sequence, to produce said transgenic plant; and b) growing said transgenic plant;

wherein said nucleotide sequence encoding a histone deacetylase is selected from the group consisting of:

AtRPD3A, a nucleotide sequence that hybridizes to AtRPD3A under a hybridization condition, AtRPD3B, a nucleotide sequence that hybridizes to AtRPD3B under a hybridization condition, AtHD2A, a nucleotide sequence that hybridizes to AtHD2A under a hybridization condition, AtHD2B, a nucleotide sequence that hybridizes to AtHD2B under a hybridization condition, nucleotides 1–1807 of SEQ ID NO:1, a nucleotide sequence that hybridizes to nucleotides 1–1807 of SEQ ID NO:1 under a hybridization condition, nucleotides 142–1644 of SEQ ID NO:1, a nucleotide sequence that hybridizes to nucleotides 142–1644 of SEQ ID NO:1 under a hybridization condition, nucleotides 1–1800 of SEQ ID NO:3, a nucleotide sequence that hybridizes to nucleotides 1–1800 of SEQ ID NO:3 under a hybridization condition, nucleotides 121–1533 of SEQ ID NO:3, a nucleotide sequence that hybridizes to nucleotides 121–1533 of SEQ ID NO:3 under a hybridization condition, nucleotides 1–939 of SEQ ID NO:5, a nucleotide sequence that hybridizes to nucleotides 1–939 of SEQ ID NO:5 under a hybridization condition, nucleotides 49–783 of SEQ ID NO:5, a nucleotide sequence that hybridizes to nucleotides 49–783 of SEQ ID NO:5 under a hybridization condition, nucleotides 49–681 of SEQ ID NO:5, a nucleotide sequence that hybridizes to nucleotides 49–681 of SEQ ID NO:5 under a hybridization condition, nucleotides 49–534 of SEQ ID NO:5, a nucleotide sequence that hybridizes to nucleotides 49–534 of SEQ ID NO:5 under a hybridization condition, nucleotides 1–1212 of SEQ ID NO:7, a nucleotide sequence that hybridizes to nucleotides 1–1212 of SEQ ID NO:7 under a hybridization condition, and nucleotides 61–975 of SEQ ID NO:7, a nucleotide sequence that hybridizes to nucleotides 61–975 of SEQ ID NO:7 under a hybridization condition;

wherein each said hybridization condition is selected from the group consisting of:

hybridization in 4×SSC at 65° C., followed by washing in 0.1×SSC at 65° C. for an hour, hybridization in 50% formamide and 4×SSC at 42° C., followed by washing in 0.1×SSC at 65° C. for an hour, and hybridization in 0.5 M $Na_2HPO_4$ (pH 7.2), 7% SDS, and 1 mM EDTA at 65° C., followed by washing for 15 minutes in 2×SSC with 0.1% SDS at room temperature, then washing twice for 20 minutes in 0.1×SSC, 0.1% SDS at 65° C.; and wherein said nucleotide sequence that hybridizes encodes a product that exhibits transcription repression activity.

2. The method of claim 1 wherein the step of introducing comprises sequentially transforming said plant with said first, and said second, chimeric nucleotide sequence, or co-transforming said plant with said first and said second chimeric nucleotide sequences.

3. The method of claim 1, wherein the step of introducing comprises transforming a first plant with said first chimeric nucleotide sequence, and transforming a second plant with said second chimeric nucleotide sequence, followed by a step of crossing said first and said second plant, to produce said transgenic plant.

4. The method of claim 1 wherein said first chimeric nucleotide sequence and the second chimeric nucleotide sequence, within said step of introducing, are contiguous within one construct.

5. The method of claim 1 wherein the first chimeric nucleotide sequence and the second chimeric nucleotide sequence, within said step of introducing, are separate constructs.

6. The method of claim 1 wherein said DNA binding protein, within the step of introducing, is selected from the group consisting of GAL4, AP2 domain proteins, APETALA2, PRbox binding protein, CCAAT-box binding proteins, LEC1, BNM3, Pti4, and PICKLE.

7. The method of claim 1 wherein said first and said second regulatory region, within said step of introducing, are selected from the group consisting of constitutive, tissue specific, developmentally-regulated, and inducible regulatory elements.

8. An isolated nucleotide sequence, selected from the group consisting of:

SEQ ID NO:3, a nucleotide sequence that hybridizes to SEQ ID NO:3 under a hybridization condition,

SEQ ID NO:5, a nucleotide sequence that hybridizes to SEQ ID NO:5 under a hybridization condition,

SEQ ID NO:7, a nucleotide sequence that hybridizes to SEQ ID NO:7 under a hybridization condition, nucleotides 1–1800 of SEQ ID NO:3, a nucleotide sequence that hybridizes to nucleotides 1–1800 of SEQ ID:NO:3 under a hybridization condition, nucleotides 121–1533 of SEQ ID NO:3, a nucleotide sequence that hybridizes to nucleotides 121–1533 of SEQ ID NO:3 under a hybridization condition, nucleotides 1–939 of SEQ ID NO:5, a nucleotide sequence that hybridizes to nucleotides 1–939 of SEQ ID NO:5 under a hybridization condition, nucleotides 49–783 of SEQ ID NO:5, a nucleotide sequence that hybridizes to nucleotides 49–783 of SEQ ID NO:5 under a hybridization condition, nucleotides 49–681 of SEQ ID NO:5, a nucleotide sequence that hybridizes to nucleotides 49–681 of SEQ ID:NO:5 under a hybridization condition, nucleotides 49–534 of SEQ ID NO:5, a nucleotide sequence that hybridizes to nucleotides 49–534 of SEQ ID NO:5 under a hybridization condition, nucleotides 1–1212 of SEQ ID NO:7, a nucleotide sequence that hybridizes to nucleotides 1–1212 of SEQ ID NO:7 under a hybridization condition, nucleotides 61–975 of SEQ ID NO:7, and a nucleotide sequence that hybridizes to nucleotides 61–975 of SEQ ID NO:7 under a hybridization condition;

wherein each said hybridization condition is selected from the group consisting of:

hybridization in 4×SSC at 65° C., followed by washing in 0.1×SSC at 65° C. for an hour, hybridization in 50% formamide and 4×SSC at 42° C., followed by washing in 0.1×SSC at 65° C. for an hour, and hybridization in 0.5 M Na$_2$HPO$_4$ (pH 7.2), 7% SDS, and 1 mM EDTA at 65° C., followed by washing for 15 minutes in 2×SSC with 0.1% SDS at room temperature, then twice washing for 20 minutes in 0.1×SSC, 0.1% SDS at 65° C.; and wherein said nucleotide sequence that hybridizes encodes a product that exhibits transcription repression activity.

9. A chimeric construct comprising a regulatory element in operative association with said isolated nucleotide sequence of claim 8.

10. The chimeric construct of claim 9 further comprising a nucleotide sequence encoding a DNA binding protein.

11. A vector comprising said chimeric construct of claim 10.

12. A transgenic plant cell produced by the method of claim 1.

13. A transgenic plant produced by the method of claim 1.

14. A transgenic seed produced by the method of claim 1.

15. A transgenic plant comprising said isolated nucleotide sequence as defined by claim 8.

16. A transgenic plant cell comprising said isolated nucleotide sequence as defined by claim 8.

17. A transgenic seed comprising said isolated nucleotide sequence as defined by claim 8.

18. An isolated nucleotide sequence selected from the group consisting of SEQ ID NO:3, SEQ ID NO:5 and SEQ ID NO:7.

19. The method of claim 1, wherein said nucleotide sequence encoding a histone deacetylase is selected from the group consisting of: AtRPD3A, AtRPD3B, AtHD2A, and AtHD2B.

20. The method of claim 1, wherein said nucleotide sequence encoding a histone deacetylase is selected from the group consisting of nucleotides 1–1807 of SEQ ID NO:1 and nucleotides 142–1644 of SEQ ID NO:1.

21. The method of claim 1, wherein said nucleotide sequence encoding a histone deacetylase is selected from the group consisting of: nucleotides 1–1800 of SEQ ID NO:3 and nucleotides 121–1533 of SEQ ID NO:3.

22. The method of claim 1, wherein said nucleotide sequence encoding a histone deacetylase is selected from the group consisting of: nucleotides 1–939 of SEQ ID NO:5; nucleotides 49–783 of SEQ ID NO:5; nucleotides 49–681 of SEQ ID NO:5; and nucleotides 49–534 of SEQ ID NO:5.

23. The method of claim 1, wherein said nucleotide sequence encoding a histone deacetylase is selected from the group consisting of: nucleotides 1–1212 of SEQ ID NO:7, and nucleotides 61–975 of SEQ ID NO:7.

24. The method of claim 1, wherein said nucleotide sequence encoding a histone deacetylase is selected from the group consisting of: a nucleotide sequence that hybridizes to AtRPD3A, a nucleotide sequence that hybridizes to AtRPD3B, a nucleotide sequence that hybridizes to AtHD2A, and a nucleotide sequence that hybridizes to AtHD2B.

25. The method of claim 1, wherein said nucleotide sequence encoding a histone deacetylase is selected from the group consisting of: a nucleotide sequence that hybridizes to nucleotides 1–1807 of SEQ ID NO:1 and a nucleotide sequence that hybridizes to nucleotides 142–1644 of SEQ ID NO:1.

26. The method of claim 1, wherein said nucleotide sequence encoding a histone deacetylase is selected from the group consisting of: a nucleotide sequence that hybridizes to nucleotides 1–1800 of SEQ ID NO:3 and a nucleotide sequence that hybridizes to nucleotides 121–1533 of SEQ ID NO:3.

27. The method of claim 1, wherein said nucleotide sequence encoding a histone deacetylase is selected from the group consisting of: a nucleotide sequence that hybridizes to nucleotides 1–939 of SEQ ID NO:5; a nucleotide sequence that hybridizes to nucleotides 49–783 of SEQ ID NO:5; a nucleotide sequence that hybridizes to nucleotides 49–681 of SEQ ID NO:5; and a nucleotide sequence that hybridizes to nucleotides 49–534 of SEQ ID NO:5.

28. The method of claim 1, wherein said nucleotide sequence encoding a histone deacetylase is selected from the group consisting of: a nucleotide sequence that hybridizes to nucleotides 1–1212 of SEQ ID NO:7 and a nucleotide sequence that hybridizes to nucleotides 61–975 of SEQ ID NO:7.

29. The isolated nucleotide sequence of claim 8, wherein said nucleotide sequence comprises SEQ ID NO:3.

30. The isolated nucleotide sequence of claim 8, wherein said nucleotide sequence comprises SEQ ID NO:5.

31. The isolated nucleotide sequence of claim 8, wherein said nucleotide sequence comprises SEQ ID NO:7.

32. The isolated nucleotide sequence of claim 8, wherein said nucleotide sequence comprises nucleotides 121–1533 of SEQ ID NO:3.

33. The isolated nucleotide sequence of claim 8, wherein said nucleotide sequence comprises nucleotides 1–939 of SEQ ID NO:5.

34. The isolated nucleotide sequence of claim 8, wherein said nucleotide sequence comprises nucleotides 49–783 of SEQ ID NO:5.

35. The isolated nucleotide sequence of claim 8, wherein said nucleotide sequence comprises nucleotides 49–681 of SEQ ID NO:5.

36. The isolated nucleotide sequence of claim 8, wherein said nucleotide sequence comprises nucleotides 49–534 of SEQ ID NO:5.

37. The isolated nucleotide sequence of claim 8, wherein said nucleotide sequence comprises nucleotides 1–1212 of SEQ ID NO:7.

38. The isolated nucleotide sequence of claim 8, wherein said nucleotide sequence comprises nucleotides 61–975 of SEQ ID NO:7.

* * * * *